United States Patent
Huddersman et al.

(10) Patent No.: US 8,513,303 B2
(45) Date of Patent: Aug. 20, 2013

(54) ANTIMICROBIAL AGENT

(75) Inventors: Katherine Huddersman, Leicester (GB); Susannah Elizabeth Walsh, Leicester (GB)

(73) Assignee: De Montfort University, Leicester (GB)

( * ) Notice: Subject to any disclaimer, the term of this patent is extended or adjusted under 35 U.S.C. 154(b) by 221 days.

(21) Appl. No.: 12/675,054

(22) PCT Filed: Aug. 22, 2008

(86) PCT No.: PCT/GB2008/002864
§ 371 (c)(1),
(2), (4) Date: Feb. 24, 2010

(87) PCT Pub. No.: WO2009/027649
PCT Pub. Date: Mar. 5, 2009

(65) Prior Publication Data
US 2011/0111053 A1    May 12, 2011

(30) Foreign Application Priority Data

Aug. 25, 2007  (GB) .................................. 0716621.8
Aug. 25, 2007  (GB) .................................. 0716622.6

(51) Int. Cl.
*A61K 31/28* (2006.01)
*A61K 31/295* (2006.01)
*A61K 31/30* (2006.01)
*A01N 55/00* (2006.01)
*A01N 55/02* (2006.01)

(52) U.S. Cl.
USPC ........... 514/492; 514/495; 514/499; 514/501; 514/502; 514/505; 502/159; 502/165; 502/167; 502/300

(58) Field of Classification Search
None
See application file for complete search history.

(56) References Cited

U.S. PATENT DOCUMENTS

| 4,072,784 | A | 2/1978 | Cirino | |
|---|---|---|---|---|
| 5,458,906 | A | 10/1995 | Liang | |
| 5,856,248 | A | 1/1999 | Weinberg | |
| 8,410,011 | B2 * | 4/2013 | Huddersman et al. | 502/159 |
| 2002/0010123 | A1 * | 1/2002 | Schmiedel et al. | 510/446 |
| 2005/0037057 | A1 * | 2/2005 | Schuette et al. | 424/443 |
| 2005/0226967 | A1 * | 10/2005 | Bringley et al. | 426/133 |
| 2008/0014278 | A1 * | 1/2008 | Lu et al. | 424/489 |
| 2008/0085326 | A1 * | 4/2008 | Ruan | 424/618 |

FOREIGN PATENT DOCUMENTS

| FR | 1499358 | 10/1967 |
|---|---|---|
| GB | 2346569 | 8/2000 |
| WO | WO 01/81671 | 11/2001 |
| WO | WO 2005/073289 A1 * | 8/2005 |
| WO | WO 2007/099293 | 9/2007 |

OTHER PUBLICATIONS

International Search Report (PCT/ISA/210) of PCT/GB2008/002864.

* cited by examiner

*Primary Examiner* — James H. Alstrum-Acevedo
(74) *Attorney, Agent, or Firm* — Foley & Lardner LLP

(57) ABSTRACT

The present invention provides a method of killing and/or inactivating microbes, the method comprising the step of placing the microbes in contact with a catalyst by means of a fluid medium, wherein the catalyst comprises a solid support, which solid support comprises one or more fibers, and a first metal cation fixed to the support. The fibers are keratinous fibers like wool fibers, or polyacrylonitrile (PAN) fibers. The first metal cation is selected from transition metal copper, silver and gold included. A second non-transition metal cation can be present. The catalyst is prepared by first treating the fibers with hydrazine and/or hydroxylamine salt in presence of a base, the modified fibers are then treated with an aqueous solution of containing the metal cations.

13 Claims, 1 Drawing Sheet

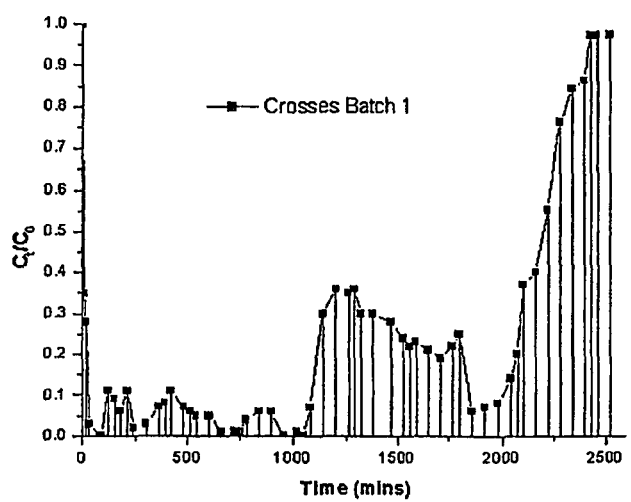

US 8,513,303 B2

ANTIMICROBIAL AGENT

The present invention relates to a method of killing and/or inactivating microbes (such as spores, bacteria, viruses, parasites, fungi and yeast) using a catalyst comprising a solid support, which solid support comprises one or more fibres, and a metal cation fixed to the support, to a method of disinfecting a substrate using the catalyst, to the use of the catalyst for killing and/or inactivating microbes and for disinfecting a substrate, and to a composition and an apparatus for killing and/or inactivating microbes comprising the catalyst.

Antimicrobial processes are desirable in both domestic and industrial situations, and are required in many fields such as the medical, veterinary, dental, chemical, pharmaceutical, agricultural, textile and water industries.

Certain antimicrobial agents are known. For example, peroxygen compounds (i.e. compounds containing an —O—O— group) such as hydrogen peroxide and peracetic acid have been shown to have antimicrobial activity against many different types of micro-organism, including Gram positive and Gram negative bacteria, protozoa, bacterial spores, mycobacteria, yeasts, fungi and viruses (see, for example, Block S. S. (2001) Peroxygen compounds in *Disinfection, Sterilization, and Preservation*, $5^{th}$ edition, ed Block, S. S., 185-204, Philadelphia: Lippincott, Williams and Wilkins; Bradley C. R., Babb J. R. and Ayliffe G. A. J. (1995) Evaluation of the Steris System 1 Peracetic Acid Endoscope Processor, *Journal of Hospital Infection*, 29, 143-151; Harakeh M. S. (1984) Inactivation of enteroviruses, rotaviruses and bacteriophages by peracetic acid in a municipal sewage effluent, *FEMS Microbiology Letters*, 23, 27-30; Holton J., Shetty N. and McDonald V. (1995) Efficacy of 'Nu-Cidex' (0.35% peracetic acid) against mycobacteria and cryptosporidia, *Journal of Hospital Infection*, 31, 235-244; Lauzardo M. and Rubin J. (2001) Mycobacterial disinfection in *Disinfection, Sterilization, and Preservation*, $5^{th}$ edition, ed Block S. S., 513-528, Philadelphia: Lippincott, Williams and Wilkins; Maillard J. Y. and Russell A. D. (1997) Viricidal activity and mechanisms of action of biocides, *Science Progress*, 80 (4), 287-315; Moore S. L. and Payne D. N. (2004) Types of antimicrobial agent in *Principles and Practice of Disinfection Preservation and Sterilization*, $4^{th}$ edition, eds Fraise A. P., Lambert P. A. and Maillard J. Y., 8-97, Oxford: Blackwell Publishing Ltd; and Russell A. D. (1998) Microbial susceptibility and resistance to chemical and physical agents in *Topley and Wilson's Microbiology and Microbial Infections, Volume 2: Systematic Bacteriology*, eds Balows A. and Duerden B. I., 149-184, London: Arnold). Hydrogen peroxide and peracetic acid have many applications including the disinfection of sewage and are widely used in the food processing and beverage industries (see, for example, Russell A. D. and Russell N. J. (1995) Biocides: activity, action and resistance in 50 *Years of Antimicrobials*, eds Hunter P. A., Darby G. K. and Russell N. J., Society for General Microbiology, Symposium 53. Cambridge University Press). The mechanism(s) of action of peroxygens against micro-organisms are thought to include oxidation, including free radical oxidation, of targets such as enzymes, protein thiol groups and DNA (see, for example, Block (2001) Peroxygen compounds in *Disinfection, Sterilization, and Preservation*, $5^{th}$ edition, ed Block, S. S., pages 185-204, Philadelphia: Lippincott, Williams and Wilkins; Denyer and Stewart, (1998): Mechanisms of action of disinfectants, *International Biodeterioration and Biodegradation*. 41, 261-268; and Moore and Payne (2004) Types of antimicrobial agent in *Principles and Practice of Disinfection Preservation and Sterilization*, $4^{th}$ edition, eds Fraise A. P., Lambert P. A. and Maillard J. Y., pages 8-97, Oxford: Blackwell Publishing Ltd).

U.S. Pat. No. 7,049,020 describes an ion conducting composite comprising a polymer, an acid-base component, a phyllosilicate and/or tectosilicate, where the polymer and the acid-base component may be combined. U.S. Pat. No. 7,049,020 teaches that the composites are intended for use in membrane fuel cells and that they exhibit decreased microbial attack by fungi and bacteria. There is no disclosure in U.S. Pat. No. 7,049,020 of a catalyst comprising a fibrous solid support.

The use of liquid formulations of iron and other transition metals in combination with hydrogen peroxide is known to result in an increase in antimicrobial activity. Ferric ions or cupric ions in combination with hydrogen peroxide have been shown to have activity against micro-organisms including *Escherichia coli, Staphylococcus aureus* and viruses (see, for example, Block S. S. (2001) Peroxygen compounds in *Disinfection, Sterilization, and Preservation*, $5^{th}$ edition, ed Block S. S., 185-204, Philadelphia: Lippincott, Williams and Wilkins; and Sagripanti J. L. (1992) Metal-based formulations with high microbicidal activity, *Applied and Environmental Microbiology*, 58(9), 3157-3162).

There remains a need however for alternative and preferably more efficient means and methods of killing and/or inactivating microbes and of disinfecting substrates.

BRIEF DESCRIPTION OF THE DRAWING

FIG. 1 shows the ratio between the substance's concentration at a given time t (Ct) and the initial concentration $C_0$ over different time points.

According to the present invention there is provided a method of killing and/or inactivating microbes, the method comprising the step of placing the microbes in contact with a catalyst by means of a fluid medium, wherein the catalyst comprises a solid support, which solid support comprises one or more fibres, and a metal cation fixed to the support. There is also provided the use of a catalyst for killing and/or inactivating microbes in contact with the catalyst by means of a fluid medium, wherein the catalyst comprises a solid support, which solid support comprises one or more fibres, and a metal cation fixed to the support. The method/use of the present invention may be used to kill and/or inactivate any microbe(s), wherein by microbes we mean any microscopic organism. For example, by the term "microbes", we include prions and microorganisms such as spores, bacteria, viruses, fungi, archaea and/or protists. Spores that may be killed and/or inactivated by the method/use of the present invention include *Bacillus subtilis* subsp. *Spizizenii, Bacillus cereus* and *Clostridium difficile*. Bacteria that may be killed and/or inactivated by the method/use of the present invention include Gram-positive and Gram-negative bacteria, such as *Escherichia coli, Pseudomonas aeruginosa, Staphylococcus aureus, Bacillus subtilis* (spores and vegetative cells) and *Mycobacteria*. Fungi that may be killed and/or inactivated by the method/use of the present invention include *Chytridiomycetes, Zygomycota, Ascomycota, Basidiomycota, Urediniomycetes, Ustilaginomycetes, Glomeromycota* and *Microsporidia* such as *Aspergillus flavus, Blastomyces dermatitidis* and *Candida albicans*. Archaea that may be killed and/or inactivated by the method/use of the present invention include euryarchaeota and crenarchaeota, such as *Thermococcus, Thermoplasma* and *Methanobacterium*. Protists that may be killed and/or inactivated by the method/use of the present invention include *Amoebozoa, Chromalveolata* and

*Excavata*, such as *Entamoeba, Acanthameoba, Giardia* and *Cryptosporidia*. Viruses that may be killed and/or inactivated by the method/use of the present invention include DNA viruses, RNA viruses, enveloped viruses, naked viruses and bacteriophage, such as herpes virus, influenza virus, human immunodeficiency virus and polio virus.

By the references herein to placing the microbes in contact with the catalyst by means of a fluid medium, we mean that the microbes are in contact with the fluid medium and the fluid medium is in contact with the catalyst, so that any active species generated by the catalyst (for example in the presence of an oxidant) are effective in killing and/or inactivating the microbes. This includes placing the catalyst and the microbes together in a fluid medium (i.e. such that the catalyst, including any active species generated by the catalyst, and the microbes are placed in contact with the fluid medium essentially simultaneously), as well as placing the catalyst in contact with a fluid medium (and, optionally, an oxidant) such that any active species generated by the catalyst are present in the fluid medium and then removing the catalyst from the fluid medium prior to contacting the microbes with the fluid medium (i.e. which fluid medium comprises any active species generated by the catalyst). The references to placing the microbes in contact with the catalyst by means of a fluid medium therefore include any such contact that enables any active species generated by the catalyst to kill and/or inactive the microbes. Without wishing to be bound by any theory, it is believed that the catalyst, when in contact with the fluid medium and optionally an oxidant, generates active catalytic species which kill and/or inactivate microbes that are located within an appropriate distance thereof.

As a person skilled in the art would appreciate, the microbes to be killed and/or inactivated by the method/use of the present invention may be present in or on any surface and in any environment. For example, the microbes may be present on or in the surface of a body part, cloth and/or instrument. In one aspect, the microbes may be present on a surface of a medical or surgical instrument, such as an endoscope. In another aspect, the microbes may be present on a surface for placing in an isolator apparatus, for example in which apparatus the method/use of the present invention may be conducted.

As a person skilled in the art would appreciate, the references to killing and/or inactivating do not necessarily mean that all of the microbes present initially are killed and/or inactivated. Preferably, according to the method/use of the present invention, the population of microbes is reduced to below detectable amounts (i.e. using standard detection techniques well known to persons skilled in the art). For example, according to the method/use of the present invention, the population of microbes may be reduced by at least about two logarithms, particularly by at least about three logarithms, more particularly by at least about four logarithms, even more particularly by about five logarithms over a suitable time period, such as a from 10 to 60 minutes.

Preferably, the catalyst is contacted with the microbes in the presence of an oxidant. Any suitable oxidant may be used in the method/use of the present invention. Suitable oxidants include peroxygen compounds, oxygen (such as atmospheric oxygen) and ozone, and mixtures thereof.

For example, the oxidant may be a peroxygen compound. Examples of peroxygen compounds suitable for use in the method/use of the present invention include hydrogen peroxide, hydrogen peroxide liberating compounds, hydrogen peroxide generating compounds, organic and inorganic peroxyacids and salts thereof, and mixtures thereof. For example, hydrogen peroxide liberating compounds include alkali metal peroxides, organic peroxide bleaching compounds such as urea peroxide and inorganic persalt bleaching compounds such as the alkali metal perborate, percarbonates, perphosphates and persulfates. Organic peroxyacids include compounds containing one or more peroxycarboxyl groups (i.e. —C(O)—O—OH), such as peracetic acid, performic acid and perpropionic acid. Further suitable oxidants include peroxyheptanoic acid, peroxynonanoic acid, perlauric acid, monoperglutaric acid, diperglutaric acid, succinylperoxide, derivatives of perbenzoic acid, magnesium salts of peroxyphthalate, peracid powders (for example made in situ by adding water to mixtures of organic acid reservoirs to hydrogen peroxide reservoirs such as sodium peroxide, benzoyl peroxide, t-butyl hydroperoxide), permanganates such as potassium permanganate, calcium peroxide and monoperoxy-sulfuric acid, and mixtures thereof. It is believed that the catalyst may provide a synergistic effect with a peroxygen compound (such as hydrogen peroxide) in the killing and/or inactivating of the microbes and result in greater activity against the microbes (including *Escherichia coli, Pseudomonas aeruginosa* and *Staphylococcus aureus*) than the use of a peroxygen compound, such as hydrogen peroxide, alone. In one aspect, the peroxygen compound may be selected from hydrogen peroxide, peracetic acid, and mixtures thereof, especially hydrogen peroxide.

The oxidant may be atmospheric oxygen. For example, the atmospheric oxygen may be dissolved in a liquid medium. The atmospheric oxygen may be used in the method/use as the only oxidant, or it may be used in combination with one or more suitable peroxygen compounds, for example as described above. It is believed that when the oxidant is provided by a peroxygen compound, such as hydrogen peroxide, in combination with atmospheric oxygen, then a greater activity against microbes, including *Escherichia coli, Pseudomonas aeruginosa* and *Staphylococcus aureus*, as well as *Bacillus subtilis* subsp. *spizizenii*, may be achieved compared to the use of a peroxygen compound, such as hydrogen peroxide, alone.

The catalyst may be contacted with the microbes in the presence of a source of ultra-violet radiation. The catalyst may be contacted with the microbes and optionally an oxidant in the presence of an electromagnetic field so as to produce a plasma gas.

The microbes are placed in contact with the catalyst by means of a fluid medium. The fluid medium may be liquid or gaseous. The references herein to liquids include gels, slurries and pastes. The references herein to gases include vapours.

As the skilled person would appreciate, any suitable fluid medium may be used. When the fluid medium is a liquid medium, any suitable liquid medium may be used. For example, the liquid medium may be polar. Preferably, the liquid medium is aqueous, for example comprising at least 40%, particularly at least 50%, by volume of water. For example the liquid medium may comprise water, such as distilled water. Such a liquid medium may comprise an oxidant (when present) dispersed or dissolved therein. When the fluid medium is a gaseous medium, any suitable gaseous medium may be used. For example, the gaseous medium may comprise atmospheric oxygen. The gaseous medium may, for example, comprise a vapour of an oxidant, such as a vapour of hydrogen peroxide and/or peracetic acid.

Without wishing to be bound by any theory, it is believed that upon contact with a fluid medium, such as a liquid medium, (and optionally an oxidant) an active species may be formed on the catalyst, which active species then may contact the microbes and act to kill and/or inactivate them. The catalyst may activate an oxidant (such as hydrogen peroxide) so as to generate an active species that acts to kill and/or inactivate the microbes. The references herein to placing the microbes in contact with a catalyst by means of a fluid medium, such as a liquid medium, include any suitable method by which this may be achieved. For example, the catalyst may be suspended in a liquid medium (for example as a particulate suspension), wherein the liquid medium includes the microbes to be killed and/or inactivated. This may be appropriate for example when the microbes are present in a liquid medium, such as in a liquid sample (including a slurry, gel or paste) to be treated. Alternatively, a liquid medium may be applied to a surface on which the microbes reside and the catalyst contacted with the surface (and therefore with the microbes in a liquid medium), for example by wiping the catalyst along the surface. Alternatively, a liquid medium may be applied to the catalyst, which catalyst including the liquid medium may then be contacted with the microbes, for example by wiping the catalyst including the liquid medium along a surface on which the microbes reside. As a person skilled in the art would appreciate, microbes may be present on any surface, for example such as on a surface of a medical or surgical instrument, such as an endoscope, or an internal surface of an isolator, or on a surface placed in an isolator.

A gaseous medium may be passed through and/or over the catalyst in an environment in which the microbes are contained, so as to contact the catalyst with the microbes by means of the gaseous medium.

In the method/use of the present invention, the catalysts may be used in multiple runs for killing and/or inactivating microbes. Thus, the method/use is advantageous because the catalyst maintains its activity for more than one run.

Typically, the method/use of the present invention may be conducted at any suitable pH, for example at a pH in the range of from 1 to 12, particularly of from 2 to 12, more particularly of from 3 to 8. The desired pH may be achieved by the addition of a suitable acid (such as hydrochloric or sulfuric acid), alkali (such as sodium hydroxide) or buffer (such as phosphate buffer) to the liquid medium in which the method is conducted. Typically, a liquid medium has a pH in the range of from 1 to 12, particularly of from 2 to 12, more particularly of from 3 to 8. Typically, the method/use of the present invention may be conducted at any suitable temperature. For example, in one aspect, the method/use may be conducted at a temperature in the range of from about 20 to 35° C. Improved anti-microbial activity may be achieved at temperatures of around 35° C., for example with a pH in the range of from about 3 to 8 (especially a pH of about 7).

The method/use of the present invention uses a catalyst comprising a solid support, which solid support comprises one or more fibres, and a suitable number of metal cations fixed to the support. As normally used in the art, by "a cation" is clearly meant a plurality of cations. Any suitable solid support may be used, provided that it is capable of having metal cations fixed thereto. For example, the solid support may be modified in an appropriate manner in order to enable the fixing of the metal cations thereto. As discussed below, the fixing of the metal cations to the solid support typically occurs by means of complexing of the metal cations to appropriate groups on the support.

The solid support comprises one or more fibres. For example, the solid support may comprise one or more fibres, which fibres are modified in order to enable the fixing or complexing of a metal cation thereto. The solid support may, for example, comprise one or more polyacrylonitrile (hereinafter referred to as "PAN") fibres, such as PAN fibres modified in an appropriate manner in order to enable the fixing of the metal cations thereto. Such a catalyst comprising a solid support that comprises one or more fibres, such as one or more PAN fibres, is known as a fibrous catalyst. Thus, the catalyst used in the method/use of the present invention may be a fibrous catalyst. For the avoidance of doubt, by the term "fibrous catalyst" we mean a catalyst that comprises polymer fibres to which catalytically active sites or centres are attached. By the term "fibres" we include both a single monofilament and a complex filament that is made up of more than one monofilament. The PAN fibres may be provided on a suitable carrier, such as a carrier comprised of one or more inert mono-fibres in addition to the PAN fibres.

In one aspect, the solid support may be a keratinous support, i.e. comprising one or more keratinous fibres. For example, the keratinous support may comprise one or more wool fibres. For example, the catalyst may comprise a solid keratinous support (such as a wool fibre) and a metal cation fixed to the support. Keratinous supports include supports derived from animal fleeces/hairs, such as wool, mohair, camel hair and so on.

The keratinous support may comprise wool (for example a wool fibre). As a skilled person would appreciate, wool is a fibrous material derived from the fleece or hair of animals, principally sheep. Wool fibres are in the form of monofilaments. A wool fibre may be bound, felted or spun into a yarn or thread, which yarn or thread may then be formed into a fabric or cloth, for example by knitting, weaving, sewing and/or needle punching. Thus a wool fibre of the solid support of the catalyst may take any suitable form, for example a wool fibre may be in the form of a yarn or thread and/or of a fabric or cloth. As the skilled person would appreciate, a plurality of wool fibres may be formed into a yarn or thread and a plurality of such yarns or threads may be formed into any such fabric or cloth. Any such fabric or cloth may additionally comprise an additional non-wool fibre, yarn and/or thread (such as polypropylene), which may for example be included by knitting, weaving, sewing and/or needle punching the non-wool fibre along with the wool yarn or thread. A keratinous support may be provided on a suitable carrier, such as a carrier comprised of an inert mesh (for example comprised of an inert metal and/or an inert plastics material such as nylon, polypropylene and/or polyester).

Wool fibres from any source may be used in the solid supports of the catalysts. For example, suitable wools include commercially available wools, such as wools from the Woolmark company and from the Thomas Chadwick and Sons company. Specific examples of wools that may be used include processed top wool (such as WOOLMARK 2 μm mean fibre diameter wool), top wool (such as supplied by DEFRA) and wools provided by Thomas Chadwick and Sons, such as Dark Grey Herdwick, Swaledale, Crosses and Blackface. The wool fibre may be a scoured wool fibre.

Catalysts comprising a keratinous support (such as a wool fibre) offer advantages in use because they are economical and convenient to prepare and use, for example because the keratinous support comprises materials (such as wool fibres) that are readily available, cheap and safe to use. Materials such as wool fibres are available naturally, without substantial manufacturing and/or processing prior to their use in the catalyst support.

The catalyst may comprise any suitable metal cation(s) fixed to the solid support. Suitable metal cations may be selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum, gold, zinc and aluminium cation, and mixtures thereof.

In one aspect, suitable metal cations may be selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation, and mixtures thereof. As the skilled person would appreciate such metal cations are cations of transition metals, for example those elements that have partly filled d shells as elements and/or in compounds.

In one aspect of the invention, the metal cation may be selected from a scandium, titanium, vanadium, chromium, manganese, iron, cobalt, nickel, copper, yttrium, zirconium, niobium, molybdenum, technetium, ruthenium, rhodium, silver, hafnium, tantalum, tungsten, rhenium, osmium, iridium, platinum and gold cation, and mixtures thereof. In another aspect, the metal cation may be selected from a scandium, titanium, vanadium, chromium, manganese, iron, cobalt, nickel and copper cation, and mixtures thereof. In another aspect, the first metal cation may be selected from a titanium, chromium, manganese, iron, cobalt, nickel and copper cation (particularly a chromium, manganese, iron, cobalt, nickel and copper cation), and mixtures thereof.

In another aspect, the metal cation may be selected from an iron (for example $Fe^{2+}$ or $Fe^{3+}$) and copper (for example $Cu^{2+}$) cation, and mixtures thereof. In another aspect, the metal cation may be selected from an iron (for example $Fe^{2+}$ or $Fe^{3+}$, especially $Fe^{3+}$) and a nickel cation (for example $Ni^{2+}$), and mixtures thereof. In yet another aspect, the metal cation may be an iron cation (for example $Fe^{2+}$ or $Fe^{3+}$, especially $Fe^{3+}$). Iron cations are advantageous because iron is non-toxic and is easily disposed of after use.

In one aspect, the catalyst may comprise one or more additional metal cations fixed to the solid support in addition to the transition metal cations listed above. Such an additional metal cation may be selected from a zinc or aluminium cation, and mixtures thereof.

The catalyst may, for example, comprise a keratinous support and a metal cation fixed to the keratinous support, which metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum, gold, zinc or aluminium cation, and mixtures thereof and wherein the metal cation preferably is present in an amount of 0.03 mmol or greater per gram of keratinous support. For example, the metal cation may be present in an amount of from 0.03 to 1.0 mmol per gram of keratinous support, such as in an amount of from 0.03 to 0.5 mmol per gram of keratinous support, more particularly of from 0.03 to 0.1 mmol per gram of keratinous support, even more particularly of from 0.07 to 0.1 mmol per gram of keratinous support.

The catalyst may, for example, comprise a keratinous support and a metal cation fixed to the keratinous support, which metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation, and mixtures thereof and wherein the metal cation preferably is present in an amount of 0.03 mmol or greater per gram of keratinous support. For example, the metal cation may be present in an amount of from 0.03 to 1.0 mmol per gram of keratinous support, such as in an amount of from 0.03 to 0.5 mmol per gram of keratinous support, more particularly of from 0.03 to 0.1 mmol per gram of keratinous support, even more particularly of from 0.07 to 0.1 mmol per gram of keratinous support.

The catalyst may, for example, comprise a wool fibre and a metal cation fixed to the wool fibre, which metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum, gold, zinc and aluminium cation, and mixtures thereof and wherein the metal cation preferably is present in an amount of 0.03 mmol or greater per gram of wool fibre. For example, the first metal cation may be present in an amount of from 0.03 to 1.0 mmol per gram of wool fibre, such as in an amount of from 0.03 to 0.5 mmol per gram of wool fibre, more particularly of from 0.03 to 0.1 mmol per gram of wool fibre, even more particularly of from 0.07 to 0.1 mmol per gram of wool fibre.

The catalyst may, for example, comprise a wool fibre and a metal cation fixed to the wool fibre, which metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation, and mixtures thereof and wherein the metal cation preferably is present in an amount of 0.03 mmol or greater per gram of wool fibre. For example, the first metal cation may be present in an amount of from 0.03 to 1.0 mmol per gram of wool fibre, such as in an amount of from 0.03 to 0.5 mmol per gram of wool fibre, more particularly of from 0.03 to 0.1 mmol per gram of wool fibre, even more particularly of from 0.07 to 0.1 mmol per gram of wool fibre.

The method of the present invention may comprise the step of placing the catalyst in a suitable fluid medium, wherein the fluid medium comprises the microbes dispersed therein and optionally comprises an oxidant, so as to place the microbes in contact with the catalyst (and any active species generated by the catalyst).

The method of the present invention may comprise the steps of:
(a) dispersing the microbes in a suitable fluid medium (the fluid medium optionally comprising an oxidant);
(b) placing the catalyst in a suitable fluid medium (the fluid medium optionally comprising an oxidant); and
(c) combining the fluid media from steps (a) and (b) so as to place the microbes in contact with the catalyst (and any active species generated by the catalyst).

The method of the present invention may comprise the steps of:
(a) dispersing the microbes in a suitable fluid medium;
(b) optionally adding an oxidant to the fluid medium; and
(c) placing the catalyst in the fluid medium so as to place the microbes in contact with the catalyst (and any active species generated by the catalyst).

The method of the present invention may comprise the steps of:
(a) placing the catalyst in a suitable fluid medium (the fluid medium optionally comprising an oxidant), such that active species are generated by the catalyst and dispersed in the fluid medium;
(b) removing the catalyst from the fluid medium (i.e. so as to provide a fluid medium comprising the active species generated by the catalyst and optionally an oxidant); and then (c) contacting the fluid medium (i.e. comprising the active species) with the microbes, so as to kill and/or inactivate the microbes.

The method of the present invention may further comprise the step of manufacturing the catalyst prior to the step of placing the microbes in contact with the catalyst. The catalyst may be manufactured by any suitable method. For example, the catalyst may be prepared as described in WO-2007/099293, GB-A-2,346,569, GB-A-1,436,245, RU-A-2118908, RU-2266304, V. V. Ishtchenko et al., Applied Catalysis A: General 242 (2003), 123-137, or R. F. Vitkovskaya et al., Fibre Chemistry, 35(3) (2003), 202-207.

For example, a fibrous catalyst wherein the solid support comprises one or more PAN fibres may be manufactured (prior to the step of placing the microbes in contact with the catalyst) according to the steps of:

(i) treating the one or more PAN fibres with a hydrazine salt and a hydroxylamine salt in the presence of a base to provide modified PAN fibres;

(ii) treating the modified PAN fibres with a base; and (iii) treating the modified PAN fibres with an aqueous solution comprising a salt of a first metal cation and a salt of a second metal cation, which first metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation, and mixtures thereof, and which second metal cation is selected from a lithium, sodium, potassium, rubidium, cesium, beryllium, magnesium, calcium, strontium, barium, zinc, cadmium, mercury, aluminium, gallium, indium, thallium, tin, lead, antimony and bismuth cation, and mixtures thereof.

A fibrous catalyst wherein the solid support comprises one or more PAN fibres may, for example, be manufactured (prior to the step of placing the microbes in contact with the catalyst) according to the steps of:

(i) treating one or more PAN fibres with a hydrazine salt and a hydroxylamine salt in the presence of a base to provide modified PAN fibres;

(ii) treating the modified PAN fibres with a base; and (iii) treating the modified PAN fibres with an aqueous solution comprising a sulfate salt of a first metal cation and a salt of a second metal cation, wherein the first metal cation is selected from an iron and nickel cation, and mixtures thereof, and wherein the second metal cation is selected from a lithium, sodium, potassium, rubidium, cesium, beryllium, magnesium, calcium, strontium, barium, zinc, cadmium, mercury, aluminium, gallium, indium, thallium, tin, lead, antimony and bismuth cation, and mixtures thereof.

A fibrous catalyst wherein the solid support comprises one or more PAN fibres may, for example, be manufactured (prior to the step of placing the microbes in contact with the catalyst) according to the steps of:

(i) treating one or more PAN fibres with a hydrazine salt and a hydroxylamine salt in the presence of a base to provide modified. PAN fibres;

(ii) treating the modified PAN fibres with a base; and (iii) treating the modified PAN fibres with an aqueous solution comprising a sulfate salt of an iron cation (such as $Fe_2(SO_4)_3$ and/or $FeSO_4.xH_2O$, wherein x is 0, 1, 4, 5 or 7) and a salt of a second metal cation, wherein the second metal cation is selected from a lithium, sodium, potassium, rubidium, cesium, beryllium, magnesium, calcium, strontium, barium, zinc, cadmium, mercury, aluminium, gallium, indium, thallium, tin, lead, antimony and bismuth cation, and mixtures thereof.

A fibrous catalyst wherein the solid support comprises one or more PAN fibres may, for example, be manufactured (prior to the step of placing the microbes in contact with the catalyst) according to the steps of:

(i) treating one or more PAN fibres with a hydrazine salt and a hydroxylamine salt in the presence of a base to provide modified PAN fibres;

(ii) treating the modified PAN fibres with a base; and (iii) treating the modified PAN fibres with an aqueous solution comprising a sulfate salt of a nickel cation (such as $NiSO_4$) and a salt of a second metal cation, wherein the second metal cation is selected from a lithium, sodium, potassium, rubidium, cesium, beryllium, magnesium, calcium, strontium, barium, zinc, cadmium, mercury, aluminium, gallium, indium, thallium, tin, lead, antimony and bismuth cation, and mixtures thereof.

A fibrous catalyst wherein the solid support comprises one or more PAN fibres may, for example, be manufactured (prior to the step of placing the microbes in contact with the catalyst) according to the steps of:

(i) treating one or more PAN fibres with a hydrazine salt and a hydroxylamine salt in the presence of a base to provide modified PAN fibres;

(ii) treating the modified PAN fibres with a base; and (iii) treating the modified PAN fibres with an aqueous solution comprising a sulfate salt of a copper cation (such as $CuSO_4.5H_2O$ and/or $CuSO_4.H_2O$) and a salt of a second metal cation, wherein the second metal cation is selected from a lithium, sodium, potassium, rubidium, cesium, beryllium, magnesium, calcium, strontium, barium, zinc, cadmium, mercury, aluminium, gallium, indium, thallium, tin, lead, antimony and bismuth cation, and mixtures thereof.

As the skilled person would appreciate, the second metal cations listed in the methods of manufacturing a fibrous catalyst are all cations of the metals belonging to Groups 1, 2, 12, 13, 14 and 15 as set out in the Periodic Table of Elements (according to established IUPAC nomenclature).

In step (i) of the manufacture of the fibrous catalyst, the PAN fibre is "modified". This modification is believed to be a result of several reactions that occur between the nitrile groups of the PAN fibres and the reagents used in step (i). For example, it is believed that the nitrile groups of the PAN fibres are converted into functional groups that are able to form complexes at least with the first metal (i.e. the transition metal) cations. For example, it is believed that some of the nitrile groups of the PAN fibres react with the hydrazine salt so as to produce amino and amido groups and that some of the nitrile groups are hydrolysed so as to produce carboxyl groups. Thus, a cross-linked, amino-amido-carboxyl ion-exchange material is formed which is able to absorb first metal (i.e. transition metal) cations to form complexes at least with the first metal (i.e. transition metal) cations, which complexes act as catalytic active sites. Additionally, it is believed that some of the nitrite groups of the PAN fibres react with the hydroxylamine salt to produce amidoxime groups, which amidoxime groups are then hydrolysed to form products having a complex structure including carboxyl and hydroxylamine acid groups as well as glutarimine and other cyclic groups.

As the skilled person would appreciate, any suitable hydrazine salt may be used in step (i) of the methods of manufacturing a fibrous catalyst. For example, in one aspect particularly suitable hydrazine salts include hydrazine dihydrochloride, hydrazine monohydrochloride, hydrazine hydrate, hydrazine monohydrobromide, hydrazine acetate, hydrazine sulfate and dihydrazine sulfate, and mixtures thereof, especially hydrazine sulfate and dihydrazine sulfate, and mixtures thereof, even more especially dihydrazine sulfate. In another aspect, suitable hydrazine salts include hydrazine dihydrochloride, hydrazine monohydrochloride, hydrazine monohydrobromide, hydrazine acetate and hydrazine sulfate, and mixtures thereof (particularly hydrazine dihydrochloride). As the skilled person would appreciate, one or more hydrazine salts may be used in step (i), as appropriate.

As the skilled person would appreciate, any suitable hydroxylamine salt may be used in step (i) of the methods of manufacturing a fibrous catalyst. For example, suitable hydroxylamine salts include hydroxylamine monohydrochloride, hydroxylamine sulfate and hydroxylamine phosphate, and mixtures thereof. In particular, the hydroxylaime salt may be hydroxylamine sulfate. As the skilled person would appreciate, one or more hydroxylamine salts may be used in step (i), as appropriate.

In particular, in step (i) of the methods of manufacturing a fibrous catalyst, the hydrazine salt may be selected from hydrazine sulfate and dihydrazine sulfate, and mixtures thereof, and the hydroxylamine salt may be hydroxylamine sulfate. For example, in one aspect, the hydrazine salt may be dihydrazine sulfate and the hydroxylamine salt may be hydroxylamine sulfate.

In step (i) of the methods of manufacturing a fibrous catalyst, salts of hydrazines containing from one to four substituents may be used, which substituents may be the same or different and selected from (1-4C)alkyl, aryl (such as phenyl) and (1-4C)alkanoyl and which substituents may be further substituted for example by one or more further substituents which may be the same or different selected from halogen, nitro and hydroxyl. Salts of hydroxylamines containing one or two substituents may be used, which substituents may be the same or different and selected from (1-4C)alkyl, aryl (such as phenyl) and (1-4C)alkanoyl and which substituents may be further substituted for example by one or more further substituents which may be the same or different selected from halogen, nitro and hydroxyl. Thus, references herein to hydrazine salts include references to salts of hydrazine (i.e. $N_2H_4$) itself as well as salts of derivatives of hydrazine, i.e. which derivatives include substituents as discussed above on the nitrogen atom(s) of the hydrazine (i.e. in place of hydrogen atom(s)). Similarly, references herein to hydroxylamine salts include references to salts of hydroxylamine (i.e. $NH_2OH$) itself as well as salts of derivatives of hydroxylamine, i.e. which derivatives include substituents as discussed above on the nitrogen and/or oxygen atom(s) of the hydroxylamine (i.e. in place of hydrogen atom(s)). Preferably, however, the hydrazine and hydroxylamine salts include no such substituents.

In step (i) of the methods of manufacturing a fibrous catalyst, the PAN fibres may be treated with a solution of a hydrazine salt and a hydroxylamine salt (for example as described above) in a suitable solvent and in the presence of a suitable base. Typically, an aqueous solution of the hydrazine salt and the hydroxylamine salt is used. The concentration of the hydrazine salt used in step (i) may be in the range of from 10 to 50 g/l, particularly in the range of from 20 to 40 g/l, more particularly about 30 g/l. The concentration of the hydroxylamine salt used in step (i) may be in the range of from 14 to 70 g/l, particularly in the range of from 30 to 55 g/l, more particularly about 42 g/l. Typically, the hydrazine salt and hydroxylamine salt may be present in the solution in a molar ratio in the range of from about 1:1 to about 1:3, preferably of about 1:2.

Typically, in step (i) of the methods of manufacturing a fibrous catalyst, the weight ratio of PAN fibres to total hydroxylamine salt may be in the range of from about 1:8 to 1:0.5, preferably in the range of from about 1:6 to about 1:2, more preferably in the range of from about 1:4 to about 1:2, even more preferably of about 1:2.7. The weight ratio of PAN fibres to total hydrazine salt may be in the range of from about 1:7 to 1:0.15, preferably in the range of from about 1:4 to about 1:1, more preferably in the range of from about 1:3 to about 1:1.5, even more preferably of about 1:1.9.

Any suitable base may be used in step (i) of the methods of manufacturing a fibrous catalyst. For example, a suitable base may be selected from sodium hydroxide, potassium hydroxide and sodium carbonate, and mixtures thereof (particularly sodium hydroxide). The base is used in step (i) to maintain a suitable pH, i.e. at which modification of the PAN fibre(s) may occur. A suitable pH is, for example, a pH in the range of from 6.5 to 12, particularly a pH in the range of from 8.5 to 11 and more particularly a pH of about 9.5.

The step (i) of the methods of manufacturing a fibrous catalyst may conveniently be conducted at a temperature of greater than 60° C., particularly at a temperature of greater than 80° C., more particularly at a temperature in the range of from 95 to 180° C., even more particularly at a temperature in the range of from 95 to 105° C., for example at a temperature of about 98 to 102° C.

The reaction of step (i) of the methods of manufacturing a fibrous catalyst may be monitored by any suitable means, such as by infra-red spectroscopy. For example, the reduction in the intensity of or the disappearance of the nitrile peak may be monitored by infra-red spectroscopy. A typical treatment time is from about 30 minutes to 3 hours, suitably about 2 hours. Typically, at least 60% of the PAN fibres are modified after reaction for about two hours under the reaction conditions discussed above for step (i).

In step (ii) of the methods of manufacturing a fibrous catalyst, the modified PAN fibre produced in step (i) is treated with an additional base prior to conducting step (iii). It is believed that step (ii) converts those nitrile groups that remain after step (i) into carboxyl groups, which carboxyl groups are able to absorb first metal (i.e. transition metal) cations to form complexes with the first metal (i.e. transition metal) cations. In other words, the PAN fibre is further modified in step (ii). Thus, references herein to "modified PAN fibre" are intended to refer to modified PAN fibre, i.e. wherein the PAN fibre has been subjected to steps (i) and/or (ii) (suitably steps (i) and (ii)) of the methods of manufacturing a fibrous catalyst.

As the skilled person would appreciate, any suitable base may be used in step (ii) of the methods of manufacturing a fibrous catalyst. For example, a suitable base may be selected from sodium hydroxide, potassium hydroxide and sodium carbonate, and mixtures thereof (such as a sodium hydroxide solution with a concentration in the range of from 10 to 100 g/l, particularly of from 50 to 100 g/l, more particularly of from 20 to 40 g/l). The same or different base may be used in steps (i) and (ii) of the methods of manufacturing a fibrous catalyst. The base may be used in the form of a solution, for example an aqueous solution.

The base is used in step (ii) of the methods of manufacturing a fibrous catalyst to maintain a suitable pH, i.e. at which further modification of the PAN fibre may occur. A suitable pH is, for example, a pH in the range of from 6.5 to 14, particularly a pH of from 8 to 14. Suitable treatment times for step (ii) may be in the range of from 30 seconds to 60 minutes, particularly in the range of from 30 seconds to 30 minutes, such as in the range of from 30 seconds to 15 minutes, for example in the range of from 5 minutes to 15 minutes. The step (ii) of the methods of manufacturing a fibrous catalyst may conveniently be conducted at a temperature of greater than ambient temperature, particularly at a temperature in the range of from 25 to 130° C., more particularly at a temperature in the range of from 50 to 110° C., for example at a temperature of about 60° C.

In step (iii) of the methods of manufacturing a fibrous catalyst, the modified PAN fibre produced in step (ii) is treated with an aqueous solution so as to provide the fibrous catalyst. The aqueous solution typically is an aqueous metal salt solution. The aqueous solution comprises a salt of a first metal (i.e. transition metal) cation and a salt of a second metal cation, as defined above. As the skilled person would appreciate, the aqueous solution may, in one aspect, comprise only one salt of a first metal (i.e. transition metal) cation. However, in another aspect, the aqueous solution may comprise more than one salt of a first metal (i.e. transition metal) cation. In other words, the aqueous metal salt solution may comprise a mixture of first metal (i.e. transition metal) salts. Similarly, the aqueous solution may comprise only one salt of a second metal cation or may comprise a mixture of second metal salts.

Without wishing to be bound by any theory, the first metal (i.e. transition metal) cation is believed to form a complex with suitable functional groups on the modified PAN fibre as discussed above. The method of manufacturing a fibrous catalyst, therefore, provides a fibrous catalyst that comprises a suitable number of at least one first metal (i.e. transition metal) cations fixed to PAN fibres (i.e. wherein the PAN fibres provide the solid support of the catalyst).

As the skilled person would appreciate, the salts of the first metal (i.e. transition metal) cation(s) (when not specifically defined) used in step (iii) of the methods of manufacturing a fibrous catalyst may comprise any suitable anion. Suitable anions include, for example, chlorides, iodides, bromides, fluorides, sulfates, carboxylates, thiosulfates, thiocyanates, perchlorates, nitrates and nitrites, particularly chlorides, sulfates, nitrates and nitrites, more particularly chlorides and sulfates, and mixtures thereof. Thus, examples of suitable transition metal salts include $FeCl_3.6H_2O$, $FeSO_4.H_2O$, $Fe_2(SO_4)_3.7H_2O$, $CuCl_2.2H_2O$ and/or $CuSO_4.5H_2O$, especially $FeCl_3.6H_2O$, $FeSO_4.H_2O$ and/or $Fe_2(SO_4)_3.7H_2O$.

In one aspect, the second metal cation used in step (iii) of the methods of manufacturing a fibrous catalyst is selected from a lithium ($Li^+$, magnesium ($Mg^{2+}$), calcium ($Ca^{2+}$) and zinc ($Zn^{2+}$) cation, and mixtures thereof. In another aspect, in step (iii) of the methods of manufacturing a fibrous catalyst the second metal cation is selected from a lithium, sodium, potassium, rubidium, cesium, beryllium, magnesium, calcium, strontium, barium, zinc, cadmium, mercury, aluminium, gallium, indium, thallium, tin, lead, antimony and bismuth cation, and mixtures thereof. In another aspect, in step (iii) of the methods of manufacturing a fibrous catalyst, the second metal cation is selected from a sodium, lithium, potassium, calcium, magnesium and zinc cation, and mixtures thereof, especially selected from a sodium, potassium and calcium cation, and mixtures thereof, even more especially selected from a sodium and potassium cation, and mixtures thereof. In one aspect, in step (iii) of the methods of manufacturing a fibrous catalyst, the second metal cation is a calcium cation. In another aspect, in step (iii) of the methods of manufacturing a fibrous catalyst, the second metal cation is a sodium cation. As the skilled person would appreciate, in step (iii) of the methods of manufacturing a fibrous catalyst the aqueous solution may comprise only one salt of a second metal cation or may comprise a mixture of second metal cation salts.

Without wishing to be bound by any theory, it is believed that the second metal cations act as facilitators to fix or complex the first metal (i.e. transition metal) cations to the modified PAN fibres. Typically, the second metal cations are not believed to fix to the modified PAN fibres. However, in some cases, the second metal cation(s) may fix or complex to the modified PAN fibres. For example when the second metal cation is a zinc and/or aluminium cation, it is believed that the zinc and/or aluminium cation may fix or complex to the modified PAN fibres.

As the skilled person would appreciate, in step (iii) of the methods of manufacturing a fibrous catalyst, the salts of the second metal cation(s) may comprise any suitable anion. Suitable anions include, for example, chlorides, iodides, bromides, fluorides, sulfates, hydrogen sulphates, carboxylates, thiosulfates, thiocyanates, perchlorates, nitrates and nitrites, particularly chlorides, sulfates, nitrates and nitrites, more particularly nitrates and sulfates, and mixtures thereof. Further examples of suitable anions include chlorides, sulfates, nitrates and nitrites, particularly chlorides, sulfates and nitrates, even more particularly chlorides and sulfates, and mixtures thereof. Examples of suitable second metal salts for use in step (iii) of the methods of manufacturing a fibrous catalyst include $Ca(NO_3)_2.4H_2O$, $CaSO_4.0.5H_2O$, $CaSO_4.2H_2O$, $CaCl_2$, $CaCl_2.2H_2O$, $CaCl_2.6H_2O$, $Mg(NO_3)_2.6H_2O$, $MgCl_2.6H_2O$, $MgSO_4.7H_2O$, $Li_2SO_4.H_2O$, $ZnSO_4.7H_2O$, $NaCl$, $Na_2SO_4$, $Na_2SO_4.10H_2O$ $KCl$, $K_2SO_4$, $LiCl$, $NaNO_3$, $LiNO_3$, $KNO_3$ and/or $Li_2SO_4$, particularly $Ca(NO_3)_2.4H_2O$, $CaSO_4.0.5H_2O$, $CaSO_4.2H_2O$, $CaCl_2$, $CaCl_2.2H_2O$, $CaCl_2.6H_2O$, $Mg(NO_3)_2.6H_2O$, $MgCl_2.6H_2O$, $MgSO_4.7H_2O$, $Li_2SO_4.H_2O$, $ZnSO_4.7H_2O$, $NaCl$, $Na_2SO_4$, $Na_2SO_4.10H_2O$ $NaNO_3$, $KCl$, $K_2SO_4$ and/or $KNO_3$, more particularly $Ca(NO_3)_2.4H_2O$.

In one particular aspect, in step (iii) of the methods of manufacturing a fibrous catalyst, the salt of the second metal cation may be a sulfate salt. For example, the salt of the second metal cation may be a sulfate salt of sodium, potassium and/or calcium (especially sodium), such as $CaSO_4.0.5H_2O$, $CaSO_4.2H_2O$, $Na_2SO_4$, $Na_2SO_4.10H_2O$ and/or $K_2SO_4$. In another particular aspect, in step (iii) of the methods of manufacturing a fibrous catalyst, the salt of the second metal cation may be a chloride salt. For example, the salt of the second metal cation may be a chloride salt of sodium, potassium and/or calcium (especially sodium), such as $CaCl_2.2H_2O$, $CaCl_2.6H_2O$, $NaCl$ and/or $KCl$. In another particular aspect, the salt of the second metal cation may be a nitrate salt. For example, the salt of the second metal cation may be a nitrate salt of sodium, lithium, potassium and/or calcium (especially sodium), such as $Ca(NO_3)_2.4H_2O$, $NaNO_3$, $LiNO_3$ and/or $KNO_3$. In particular, the salt of the second metal cation may be a salt selected from sodium chloride (NaCl), calcium nitrate tetrahydrate ($Ca(NO_3)_2.4H_2O$) and sodium sulfate ($Na_2SO_4$ and/or $Na_2SO_4.10H_2O$), and mixtures thereof. More particularly, in step (iii) of the methods of manufacturing a fibrous catalyst, the salt of the second metal cation may be a salt selected from sodium chloride (NaCl) and sodium sulfate ($Na_2SO_4$ and/or $Na_2SO_4.10H_2O$), and mixtures thereof.

The total metal cation concentration in the aqueous solution in step (iii) of the methods of manufacturing a fibrous catalyst may be in the range of from 0.05 g/L to 500 g/L, such as in the range of from 5 g/L to 100 g/L. In the aqueous solution, the molar ratio of the salt of the first metal cation (such as an iron and/or nickel sulfate salt) to the second metal salt may be in the range of from 1:1 to 1:12, particularly in the range of from 1:1 to 1:9, more particularly in the range of from 1:2 to 1:6, even more particularly in the range of from 1:3 to 1:6.

The step (iii) of the methods of manufacturing a fibrous catalyst may conveniently be conducted at a temperature in the range of from 5 to 80° C., preferably at ambient temperature, i.e. a temperature in the range of from 10 to 30° C., particularly in the range of from 20 to 30° C., for example about 25° C. The step (iii) of the methods of manufacturing a fibrous catalyst may conveniently be conducted at a pH in the range of from 1 to 7, particularly at a pH in the range of from 2 to 4, more particularly at a pH in the range of from 2 to 3.

The reaction of step (iii) of the methods of manufacturing a fibrous catalyst may be monitored by any suitable means, for example by atomic absorption spectroscopy. For example, the uptake of first metal (i.e. transition metal) cation by the modified PAN fibres may be monitored by atomic absorption spectroscopy. Typically, the reaction of step (iii) is complete after about 2 to 4 hours under the reaction conditions discussed above for step (iii). A typical treatment time for step (iii) is from about 30 minutes to 18 hours, particularly from about 1 hour to 6 hours, more particularly from about 2 hours to 3 hours, even more particularly about 2 hours.

Typically, the PAN fibre is washed between each of the steps (i) to (iii) of the methods of manufacturing a fibrous catalyst. For example, the fabric may be washed with water, for example with distilled water. The washing step substantially removes residual reagents present from the previous reaction step(s). Typically, after step (iii) of the methods of manufacturing a fibrous catalyst, the fibrous catalyst is dried before use. The catalyst may be dried using any conventional means, for example at temperatures up to 105° C.

The one or more PAN fibres used in the methods of manufacturing a fibrous catalyst may be used in the form of a fabric, for example in the form of a knitted fabric, such as a fibrous knitted mesh. In this aspect, the PAN fibres must be capable of being knitted. Such a knitted fabric may be prepared by any suitable method known in the art. For example, the fabric may be knitted using conventional equipment using the "polufang" (half-cardigan structure) knitting method, which method is identifiable by British Standard 5441:1998 and would be well known to a person skilled in the art. The PAN fibres may be complex PAN fibres and may be prepared by any suitable method known to a person skilled in the art. For example, the PAN fibres may be prepared according to Russian Standard 6-0602-80.

When in the form of a fabric, the fabric may comprise one or more inert mono-fibres in addition to the PAN fibres. The inert mono-fibres preferably should be capable of being knitted and act as a carrier or support for the PAN fibres, so as to provide a fibrous catalyst that is self-supporting. The inert mono-fibres may be any suitable fibres known to a person skilled in the art. For example, suitable inert mono-fibres include polypropylene fibres (such as polypropylene fibres made according to Russian Standard 6-06-537-87).

When a knitted fabric comprises one or more inert mono-fibres, any suitable weight ratio of PAN fibres to inert mono-fibres may be used. It is preferred that a knitted fabric comprises a higher proportion of PAN fibres than inert mono-fibres. For example, a knitted fabric may comprise PAN fibres and inert mono-fibres in a weight ratio in the range of from 90:10 to 10:90, particularly 75:25 to 25:75 and more particularly 60:40 to 40:60.

A fibrous catalyst wherein the solid support comprises one or more PAN fibres may, for example, be manufactured (prior to the step of placing the microbes in contact with the catalyst) according to the steps of:

(i) treating a fabric comprising PAN fibres with a hydrazine salt selected from hydrazine sulfate and dihydrazine sulfate (especially dihydrazine sulfate) and hydroxylamine sulfate in the presence of a base to provide a modified fabric;

(ii) treating the modified fabric with a base; and (iii) treating the modified fabric with an aqueous solution comprising a sulfate salt of an iron cation and a salt (especially a sulfate and/or chloride salt) of a second metal cation, wherein the second metal cation is selected from a lithium, sodium, potassium, magnesium, calcium and zinc cation, and mixtures thereof.

A fibrous catalyst wherein the solid support comprises one or more PAN fibres may, for example, be manufactured (prior to the step of placing the microbes in contact with the catalyst) according to the steps of:

(i) treating a fabric comprising PAN fibres with a hydrazine salt selected from hydrazine sulfate and dihydrazine sulfate (especially dihydrazine sulfate) and hydroxylamine sulfate in the presence of a base to provide a modified fabric;

(ii) treating the modified fabric with a base; and (iii) treating the modified fabric with an aqueous solution comprising a sulfate salt of a nickel cation and a salt (especially a sulfate and/or chloride salt) of a second metal cation, wherein the second metal cation is selected from a lithium, sodium, potassium, magnesium, calcium and zinc cation, and mixtures thereof.

A fibrous catalyst wherein the solid support comprises one or more PAN fibres may, for example, be manufactured (prior to the step of placing the microbes in contact with the catalyst) according to the steps of:

(i) treating a fabric comprising PAN fibres with a hydrazine salt selected from hydrazine sulfate and dihydrazine sulfate (especially dihydrazine sulfate) and hydroxylamine sulfate in the presence of a base to provide a modified fabric;

(ii) treating the modified fabric with a base; and (iii) treating the modified fabric with an aqueous solution comprising a sulfate salt of an iron cation and a sulfate and/or chloride salt of a second metal cation, wherein the second metal cation is selected from a lithium, sodium and calcium cation, and mixtures thereof (especially the second metal cation may be sodium).

A fibrous catalyst wherein the solid support comprises one or more PAN fibres may, for example, be manufactured (prior to the step of placing the microbes in contact with the catalyst) according to the steps of:

(i) treating a fabric comprising PAN fibres with a hydrazine salt selected from hydrazine sulfate and dihydrazine sulfate (especially dihydrazine sulfate) and hydroxylamine sulfate in the presence of a base to provide a modified fabric;

(ii) treating the modified fabric with a base; and (iii) treating the modified fabric with an aqueous solution comprising a sulfate salt of a nickel cation and a sulfate and/or chloride salt of a second metal cation, wherein the second metal cation is selected from a lithium, sodium and calcium cation, and mixtures thereof (especially the second metal cation may be sodium).

A fibrous catalyst wherein the solid support comprises one or more PAN fibres may, for example, be manufactured (prior to the step of placing the microbes in contact with the catalyst) according to the steps of:

(i) treating the one or more PAN fibres with a hydrazine salt and a hydroxylamine salt in the presence of a base to provide modified PAN fibres;

(ii) treating the modified PAN fibres with a base; and (iii) treating the modified PAN fibres with an aqueous solution comprising a salt of a second metal cation, which second metal cation is selected from a zinc and aluminium cation, and mixtures thereof. In this method, the reaction conditions, reagent amounts and so on may be as described above in relation to the manufacture of a fibrous catalyst wherein the solid support comprises one or more PAN fibres, except that only a second metal cation selected from a zinc and aluminium cation, and mixtures thereof is included in the aqueous metal salt solution.

A fibrous catalyst wherein the solid support comprises one or more PAN fibres may, for example, be manufactured (prior to the step of placing the microbes in contact with the catalyst) according to the steps of:
(i) treating a fabric comprising PAN fibres with a hydrazine salt (for example selected from hydrazine sulfate, dihydrazine sulfate, hydrazine monochloride and/or hydrazine dihydrochloride, especially selected from hydrazine dihydrochloride and/or dihydrazine sulfate) and a hydroxylamine salt (for example selected from hydroxylamine monohydrochloride and/or hydroxylamine sulfate) in the presence of a base to provide a modified fabric;
(ii) treating the modified fabric with a base; and
(iii) treating the modified fabric with an aqueous solution comprising a sulfate or chloride salt of an iron cation and a salt (especially a nitrate salt) of a second metal cation, wherein the second metal cation is selected from a lithium, sodium, potassium, magnesium, calcium and zinc cation (especially calcium), and mixtures thereof.

The manufacture as discussed above of a fibrous catalyst wherein the solid support comprises one or more PAN fibres may be conducted in any suitable reactor. In particular, the manufacture may be conducted in a suitable dye bath reactor (i.e. a reactor typically used for dying fabric). In particular, a commercial dye bath with rollers arranged for passing the fabric through the dye bath in which the treatment(s) are conducted may be used. An example of a suitable dye bath reactor is a URGNANO-BERGAMO MCS, WRT 3 reactor (made in Italy).

References herein to aqueous solutions are intended to refer to solutions in a suitable solvent or diluent comprising at least 40%, particularly at least 50%, by volume of water. In particular, the solvent or diluent is water. Additionally, the skilled person would appreciate that such solutions include the component(s) thereof (for example metal salt(s)) substantially dissolved therein but that minor amounts of the component(s) may be present as a suspension in the solvent or diluent. Additionally, a proportion of the component(s) may become suspended in the solvent or diluent as the method step(s) of the present invention are conducted.

For example, a catalyst wherein the solid support comprises a keratinous support may be manufactured (prior to the step of placing the microbes in contact with the catalyst) according to the step of fixing the metal cation to a keratinous support (such as a wool fibre), which keratinous support (such as a wool fibre) may optionally have been modified so as to aid the fixation (or complexation) of the metal cation to the support.

A catalyst wherein the solid support comprises a keratinous support may, for example, be manufactured (prior to the step of placing the microbes in contact with the catalyst) according to the steps of:
(iv) treating a keratinous support (such as a wool fibre) with a hydrazine salt and/or a hydroxylamine salt in the presence of a base to provide a modified keratinous support (such as a modified wool fibre); and
(v) treating the modified keratinous support (such as a modified wool fibre) with an aqueous solution comprising a salt of a first metal cation, which first metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation, and mixtures thereof.

A catalyst wherein the solid support comprises a keratinous support may, for example, be manufactured (prior to the step of placing the microbes in contact with the catalyst) according to the steps of:
(iv) treating a keratinous support (such as a wool fibre) with a hydrazine salt and a hydroxylamine salt in the presence of a base to provide a modified keratinous support (such as a modified wool fibre); and
(v) treating the modified keratinous support (such as a modified wool fibre) with an aqueous solution comprising a salt of a first metal cation, which first metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation, and mixtures thereof.

A catalyst wherein the solid support comprises a keratinous support may, for example, be manufactured (prior to the step of placing the microbes in contact with the catalyst) according to the steps of:
(iv) treating a keratinous support (such as a wool fibre) with a hydroxylamine salt in the presence of a base to provide a modified keratinous support (such as a modified wool fibre); and
(v) treating the modified keratinous support (such as a modified wool fibre) with an aqueous solution comprising a salt of a first metal cation, which first metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation, and mixtures thereof.

A catalyst wherein the solid support comprises a keratinous support may, for example, be manufactured (prior to the step of placing the microbes in contact with the catalyst) according to the steps of:
(iv) treating a keratinous support (such as a wool fibre) with a hydrazine salt in the presence of a base to provide a modified keratinous support (such as a modified wool fibre); and
(v) treating the modified keratinous support (such as a modified wool fibre) with an aqueous solution comprising a salt of a first metal cation, which first metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation, and mixtures thereof.

A catalyst wherein the solid support comprises a keratinous support may, for example, be manufactured (prior to the step of placing the microbes in contact with the catalyst) according to the steps of:
(iv) treating a keratinous support (such as a wool fibre) with an aqueous solution of a hydroxylamine salt in the presence of a base to provide a modified keratinous support (such as a modified wool fibre), wherein the concentration of the hydroxylamine salt in the aqueous solution is in the range of from 14 to 70 g/l; and
(v) treating the modified keratinous support (such as a modified wool fibre) with an aqueous solution comprising a salt of a first metal cation, which first metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation, and mixtures thereof.

In the steps (iv) above of the methods of manufacturing a catalyst that comprises a solid keratinous support, the aqueous solution may further comprise a salt of a second metal cation, which second metal cation is selected from lithium, sodium, potassium, rubidium, cesium, beryllium, magnesium, calcium, strontium, barium, zinc, cadmium, mercury, aluminium, gallium, indium, thallium, tin, lead, antimony and bismuth, and mixtures thereof.

A catalyst wherein the solid support comprises a keratinous support may, for example, be manufactured (prior to the step of placing the microbes in contact with the catalyst) according to the steps of:

(iv) treating a keratinous support (such as a wool fibre) with a hydroxylamine salt in the presence of a base to provide a modified keratinous support (such as a modified wool fibre); and (v) treating the modified keratinous support (such as a modified wool fibre) with an aqueous solution comprising a salt of a first metal cation and a salt of a second metal cation, which first metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation, and mixtures thereof, and which second metal cation is selected from lithium, sodium, potassium, rubidium, cesium, beryllium, magnesium, calcium, strontium, barium, zinc, cadmium, mercury, aluminium, gallium, indium, thallium, tin, lead, antimony and bismuth, and mixtures thereof.

In steps (iv) of the methods of manufacturing a catalyst that comprises a solid keratinous support, the keratinous support (such as a wool fibre) is "modified". It is believed that, in this step, reactive groups on the keratinous support (such as a wool fibre) react with hydroxylamine salts and/or hydrazine salts to form groups (such as hydroxamic groups) that may complex with first metal cations (and possibly with second metal cations) as defined herein.

When a hydrazine salt is used in the step (iv) of the methods of manufacturing a catalyst that comprises a solid keratinous support, as the skilled person would appreciate, any suitable hydrazine salt may be used. For example, suitable hydrazine salts include hydrazine dihydrochloride, hydrazine monohydrochloride, hydrazine hydrate, hydrazine monohydrobromide, hydrazine acetate, hydrazine sulfate and dihydrazine sulfate (particularly hydrazine dihydrochloride, hydrazine sulfate and dihydrazine sulfate), and mixtures thereof. Salts of hydrazines containing from one to four substituents may be used as discussed above, i.e. which substituents may be the same or different and selected from (1-4C)alkyl, aryl (such as phenyl) and (1-4C)alkanoyl and which substituents may be further substituted for example by one or more further substituents which may be the same or different selected from halogen, nitro and hydroxyl. As the skilled person would appreciate, one or more hydrazine salts may be used in this step, as appropriate.

When a hydroxylamine salt is used in the step (iv) of the methods of manufacturing a catalyst that comprises a solid keratinous support, as the skilled person would appreciate, any suitable hydroxylamine salt may be used. For example, suitable hydroxylamine salts include hydroxylamine monohydrochloride, hydroxylamine sulfate and hydroxylamine phosphate (particularly hydroxylamine monohydrochloride and hydroxylamine sulfate), and mixtures thereof. Salts of hydroxylamines containing one or two substituents may be used as discussed above, i.e. which substituents may be the same or different and selected from (1-4C)alkyl, aryl (such as phenyl) and (1-4C)alkanoyl and which substituents may be further substituted for example by one or more further substituents which may be the same or different selected from halogen, nitro and hydroxyl. As the skilled person would appreciate, one or more hydroxylamine salts may be used in this step, as appropriate.

In the step (iv) of the methods of manufacturing a catalyst that comprises a solid keratinous support, the keratinous support typically is treated with a hydrazine salt and/or a hydroxylamine salt in a suitable solvent (for example as a solution of a hydrazine salt and/or a hydroxylamine salt in a suitable solvent) and in the presence of a suitable base. The keratinous support may be treated with a hydrazine salt and a hydroxylamine salt in a suitable solvent (for example as a solution of a hydrazine salt and a hydroxylamine salt in a suitable solvent) and in the presence of a suitable base. Typically, a suitable solvent is an aqueous solvent, such as water. Thus, typically an aqueous solution of a hydrazine salt and/or a hydroxylamine salt is used. The concentration of the hydrazine salt (when present) used in the step (iv) may be in the range of from 10 to 50 g/l, particularly in the range of from 20 to 40 g/l, more particularly about 30 g/l. The concentration of the hydroxylamine salt (when present) used in the step (iv) may be in the range of from 14 to 70 g/l, particularly in the range of from 30 to 55 g/l, more particularly about 42 g/l.

When the keratinous support is treated with a solution of a hydrazine salt and a hydroxylamine salt in the step (iv) of the methods of manufacturing a catalyst that comprises a solid keratinous support, the hydrazine salt and hydroxylamine salt may be present in a molar ratio in the range of from about 1:1 to about 1:3, preferably of about 1:2. Typically in the step (iv) of the methods of manufacturing a catalyst that comprises a solid keratinous support, the weight ratio of wool to total hydrazine salt and/or hydroxylamine salt may be in the range of from about 1:8 to 1:0.5, preferably in the range of from about 1:6 to about 1:2, more preferably in the range of from about 1:4 to about 1:2, even more preferably of about 1:2.7.

Any suitable base may be used in the step (iv) of the methods of manufacturing a catalyst that comprises a solid keratinous support. For example, a suitable base may be selected from sodium hydroxide, potassium hydroxide and sodium carbonate, and mixtures thereof (particularly sodium hydroxide). The base is used in the step (iv) to maintain a suitable pH, i.e. at which modification of the keratinous support may occur. A suitable pH is, for example, a pH in the range of from 4 to 9.5, particularly a pH in the range of from 6 to 8 and more particularly a pH of about 7. The step (iv) of the methods of manufacturing a catalyst that comprises a solid keratinous support may conveniently be conducted at a temperature of greater than room temperature (for example at a temperature of greater than about 25° C.), particularly at a temperature in the range of from 60 to 180° C., more particularly at a temperature in the range of from 100 to 105° C., for example at a temperature of about 100 to 101° C. As the skilled person would appreciate, the time taken for the step (iv) of the methods of manufacturing a catalyst that comprises a solid keratinous support depends on the particular keratinous support and/or reagents used. However, a typical treatment time is from about 30 minutes to 3 hours, suitably about 2 hours.

In the step (v) of the methods of manufacturing a catalyst that comprises a solid keratinous support, the modified keratinous support (i.e. as prepared in step (iv)) is treated with an aqueous solution so as to provide the catalyst. The aqueous solution typically is an aqueous metal salt solution, i.e. comprising a first metal (i.e. transition metal) cation as defined herein. As the skilled person would appreciate, the aqueous solution may, in one aspect, comprise only one salt of a first metal (i.e. transition metal) cation. However, in another aspect, the aqueous solution may comprise more than one salt of a first metal (i.e. transition metal) cation. In other words, the aqueous metal salt solution may comprise a mixture of first metal (i.e. transition metal) salts.

In the step (v), the aqueous solution may comprise a salt of a first metal (i.e. transition metal) cation and a salt of a second metal cation, which first and second metal cations are as defined herein. As the skilled person would appreciate, the second metal cations are cations of the metals belonging to Groups 1, 2, 12, 13, 14 and 15 as set out in the Periodic Table of Elements (according to established IUPAC nomenclature). The aqueous solution may comprise only one salt of a second metal cation or may comprise a mixture of second metal salts. It is believed that the second metal cation salts act as facilitators to increase the fixing of the first metal (i.e. transition metal) cation to the keratinous support.

In one aspect of the methods of manufacturing a catalyst that comprises a solid keratinous support, the second metal cation is selected from lithium, sodium, potassium, magnesium, calcium, zinc and aluminium, and mixtures thereof. In another aspect, the second metal cation is selected from lithium, sodium, potassium, magnesium, calcium and zinc, and mixtures thereof. In another aspect, the second metal cation is selected from a lithium, magnesium, calcium and zinc cation, and mixtures thereof. In yet another aspect, the second metal cation is selected from a lithium and calcium cation, and mixtures thereof. In yet another aspect, the second metal cation is selected from a sodium, potassium and calcium cation, and mixtures thereof. In yet another aspect, the second metal cation is a calcium cation. In yet another aspect, the second metal cation is a sodium cation.

As the skilled person would appreciate, the salts of the second metal cation(s) used in step (v) of the methods of manufacturing a catalyst that comprises a solid keratinous support may comprise any suitable anion. Suitable anions include, for example, chlorides, iodides, bromides, fluorides, sulfates, carboxylates, thiosulfates, thiocyanates, perchlorates, nitrates and nitrites, particularly chlorides, sulfates, nitrates and nitrites, more particularly chlorides, nitrates and sulfates, even more particularly nitrates and sulfates, and mixtures thereof. Suitable second metal cations are as discussed above. Examples of suitable second metal salts include $Ca(NO_3)_2.4H_2O$, $Mg(NO_3)_2.6H_2O$, $Li_2SO_4.H_2O$, $ZnSO_4.7H_2O$, $NaCl$, $Na_2SO_4$ and/or $Na_2SO_4.10H_2O$ (especially $Ca(NO_3)_2.4H_2O$ and/or $Li_2SO_4.H_2O$).

The total metal cation concentration in the aqueous solution used in step (v) of the methods of manufacturing a catalyst that comprises a solid keratinous support may be in the range of from 0.05 g/L to 500 g/L, such as in the range of from 5 g/L to 100 g/L. In the aqueous solution, the molar ratio of the first metal (i.e. transition metal) salt to the second metal salt (when present) may be in the range of from 1:1 to 1:12, particularly in the range of from 1:2 to 1:6, more particularly in the range of from 1:3 to 1:6.

The step (v) of the methods of manufacturing a catalyst that comprises a solid keratinous support may conveniently be conducted at a temperature in the range of from about 5 to 80° C., preferably at ambient temperature, i.e. a temperature in the range of from 10 to 30° C., particularly in the range of from 20 to 30° C., for example about 25° C. The step (v) of the methods of manufacturing a catalyst that comprises a solid keratinous support may conveniently be conducted at any suitable pH, for example at a pH in the range of from 1 to 7, particularly at a pH in the range of from 2 to 3.

Typically, the keratinous support may be washed between each of the steps (iv) and (v) of the methods of manufacturing a catalyst that comprises a solid keratinous support. For example, the keratinous support may be washed with water, for example with distilled water. The washing step substantially removes residual reagents present from the previous reaction step(s). Typically, after the step (v) of the methods of manufacturing a catalyst that comprises a solid keratinous support the catalyst is dried before use. The catalyst may be dried using any conventional means, for example at temperatures up to 125° C.

The keratinous support used in the methods of manufacturing a catalyst that comprises a solid keratinous support may be in any suitable form, for example as discussed above. A wool fibre used in the methods of manufacturing a catalyst that comprises a solid keratinous support may be commercially available and may be purchased as pre-scoured wool fibre.

The methods of manufacturing a catalyst that comprises a solid keratinous support may further comprise a pre-treatment step, for example in which the keratinous support is pre-treated prior to the step (iv). The pre-treatment step may comprise the step of scouring the keratinous material (such as a wool fibre), for example to reduce or remove contaminants on the keratinous material (such as a wool fibre), especially hydrophobic contaminants such as lipids, oils, grease and/or wax. The use of a scoured keratinous material (such as a scoured wool fibre) in the methods of manufacturing a catalyst that comprises a solid keratinous support may provide materials (such as wool fibres) having fewer contaminants (especially hydrophobic contaminants) thereon and therefore it is believed that the use of a scoured wool fibre may promote the efficient modification and impregnation of the fibre.

The pre-treatment step of the methods of manufacturing a catalyst that comprises a solid keratinous support (when conducted) may comprise contacting a wool fibre with water (such as distilled water) and/or contacting a wool fibre with water (such as distilled water) in the presence of a suitable surfactant, such as a non-ionic surfactant. Suitable non-ionic surfactants include alkyl phenol ethoxylates and fatty alcohol ethoxylates. In any pre-treatment step, the wool fibre may additionally or alternatively be contacted with a builder such as soda ash (sodium carbonate), sodium chloride and/or sodium sulfate. It is believed that contacting with such builders may allow for shorter contacting times to achieve the reduction or removal of contaminants from the wool fibre. The wool fibre may be dried by any conventional means prior to the modification step. The pre-treatment step may be conducted at any suitable temperature, for example at a temperature in the range of from 40 to 80° C., especially in the range of from 50 to 70° C., more especially at about 60° C.

A catalyst wherein the solid support comprises a keratinous support may, for example, be manufactured (prior to the step of placing the microbes in contact with the catalyst) according to the steps of:

(iv) treating a keratinous support (such as a wool fibre) with a hydrazine salt and/or a hydroxylamine salt in the presence of a base to provide a modified keratinous support (such as a modified wool fibre); and (v) treating the modified keratinous support (such as a modified wool fibre) with an aqueous solution comprising a salt of a second metal cation, which second metal cation is selected from a zinc and aluminium cation, and mixtures thereof. In this method, the reaction conditions, reagent amounts and so on may be as described above in relation to the manufacture of a catalyst wherein the solid support comprises a keratinous support, except that only a second metal cation selected from a zinc and aluminium cation, and mixtures thereof is included in the aqueous metal salt solution.

The manufacture as discussed above of a fibrous catalyst wherein the solid support comprises a keratinuous support may be conducted in any suitable reactor, including for example a suitable dye bath reactor as discussed above. When such a dye bath reactor is used, the keratinous support (for example comprising wool fibres) typically is in the form of a fabric (for example felted, knitted, woven or needle punched).

According to a further aspect of the present invention, there is provided a method of disinfecting a substrate, the method comprising the step of placing the substrate in contact with a catalyst by means of fluid medium, wherein the catalyst comprises a solid support, which solid support comprises one or more fibres, and a metal cation fixed to the support. There is also provided the use of a catalyst for disinfecting a substrate in contact with the catalyst by means of a fluid medium, wherein the catalyst comprises a solid support, which solid support comprises one or more fibres, and a metal cation fixed to the support. Preferably, the fluid medium is a liquid medium. In the method of/use for disinfecting a substrate, the catalyst and fluid medium may be as described above. The method may further comprise the step of manufacturing the catalyst prior to the method of disinfecting, for example using a method of manufacture as described above.

There is provided the use of a catalyst for killing and/or inactivating microbes in a fluid medium, wherein the catalyst comprises a solid support, which solid support comprises one or more fibres, and a metal cation fixed to the support. Preferably, the fluid medium is a liquid medium. In this use, the catalyst and fluid medium may be as described above. The catalyst for this use may be manufactured prior to its use in killing and/or inactivating microbes, for example using a method of manufacture as described above.

According to a further aspect of the present invention, there is provided a composition for killing and/or inactivating microbes, the composition comprising a catalyst, a peroxygen compound and a fluid medium, wherein the catalyst comprises a solid support, which solid support comprises one or more fibres, and a metal cation fixed to the support. Preferably, the fluid medium is a liquid medium. In the composition, the catalyst, peroxygen compound and fluid medium may be as described above. The catalyst may be manufactured by any suitable method, for example using a method of manufacture as described above. The composition may comprise the catalyst and the peroxygen compound, such as hydrogen peroxide, in a weight ratio of from about 1:20 to about 20:1.

According to a further aspect of the present invention, there is provided an apparatus for killing and/or inactivating microbes, the apparatus comprising a catalyst, a peroxygen compound and a fluid medium, wherein the catalyst comprises a solid support, which solid support comprises one or more fibres, and a metal cation fixed to the support. Preferably, the fluid medium is a liquid medium. Preferably, the catalyst and the peroxygen compound are spaced apart in the apparatus. In the apparatus, the catalyst, peroxygen compound and fluid medium may be as described above. The catalyst may be manufactured by any suitable method, for example using a method of manufacture as described above. The apparatus may comprise the catalyst and the peroxygen compound in a weight ratio of from about 1:20 to about 20:1.

According to a further aspect of the present invention, there is provided a method for preparing a catalyst comprising a keratinuous support (such as a wool fibre) and a metal cation fixed to the keratinous support. The method comprises the steps of:

(iv-a) treating a keratinous support (such as a wool fibre) with a hydrazine salt and a hydroxylamine salt in the presence of a base to provide a modified keratinous support (such as a modified wool fibre); and (v-a) treating the modified keratinous support (such as a modified wool fibre) with an aqueous solution comprising a salt of a first metal cation, which first metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation, and mixtures thereof.

The present invention further provides a method for preparing a catalyst, the method comprising the steps of:

(iv-b) treating a keratinous support (such as a wool fibre) with a hydrazine salt in the presence of a base to provide a modified keratinous support (such as a modified wool fibre); and (v-b) treating the modified keratinous support (such as a modified wool fibre) with an aqueous solution comprising a salt of a first metal cation, which first metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation, and mixtures thereof.

The present invention further provides a method for preparing a catalyst, the method comprising the steps of:

(iv-c) treating a keratinous support (such as a wool fibre) with an aqueous solution of a hydroxylamine salt in the presence of a base to provide a modified keratinous support (such as a modified wool fibre), wherein the concentration of the hydroxylamine salt in the aqueous solution is in the range of from 14 to 70 g/l; and (v-c) treating the modified keratinous support (such as a modified wool fibre) with an aqueous solution comprising a salt of a first metal cation, which first metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation, and mixtures thereof.

In the steps (v-a), (v-b) and/or (v-c) of the methods above, the aqueous solution may further comprise a salt of a second metal cation, which second metal cation is selected from lithium, sodium, potassium, rubidium, cesium, beryllium, magnesium, calcium, strontium, barium, zinc, cadmium, mercury, aluminium, gallium, indium, thallium, tin, lead, antimony and bismuth, and mixtures thereof.

The present invention further provides a method for preparing a catalyst, the method comprising the steps of:

(iv-d) treating a keratinous support (such as a wool fibre) with a hydroxylamine salt in the presence of a base to provide a modified keratinous support (such as a modified wool fibre); and (v-d) treating the modified keratinous support (such as a modified wool fibre) with an aqueous solution comprising a salt of a first metal cation and a salt of a second metal cation, which first metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation, and mixtures thereof, and which second metal cation is selected from lithium, sodium, potassium, rubidium, cesium, beryllium, magnesium, calcium, strontium, barium, zinc, cadmium, mercury, aluminium, gallium, indium, thallium, tin, lead, antimony and bismuth, and mixtures thereof.

In steps (iv-a), (iv-b), (iv-c) and (iv-d) of the methods of the present invention for preparing a catalyst, the keratinous support (such as a wool fibre) is "modified", as discussed above.

The steps (iv-a), (iv-b), (iv-c) and (iv-d) are referred to hereinafter as the "modification step(s)" and preferred aspects of these steps correspond to preferred aspects of the steps (iv) discussed above.

When a hydrazine salt is used, in the modification step, as the skilled person would appreciate, any suitable hydrazine salt may be used. For example, suitable hydrazine salts include hydrazine dihydrochloride, hydrazine monohydrochloride, hydrazine hydrate, hydrazine monohydrobromide, hydrazine acetate, hydrazine sulfate and dihydrazine sulfate (particularly hydrazine dihydrochloride, hydrazine sulfate and dihydrazine sulfate), and mixtures thereof. Salts of hydrazines containing from one to four substituents may be used as discussed above. As the skilled person would appreciate, one or more hydrazine salts may be used in the modification step, as appropriate.

When a hydroxylamine salt is used in the modification step, as the skilled person would appreciate, any suitable hydroxylamine salt may be used. For example, suitable hydroxylamine salts include hydroxylamine monohydrochloride, hydroxylamine sulfate and hydroxylamine phosphate (particularly hydroxylamine monohydrochloride and hydroxylamine sulfate), and mixtures thereof. Salts of hydroxylamines containing one or two substituents may be used as discussed above. As the skilled person would appreciate, one or more hydroxylamine salts may be used in the modification step, as appropriate.

In the modification step, the keratinous support typically is treated with a hydrazine salt and/or a hydroxylamine salt in a suitable solvent (for example as a solution of a hydrazine salt and/or a hydroxylamine salt in a suitable solvent) and in the presence of a suitable base. The keratinous support may be treated with a hydrazine salt and a hydroxylamine salt in a suitable solvent (for example as a solution of a hydrazine salt and a hydroxylamine salt in a suitable solvent) and in the presence of a suitable base. Typically, a suitable solvent is an aqueous solvent, such as water. Thus, typically an aqueous solution of a hydrazine salt and/or a hydroxylamine salt is used. The concentration of the hydrazine salt (when present) used in the modification step may be in the range of from 10 to 50 g/l, particularly in the range of from 20 to 40 g/l, more particularly about 30 g/l. The concentration of the hydroxylamine salt (when present) used in the modification step may be in the range of from 14 to 70 g/l, particularly in the range of from 30 to 55 g/l, more particularly about 42 g/l.

When the keratinous support is treated with a solution of a hydrazine salt and a hydroxylamine salt in the modification step, the hydrazine salt and hydroxylamine salt may be present in a molar ratio in the range of from about 1:1 to about 1:3, preferably of about 1:2. Typically in the modification step, the weight ratio of wool to total hydrazine salt and/or hydroxylamine salt may be in the range of from about 1:8 to 1:0.5, preferably in the range of from about 1:6 to about 1:2, more preferably in the range of from about 1:4 to about 1:2, even more preferably of about 1:2.7.

Any suitable base may be used in the modification step of the methods for preparing a catalyst of the present invention. For example, as discussed above, a suitable base may be selected from sodium hydroxide, potassium hydroxide and sodium carbonate, and mixtures thereof (particularly sodium hydroxide). The base is used in the modification step to maintain a suitable pH, i.e. at which modification of the keratinous support may occur. A suitable pH is, for example, a pH in the range of from 4 to 9.5, particularly a pH in the range of from 6 to 8 and more particularly a pH of about 7. Typical temperatures and treatment times for the modification step are as discussed above.

As discussed above, in the steps (v-a), (v-b), (v-c) and (v-d) of the methods for preparing a catalyst of the present invention, the modified keratinous support (i.e. as prepared in the corresponding modification steps) is treated with an aqueous solution so as to provide the catalyst. The aqueous solution typically is an aqueous metal salt solution, i.e. comprising a first metal cation as defined herein. The steps (v-a), (v-b), (v-c) and (v-d) are referred to hereinafter as the "impregnation step(s)" and preferred aspects of these steps correspond to preferred aspects of the steps (v) discussed above. The aqueous solution comprises a salt of a first metal cation as defined herein. As discussed above, the aqueous solution may comprise only one salt of a first metal cation or may comprise more than one salt of a first metal cation. The aqueous metal salt solution may comprise a mixture of first metal salts.

Preferred first metal cations are selected as discussed above. For example, the first metal cation may selected from a scandium, titanium, vanadium, chromium, manganese, iron, cobalt, nickel and copper cation, particularly from a titanium, chromium, manganese, iron, cobalt, nickel and copper cation, more particularly from a chromium, manganese, iron, cobalt, nickel and copper cation, and mixtures thereof. In one aspect, the first metal cation is selected from an iron (for example $Fe^{2+}$ or $Fe^{3+}$) and copper (for example $Cu^{2+}$) cation, and mixtures thereof. In another aspect, the first metal cation is an iron cation (for example $Fe^{2+}$ or $Fe^{3+}$, especially $Fe^{3+}$).

The salts of the first metal cation(s) may comprise any suitable anion, such as those discussed above. In particular, suitable anions include chlorides, sulfates, nitrates and/or nitrites, more particularly chlorides and/or sulfates, even more particularly chlorides. Examples of suitable first metal salts include $FeCl_3.6H_2O$, $FeSO_4.xH_2O$ (wherein x is 0, 1, 4, 5 or 7), $Fe_2(SO_4)_3.H_2O$, $CuCl_2.2H_2O$ and/or $CuSO_4.5H_2O$ (especially $FeCl_3.6H_2O$ and/or $Fe_2(SO_4)_3.H_2O$).

In the impregnation step, the aqueous solution may comprise a salt of a first metal cation and a salt of a second metal cation, which first and second metal cations are as defined herein. The aqueous solution may comprise only one salt of a second metal cation or may comprise a mixture of second metal salts. Preferred second metal cations ate selected as discussed above. For example, the second metal cation may be selected from a lithium, sodium, potassium, magnesium, calcium, zinc and aluminium, more particularly from a lithium, sodium, potassium, magnesium, calcium and zinc, even more particularly from a lithium, magnesium, calcium and zinc cation, yet even more particularly from a sodium, potassium and calcium cation, and mixtures thereof. In one aspect, the second metal cation is a calcium cation. In another aspect, the second metal cation is a sodium cation.

The salts of the second metal cation(s) may comprise any suitable anion, such as those discussed above. In particular, suitable anions include chlorides, sulfates, nitrates and/or nitrites, more particularly chlorides, nitrates and/or sulfates, even more particularly nitrates and/or sulfates. Examples of suitable second metal salts include $Ca(NO_3)_2.4H_2O$, $Mg(NO_3)_2.6H_2O$, $Li_2SO_4.H_2O$, $ZnSO_4.7H_2O$, $NaCl$ and/or $Na_2SO_4$ (especially $Ca(NO_3)_2.4H_2O$ and/or $Li_2SO_4.H_2O$).

The total metal cation concentration in the aqueous solution may be in the range of from 0.05 g/L to 500 g/L, such as in the range of from 5 g/L to 100 g/L. In the aqueous solution, the molar ratio of the first metal salt to the second metal salt (when present) may be in the range of from 1:1 to 1:12, particularly in the range of from 1:2 to 1:6, more particularly in the range of from 1:3 to 1:6. Typical temperatures and treatment times for the impregnation step are as discussed above. The impregnation step may conveniently be conducted at any suitable pH, for example at a pH in the range of from 1 to 7, particularly at a pH in the range of from 2 to 3.

Typically, the keratinous support is washed (for example with water) between each of the modification and impregnation steps and dried before use as discussed above. The method may further comprise a pre-treatment step, for example in which the keratinous support is pre-treated prior to the modification step, as discussed above.

The keratinous support used may be in any suitable form and the method for preparing the catalyst may further comprise the step of forming a fabric or cloth from a keratinous material (such as a wool fibre) as discussed above. Additionally, wool fibres for used in the method are as discussed above.

According to another aspect of the present invention there is provided a catalyst obtainable by the methods of the present invention for preparing the catalyst comprising a keratinuous support (such as a wool fibre) and a metal cation fixed to the keratinous support. According to yet another aspect of the present invention there is provided a catalyst obtained by the methods of the present invention for preparing the catalyst comprising a keratinuous support (such as a wool fibre) and a metal cation fixed to the keratinous support.

According to a further aspect of the present invention, there is provided a catalyst comprising a keratinous support and a first metal cation fixed to the keratinous support, which first metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum, gold, zinc and aluminium cation (particularly selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation), and mixtures thereof and wherein the first metal cation is present in an amount of 0.03 mmol or greater per gram of keratinous support. According to another aspect of the present invention, there is provided a catalyst comprising a wool fibre and a first metal cation fixed to the wool fibre, which first metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum, gold, zinc and aluminium cation (particularly selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation), and mixtures thereof and wherein the first metal cation is present in an amount of 0.03 mmol or greater per gram of wool fibre. For example, in the catalysts of the present invention, the first metal cation may be present in an amount of from 0.03 to 1.0 mmol per gram of wool fibre, such as in an amount of from 0.03 to 0.5 mmol per gram of wool fibre, more particularly of from 0.03 to 0.1 mmol per gram of wool fibre, even more particularly of from 0.07 to 0.1 mmol per gram of wool fibre. The wool fibre and first metal cation are as defined above.

According to another aspect of the present invention there is provided a method of catalysing a chemical reaction, wherein the method comprises the step of contacting one or more reactants with a catalyst, wherein the catalyst comprises a keratinous support and a first metal cation fixed to the keratinous support, which first metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation, and mixtures thereof, under conditions for catalysis of the chemical reaction.

According to another aspect of the present invention there is provided a method of catalysing a chemical reaction, wherein the method comprises the step of contacting one or more reactants with a catalyst, wherein the catalyst comprises a wool fibre and a first metal cation fixed to the wool fibre, which first metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation, and mixtures thereof, under conditions for catalysis of the chemical reaction.

The method of the present invention of catalysing a chemical reaction, which uses a catalyst comprising a keratinous support (such as a wool fibre), provides very real advantages in use. The catalysts comprising a keratinous support (such as a wool fibre) are economical and convenient to prepare, for example using starting materials that are readily available, cheap and safe to use. The catalysts comprise materials that are available naturally, without substantial manufacturing and/or processing prior to their use in catalysis. Additionally, the used or spent catalysts are easily and conveniently disposed of. Furthermore, the catalysts are efficient in a range of chemical reactions, particularly in oxidation reactions, and can be used in a range of different conditions, such as at a range of different pHs (for example typically at a pH range of about 2 to 9.5). The catalysts also can be made into a range of forms suitable for being installed into different systems/devices.

The chemical reaction catalysed according to the method of the present invention may be any suitable chemical reaction. For example, the chemical reaction may be an oxidation reaction, for example in which one or more organic compounds is oxidised. The chemical reaction may alternatively be a hydrogenation reaction (for example when the first metal cation is a selected metal cation, such as a palladium cation).

The method of catalysing a chemical reaction includes the step of contacting the one or more reactants with the catalyst. The reactants and catalyst may be contacted in any suitable manner, for example by placing them in a suitable reaction vessel, preferably with agitation and/or stirring. Suitably, the catalyst may be contacted with the one or more reactants by means of a fluid medium, wherein the fluid medium may be liquid or gaseous as described herein. The fluid medium may comprise the one or more reactants and/or one or more additional solvents and/or carriers.

When the chemical reaction is an oxidation reaction, the one or more reactants are suitably contacted with the catalyst in the presence of an oxidant. Any suitable oxidant may by used, as defined herein.

In particular, the chemical reaction catalysed by the method of the present invention may be a chemical reaction conducted in a waste stream, for example to treat the waste stream so as to oxidise undesired organic compounds present in the waste stream. Such oxidation of the undesired organic compounds typically results in their decomposition and conversion into derivatives that may be disposed of or, if appropriate, isolated and collected for further use. Thus, the method of catalysing a chemical reaction may comprise the step of contacting one or more reactants in a waste stream with the catalyst. In other words, in such a method, the one or more reactants may represent one or more undesired organic compounds that it is desired to decompose and convert into derivatives. The one or more undesired organic compounds are typically contacted with the catalyst in the presence of an oxidant.

Thus, the present invention further provides a method of treating a waste stream by catalysing a chemical reaction, wherein the method comprises the step of contacting one or more reactants in the waste stream with a catalyst, wherein the catalyst comprises a keratinous support and a first metal cation fixed to the keratinous support, which first metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation, and mixtures thereof, under conditions for catalysis of the chemical reaction.

The present invention further provides a method of treating a waste stream by catalysing a chemical reaction, wherein the method comprises the step of contacting one or more reactants in the waste stream with a catalyst, wherein the catalyst comprises a wool fibre and a first metal cation fixed to the wool fibre, which first metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation, and mixtures thereof, under conditions for catalysis of the chemical reaction.

A wide variety of waste streams comprising virtually any undesired organic compound(s) may be contacted with the catalyst according to the method of catalysing a chemical reaction of the present invention. In other words, the chemical reaction catalysed may comprise the oxidative decomposition of virtually any undesired organic compound(s). For example, the waste stream may originate from any suitable industry, including from the chemical, pharmaceutical, petroleum chemical, textile, pulp, leather, agro-chemical, furniture manufacturing and photo-processing industries, and may comprise virtually any undesired organic compound(s). In particular, the waste stream to be treated may contain one or more undesired organic compounds, for example the waste stream may contain one or more undesired phenol compounds and originate from an industry such as the paper or chemical industries. The waste stream to be treated may contain one or more undesired organic compounds, for example one or more undesired hormones.

References herein to a chemical reaction conducted in a waste stream so as to treat the waste stream are intended to refer to the conversion of an undesired, potentially harmful, "waste" compound contained in the waste stream into a new derivative that typically is at least less harmful and/or easier to dispose of. In some cases, the new derivative formed may be useful in another process and/or application and may be isolated and/or collected for further use. When this is not the case, the new derivative that is formed typically will be collected and/or disposed of in any suitable manner. As discussed above, the conversion of the undesired "waste" compound into a new derivative typically is by the oxidative decomposition of that compound.

Examples of undesired, organic waste compounds that may be oxidised in the chemical reaction include one or more organic compounds selected from sulfides, thiols, dyes, phenols (including bisphenols, nonylphenols and aminophenols), amines, phenylenediamines, triethanol amine, ethylenediamine and tetraacetic acid (for example one or more organic compounds selected from sulfides, dyes, phenols, nonylphenols, aminophenols, amines, phenylenediamines, triethanol amine, ethylenediamine and tetraacetic acid, especially one or more organic compounds selected from phenols, nonylphenols and/or aminophenols).

The chemical reaction catalysed by the method of the present invention may not proceed to 100% reaction. For example, when the chemical reaction is an oxidation reaction, the catalysed chemical reaction may not convert 100% of the organic compound(s) (for example the undesired "waste" compound(s) in a waste stream) into the new derivative(s). As the skilled person would appreciate, the percentage conversion will depend on a number of factors, including the particular catalyst selected and the chemical reaction being conducted, which may depend on the composition of a waste stream being treated. It is expected that the oxidation reaction and catalysts of the present invention will generally convert from about 50% to about 100% by weight of the organic compound(s) (for example the undesired "waste" compound(s) in a waste stream) into the new derivative(s).

The method of catalysing a chemical reaction is conducted under conditions suitable for the catalysis of the chemical reaction. As the skilled person would appreciate, the particular conditions used will depend on a number of factors, including the particular chemical reaction being conducted and the particular catalyst used. Typically, a preferred pH is in the range of from 2 to 9.5. The one or more reactants are typically in the form of a fluid, which may be liquid or gaseous. For example, the one or more reactants may be provided in a waste stream, which waste stream is in the form of a fluid, which may be liquid or gaseous. In one aspect, the one or more reactants are provided in a waste stream which is in the liquid phase. For example, the liquid waste stream may be aqueous or organic based.

The waste stream may originate from any relevant process or industry, for example the waste stream may originate from the chemical, pharmaceutical, petroleum chemical, agro-chemical, textile, pulp, leather, furniture manufacturing or photo-processing industry, particularly from the textile, pulp or photo-processing industry. Examples of dyes that may be oxidised in the catalytic method of the present invention include anthraquinone dyes, such as Acid Blue 45 and Natural Red 4, and azo dyes, such as Cetacid red 4G. Examples of phenol compounds that may be oxidised in the catalytic method of the present invention include phenol, nonylphenol (for example 4-nonylphenol), as well as bisphenols (for example bisphenol A). Examples of sulfide compounds that may be oxidised in the catalytic method of the present invention include dialkylsulfides (for example diethylsulfide). Examples of thiol compounds that may be oxidised in the catalytic method of the present invention include alkylthiols (for example butylmercaptan). An example of a hormone that may be oxidised in the catalytic method of the present invention is estrone (E1).

The method of the present invention of catalysing a chemical reaction comprises the step of contacting one or more reactants with a catalyst. The catalyst comprises a keratinous support and a first metal cation fixed to the keratinous support, which first metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation, and mixtures thereof. The first metal cations are all cations of transition metals. It is believed that the first metal cation(s) form a complex with reactive groups on the keratinous support, i.e. so as to fix the first metal cation to the keratinous support. As the skilled person would appreciate, the particular first metal cation(s) used depends on the chemical reaction being catalysed, for example on the composition of a waste stream being treated, and on the reaction/treatment conditions applied.

Keratinous supports include supports derived from animal fleeces, such as wool, mohair, camel hair and so on, as well as supports derived from animal nail and/or hoof. The keratinous support may be in any suitable form, such as in the form of fibres and/or flakes. For example, the keratinous support may be wool (for example a wool fibre), as discussed above.

The method of catalysing a chemical reaction may further comprise the step of preparing the catalyst, i.e. for use in the catalytic method. The catalyst may be prepared by any suitable method and the method of preparation of the catalyst typically comprises the step of fixing the first metal cation to a keratinous support (such as a wool fibre), which keratinous support (such as a wool fibre) may optionally have been modified prior to impregnation with the first metal cation. Suitable methods of preparing the catalyst include (but are not limited to) those methods discussed herein. If appropriate, the catalyst may be prepared and used in the method of catalysing a chemical reaction in situ.

According to another aspect of the present invention, there is provided the use of a catalyst as herein defined for the catalysis of a chemical reaction. For example, there is provided the use of a catalyst comprising a keratinous support (such as a wool fibre) and a first metal cation fixed to the keratinous support, which first metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation, and mixtures thereof, for the catalysis of a chemical reaction. According to another aspect of the present invention, there is provided the use of a catalyst as herein defined in the treatment of a waste stream. For example, there is provided the use of a catalyst comprising a keratinous support (such as a wool fibre) and a first metal cation fixed to the keratinous support, which first metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum and gold cation, and mixtures thereof, in the treatment of a waste stream by the catalysis of a chemical reaction. In these uses, preferred aspects are as set out above.

The invention will now be illustrated by the following non-limiting examples in which, unless stated otherwise:
(a) temperatures are given in degrees Celsius (° C.);
(b) operations were conducted at room or ambient temperature, that is a temperature in the range of from 18 to 25° C. (unless otherwise stated);
(c) chemical symbols have their usual meanings;
(d) SI symbols and units are used; and
(E) Ultra-violet/Visible spectra were recorded on a UNICAM UV2-100 spectrophotometer.

Antimicrobial Activity

EXAMPLES 1 to 96

The antimicrobial activity of a catalyst comprising PAN fibres was examined.

Preparation of the Catalyst

The catalysts were prepared as follows:

PAN1 and PAN2 Catalysts

Step (i)—Modification

For the PAN1 catalyst, the modifying solution used in step (i) comprised $N_2H_4.2HCl$ in distilled water at a concentration of 30 g/l and $NH_2OH.HCl$ in distilled water at a concentration of 42 g/l. The total volume of modifying solution was 800 mL (containing 24 g/L $N_2H_4.2HCl$ and 33.6 g/L $NH_2OH.HCl$). The pH of the modifying solution was 9.5, adjusted by addition of NaOH. A knitted mesh (consisting of 40% (w/w) PAN thread and 60% (w/w) of inert polypropylene (PP) support) in an amount of 31 g (containing 12.4 g of PAN thread and 18.6 g of inert PP thread) was treated with the modifying solution. Thus the liquor ratio was 800 mL:31 g of knitted mesh or 800 mL:12.4 g of PAN thread. The modifying solution, containing the mixture of hydrazine/hydroxylamine at pH 9.5 was, firstly, heated up to 100 to 101° C. and then the knitted mesh was introduced into the modifying solution. The duration of treatment was 2 hours (since the mesh was introduced into solution) at boiling temperature of the modifying solution (100 to 102° C.).

For the PAN2 catalyst, step (i) was conducted in the same way as PAN1 as discussed above, but the PAN2 knitted mesh contained 70% (w/w) of PAN thread and 30% (w/w) of inert PP support. Therefore, the amount of the knitted mesh in 800 mL of modifying solution (mixture of hydrazine/hydroxylamine at pH 9.5) was different, such as 800 mL:17.7 g of knitted mesh (containing 12.4 g of PAN2 thread), but liquor ratio was the same for amount of PAN2 thread, such as 800 mL:12.4 g of PAN thread.

Step (ii)—Further Modification

After step (i), each modified mesh (either PAN 1 or PAN2 as described above) was washed with distilled water (about 2 L) and dried until it had a constant weight at room temperature. Each modified mesh (either PAN 1 or PAN 2 as described above) was then treated in the same way, namely by treating with 5% (w/v) of NaOH boiling solution for 30 seconds. NaOH solution (aqueous) was heated first up to the boiling temperature and then the mesh was introduced into the solution for 30 seconds. Liquor ratio was 800 mL of 5% (w/v) NaOH solution:31 g of knitted mesh (for PAN1) or 17.7 g of knitted mesh for PAN2, or 800 mL of 5% (w/V) NaOH solution:12.4 g of PAN thread (for both PAN1 and PAN2). After step (ii), each modified mesh (either PAN1 or PAN2) was washed thoroughly with distilled water (about 7 L) and dried until its constant weight at room temperature. The PAN1 and PAN2 meshes formed at this stage are preferred to below as PAN1 control and PAN2 control.

Step (iii)—Impregnation

After step (ii), each modified mesh (either PAN1 or PAN2 as described above), was impregnated in the same way with iron and calcium salts, namely $[FeCl_3.6H_2O]=0.75$ g/100 mL and $[Ca(NO_3)_2.4H_2O]=2.25$ g/100 mL in 100 mL of water. Liquor ratio was 1 L of Fe/Ca solution to 30 g of knitted mesh (PAN1 catalyst) or 1 L of Fe/Ca solution to 17.2 g of knitted mesh (PAN2 catalyst) (or 1 L of Fe/Ca solution to 12 g of PAN (either PAN1 catalyst or PAN2 catalyst)). Duration of impregnation was 19 hours and this was conducted at room temperature. After impregnation (step (iii)), either PAN1 or PAN2 knitted mesh was very thoroughly washed with distilled water (about 10 L) and dried until its constant weight at room temperature.

PAN3 Catalyst

The PAN3 catalyst was prepared in a URGNANO-BERGAMO MCS, WRT 3 reactor (made in Italy; a model dye bath reactor)

Step (i)—Modification

For the PAN3 catalyst, the reagents and quantities used in step (i) were as follows:

| Chemical | Quantity |
| --- | --- |
| Water | 600 L |
| Dihydrazine sulfate | 15.666 kg |
| Hydroxylamine sulfate | 32.478 kg |
| Sodium hydroxide | 22.2695 kg |
| PAN mesh (normal) | 16.75 kg, 25 m long × 2.2 m wide |

The reactor was filled with about 600 L of water. Then 13.9 kg of dihydrazine sulfate and 29.76 kg of hydroxylamine sulfate were added, followed by mixing. The pH of the solution was then adjusted to 9.4 using the side dosage unit. This was achieved by initially putting 19 Kg of NaOH (solid pellets) into the solution, followed by step wise addition of NaOH (solid pellets) accompanied by pH verification until the desired pH was attained. A sample of the start up modifying solution was then collected in order to determine actual initial concentration of reagents (dihydrazine sulfate and hydroxylamine sulfate).

The mesh (which was knitted in the form of a close loop with a radius of about 0.35 m) was first cut to obtain a sheet of width 2.2 m. About 16.75 kg of the mesh was then loaded into the reactor. The reactor was closed and the temperature raised from 26° C. to 100° C. in 33 minutes. The speed of rotation of the mesh in the reactor was set to 150 meters/minute. The temperature of the solution in the reactor was manually maintained at 97 to 102° C. for two hours. The reactor was then cooled for 15 minutes to a temperature of 60° C. Samples of the used solution were collected for analysis, and the reactor was then drained. The maximum pressure during the modification was 6 Psi (0.4 bar).

The mesh was washed in a batch process, four times each with 600 L of water (5 minutes per batch) and liquid samples after each wash were collected. The rotation of the mesh in the reactor during the batch washing process was 145 meters/minute. A qualitative test was used to monitor the amount of hydrazine in solution in order to determine the washing end point. The determination of hydrazine was based on the reaction of hydrazine with 4-dimethylamino benzaldehyde (DAB) to form a yellow dye (Wavelength of maximum absorption in the UV/VIS region for hydrazine/DAB is 425 nm). The test consisted of solutions of 4-dimethyl amino benzaldehyde prepared in the lab and bottled. Solutions of DAB containing known concentrations of hydrazine were pre-prepared to aid visual comparison of colour intensities. After four batch washes, a sample of mesh was collected by cutting across its entire width. The modification process resulted in an observable change in colour of the mesh from white, through orange to yellow. The colour of the mesh at the end of modification step (i) was very uniform suggesting a homogenous modification of site as well as good mixing.

Step (ii)—Further Modification

For the PAN3 catalyst, the reagents and quantities used in step (ii) were as follows:

| Chemical | Quantity |
| --- | --- |
| Water | 600 L |
| Sodium hydroxide | 15 kg |

The mesh was left in position in the reactor after the step (i) modification. The reactor containing the mesh was fed with 600 L of water and the temperature was raised to 50° C. This was followed by the gradual addition of 15 kg of NaOH (solid pellets) by means of the side dosage unit. This process was performed very slowly and with care as NaOH fumes were produced during the exothermic reaction of NaOH and water. The reactor was then heated up to 60° C. and maintained in isothermal conditions (temperature of 60±° C.) for 15 minutes. Washing of the mesh was performed by over flow washing for 20 minutes (i.e. by which a continuous flow of water was washed over the mesh in the reactor whilst the mesh was in constant rotation in the reactor) and a sample of mesh was collected for analysis. Visual observation of the step (ii) modified mesh showed a very homogenous colour, suggesting a homogenous modification of site as well as good mixing.

Step (iii)—Impregnation

For the PAN3 catalyst, the reagents and quantities used in step (iii) were as follows:

| Chemical | Quantity |
| --- | --- |
| Water | 600 L |
| Ferric sulfate monohydrate | 3.47 kg |
| Calcium nitrate tetrahydrate | 13.5 kg |

The reactor was fed with 600 L of water followed by the addition of 3.47 kg of ferric sulfate monohydrate and 13.5 kg of calcium nitrate tetrahydrate. The reactor was closed and the rotation of the mesh set at 140 meters per minute. After a reaction time of one hour at room temperature, a sample of mesh was collected for analysis. The duration of overall impregnation was 2 hours. After the impregnation process, a liquid sample was collected to analyse the residual iron in solution. The mesh was flow washed for 20 minutes followed by four batch washes of 5 minutes each with a 600 L wash volume. Wash solutions were collected for analysis. The mesh was dried by blowing warm air through at a temperature of about 50° C. The impregnated mesh had a homogeneous colour.

Testing for Antimicrobial Activity

Neutralisation (nullification of activity) of antimicrobial agents is required to prevent inhibitory concentrations from being transferred to the recovery medium (as discussed, for example, in Russell A. D. (2004) Factors influencing the efficacy of antimicrobial agents in *Principles and Practice of Disinfection Preservation and Sterilization*, 4th edition, eds Fraise A. P., Lambert P. A. and Maillard J. Y., pages 98-127, Oxford: Blackwell Publishing Ltd. and Russell A. D., Ahonkhai I. and Rogers, D. T. (1979) A review: microbiological applications of the inactivation of antibiotics and other antimicrobial agents. *Journal of Applied Bacteriology*, 46, 207-245). Thus, samples were removed at desired time points and then any hydrogen peroxide present in the sample was neutralised (i.e. deactivated) using catalase.

In the examples, catalase from bovine liver was used to neutralise the activity of any remaining hydrogen peroxide (as described in Russell A. D., Ahonkhai I. and Rogers, D. T. (1979), A review: microbiological applications of the inactivation of antibiotics and other antimicrobial agents, *Journal of Applied Bacteriology*, 46, 207-245) after the appropriate contact time during the experiments. Control experiments were conducted to establish whether the neutraliser nullified the activity of hydrogen peroxide and whether the neutraliser was toxic to the micro-organisms tested.

The catalyst used was found to lower the pH of a solution upon its addition to the test solution. Control experiments (Control Examples 35 to 46) therefore were conducted to investigate the effect of pH on the survival of microorganisms. The effect of acidic pH conditions (pH 3.47 to 3.54) were investigated with and without hydrogen peroxide and air.

A quantitative suspension test (as described in Reybrouck G. (1998), The testing of disinfectants, *International Biodeterioration and Biodegradation*, 41, 269-272) based on the general principles of European quantitative suspension tests (BS EN1040:2005: Chemical disinfectants and antiseptics, Quantitative suspension test for the evaluation of basic bactericidal activity of chemical disinfectants and antiseptics, Test method and requirements (phase 1), London: British Standards Institute; BS EN 1276:1997: Chemical disinfectants and antiseptics, Quantitative suspension test for the evaluation of bactericidal activity of chemical disinfectants and antiseptics used in food, industrial, domestic, and institutional areas, Test method and requirements (phase 2, step 1). London: British Standards Institute) was used to establish the basic level of activity of the catalyst in the absence of organic matter. All tests were performed independently at least three times unless otherwise stated. Low concentrations (0.2-1% w/v) of hydrogen peroxide were used so that increases in antimicrobial activity could be detected if present.

Bacteria were inoculated into 10 ml volumes of nutrient broth and incubated at 37° C. for 18 to 24 hours at a shaking speed of 100 revolutions/minute. After incubation, the bacteria were washed by centrifugation to remove the nutrient broth; supernatants were discarded and the bacterial pellets were resuspended in sterilised distilled water. 7.5 ml of the washed bacterial suspension was added to 67.5 ml of hydrogen peroxide and/or distilled water to give a specific final concentration (ranging from 0 to 1% w/v—see Tables below) of hydrogen peroxide and approximately 8 $\log_{10}$ colony forming units (CFU)/mL of bacteria. The resultant mixture was stirred magnetically throughout the experiment. Where applicable, 1 g (+/−0.1 g) of either modified PAN fibre (referred to as PAN1 (control) or PAN2 (control)) or catalyst (referred to as PAN1 catalyst or PAN2 catalyst or PAN3 catalyst) comprising PAN fibres was added to the resultant mixture. The experiments were performed with or without air. If air was used, 2.5 L/min was supplied via. a filtered air pump and a sterilised Pyrex gas distribution tube.

After a specific contact time (see Tables below), 1 ml aliquots were removed from the experimental flask and transferred into 9 ml of neutraliser (catalase) for 5 minutes to inactivate any remaining hydrogen peroxide. After neutralisation, the number of micro-organisms present was enumerated using a modified Miles & Misra drop count method (Miles, A. A., & Misra, S. S. (1938). The estimation of the bactericidal power of blood. *Journal of Hygiene*, 38, 732-749). Briefly, 1 in 10 dilutions were performed and plated out onto nutrient agar in Petri dishes. The Petri dishes were incubated at 37° C. for 18 to 24 hours.

Following incubation, the number of colony forming units present on the agar was counted and used to calculate the $\log_{10}$ reduction in bacterial numbers caused by the experimental conditions. The number of $\log_{10}$ CFU/mL present in the resultant aliquot was calculated and subtracted from the number of $\log_{10}$ CFU/mL initially present at the start of the experiment in question. For example:

$$\text{Log}_{10} \text{ reduction in CFU/mL} = \text{Log}_{10a} - \text{Log}_{10b}$$

where $\text{Log}_{10a}$ is $\log_{10}$ of the number of CFU/mL present in the mixture at time zero (calculated from the number of CFU added to the flask and the dilution factor involved) and $\log_{10b}$ is $\log_{10}$ of the CFU present at a specific time point during the experiment. This is a typical method of assessing the activity of an antimicrobial; each log reduction represents a 90% reduction in the number of viable micro-organisms present, so a five log reduction represents a 99.999% reduction in bacterial numbers.

Testing for Antimicrobial Activity Against Spores

Spore suspensions were prepared based on the general principles of European quantitative suspension tests for evaluation of sporicidal activity (BS EN14347:2005: chemical disinfectants and antiseptics, basic sporicidal activity, test method and requirements (phase 1, step 1), London: British Standards Institute). Tryptone soya broth was seeded with spores from a previous batch and incubated at 37° C. to obtain an exponential growth phase culture. 10 mL of this culture was transferred into a Roux flask containing manganese-sulfate sporulation agar so that the inoculum came into contact with all of the surface of the agar. The Roux flasks were incubated at 37° C. for 2 days and for 21 days at 30° C., cultures were recovered, checked for sporulation and stored in water at 5° C. Sporicidal activity was then assessed using the method outlined previously (but with half the volume/weight of hydrogen peroxide, water, organism and catalyst) using 5 to 7.5% w/v hydrogen peroxide (see testing antimicrobial activity section). After neutralisation, a 1 mL sample was added to 12 to 15 mL of melted tryptone soya agar cooled to 45° C. Petri dishes were incubated for a minimum of 4 days and a maximum of 7 days at 37° C. and the $\log_{10}$ reduction in bacterial spore numbers calculated.

Antimicrobial Activity of PAN Catalyst Pre-Activated Hydrogen Peroxide 1 gram of PAN catalyst or PAN control was added to 67.5 mL of hydrogen peroxide, stirred for 1 hour and then removed. 7.5 ml of the washed bacterial suspension was added to the 67.5 ml of hydrogen peroxide to give a specific final concentration of hydrogen peroxide and approximately 8 $\log_{10}$ colony forming units (CFU)/mL of bacteria. The experiment was then conducted as outlined previously (see testing antimicrobial activity section).

Antimicrobial Activity of PAN Catalyst During Reuse

PAN catalyst was assessed for antimicrobial activity at first use, 48 hours after first use, 48 hours after second use and six months after first use using the same experimental conditions as described previously (see testing antimicrobial activity section).

Antimicrobial Activity of PAN Catalyst Under Buffered Neutral pH Conditions at Room Temperature and 35° C.

Experiments were conducted using the method outlined previously (see testing antimicrobial activity section), but hydrogen peroxide and catalyst were prepared in phosphate buffer solution. Experiments were carried out at room temperature and 35° C.

Results

About 8 $\log_{10}$ CFU/mL were present in the mixtures at time zero (the range over all experiments was 8.19-8.44 $\log_{10}$ CFU/mL). Control experiments established that the neutraliser was not toxic to the micro-organisms (8.10-8.69 $\log_{10}$ CFU/mL were present in the neutraliser toxicity controls compared to the 8.19-8.44 $\log_{10}$ CFU/mL originally added) and that it did nullify the activity of hydrogen peroxide (8.07-8.49 $\log_{10}$ CFU/mL were present in the neutraliser efficacy controls compared to the 8.19-8.44 $\log_{10}$ CFU/mL originally added).

Examples 1 to 11 show the mean log reduction in *Escherichia coli* ATCC 10536 numbers after exposure to experimental conditions. The results are provided in Table 1 below.

TABLE 1

Mean log reduction in *Escherichia coli* ATCC 10536 numbers after exposure to experimental conditions

| EG No. | Catalyst and/or PAN (1 g +/− 0.1) | $H_2O_2$ (% w/v) | 2.5 L/ minute of Air? | Mean $log_{10}$ reduction in CFU/ml (+/−S.D.) after a specified contact time | | | | | |
|---|---|---|---|---|---|---|---|---|---|
| | | | | 10 min | 20 min | 30 min | 40 min | 50 min | 60 min |
| 1 | PAN1 catalyst | 0.2 | Yes | 2.80 (0.82) | 4.95 (0.39) | >5.65 (0) | >5.65 (0) | >5.65 (0) | >5.65 (0) |
| 2 | PAN1 catalyst | 0 | Yes | 0.71 (0.35) | 0.98 (0.20) | 0.95 (0.22) | 1.19 (0.03) | 1.04 (0.11) | 1.14 (0.22) |
| 3 | PAN1 control | 0.2 | Yes | 0.42 (0.37) | 1.70 (0.39) | 3.10 (0.17) | 3.62 (0) | 4.6 (0.35) | >5.50 (0) |
| 4 | PAN1 control | 0 | Yes | 0.22 (0.05) | 0.07 (0.19) | −0.09* (0.06) | −0.01 (0.17) | −0.34 (0.26) | 0.31 (0.12) |
| 5 | None | 0.2 | Yes | 1.33 (0.27) | 2.68 (0.22) | 3.98 (0.28) | 4.79 (0.43) | >5.58 (0) | >5.58 (0) |
| 6 | None | 0 | Yes | 0.18 (0.06) | 0.17 (0.24) | 0.27 (0.34) | 0.33 (0.20) | 0.05 (0) | 0.02 (0.09) |
| 7 | None | 0.2 | No | 1.01 (0.36) | 2.20 (0.42) | 2.67 (0.52) | 3.52 (0.57) | 4.21 (0.19) | 4.76 (0.39) |
| 8 | PAN2 catalyst | 0.2 | Yes | 3.14 (1.01) | ≧5.30 (0.28) | >5.46 (0) | >5.46 (0) | >5.46 (0) | >5.46 (0) |
| 9 | PAN2 catalyst | 0.2 | No | 2.28 (0.13) | 4.79 (0.06) | >5.46 (0) | >5.46 (0) | >5.46 (0) | >5.46 (0) |
| 10 | PAN2 control | 0.2 | Yes | 0.44 (0.02) | 1.36 (0.08) | 2.33 (0.09) | 2.79 (0.23) | 3.57 (0.04) | >5.56 (0) |
| 11 | PAN2 control | 0.2 | No | 0.52 (0.04) | 2.45 (0.22) | 3.55 (0.16) | >5.56 (0) | >5.56 (0) | >5.56 (0) |

*negative values represent an increase in CFU/ml

Example 1 shows the activity of PAN1 catalyst against *Escherichia coli* in the presence of 0.2% w/v hydrogen peroxide and air. A 4.95 log reduction was recorded after 20 minutes and a greater than 5 log reduction was seen after 30 minutes (compared to 50 minutes in example 5, which used no catalyst, and to 40 minutes in example 44, which shows exposure to acidic hydrogen peroxide and air only).

Example 2 shows the activity of PAN1 catalyst against *Escherichia coli* in the presence of air (no hydrogen peroxide). A 1.14 log reduction was seen after 60 minutes (compared to a 0.31 log reduction seen after 60 minutes in example 4, which used PAN control and air only, and compared to a 0.02 log reduction seen after 60 minutes in example 6, which used no catalyst).

Example 3 shows the activity of PAN1 control against *Escherichia coli* in the presence of 0.2% w/v hydrogen peroxide and air. There was no increase in activity compared to the hydrogen peroxide controls described in examples 5 and 7.

Example 4 shows the activity of PAN1 control against *Escherichia coli* in the presence of air. No significant activity was recorded.

Example 5 shows the activity of 0.2% w/v hydrogen peroxide against *Escherichia coli* in the presence of air. A greater than 5 log reduction was seen after 50 minutes exposure time.

Example 6 shows the activity of air against *Escherichia coli*. A 0.33 log reduction or less was recorded.

Example 7 shows the activity of 0.2% w/v hydrogen peroxide against *Escherichia coli*. A 4.76 log reduction was seen after 60 minutes exposure time.

Example 8 shows the activity of PAN2 catalyst against *Escherichia coli* in the presence of 0.2% w/v hydrogen peroxide and air. A greater than 5 log reduction was seen after 20 minutes (compared to 50 minutes in example 5, which used no catalyst, and 40 minutes in example 44, which shows exposure to acidic hydrogen peroxide and air only). A 3.14 log reduction was recorded after 10 minutes for Example 8.

Example 9 shows the activity of PAN2 catalyst against *Escherichia coli* in the presence of 0.2% w/v hydrogen peroxide. A greater than 5 log reduction was seen after 30 minutes (compared to 40 minutes in example 41, which shows exposure to acidic hydrogen peroxide only, and a 4.76 log reduction after 60 minutes in example 7, which used no catalyst). A 4.79 log reduction was recorded after 20 minutes.

Example 10 shows the activity of PAN2 control against *Escherichia coli* in the presence of 0.2% w/v hydrogen peroxide and air. No increase in activity was seen compared to the hydrogen peroxide and air results shown in example 5.

Example 11 shows the activity of PAN2 control against *Escherichia coli* in the presence of 0.2% w/v hydrogen perdxide. An increase in activity (5 log reduction in 40 minutes) was seen compared to the hydrogen peroxide results shown in example 7 (no catalyst used; 4.76 log reduction in 60 minutes), but this was less than the increase seen with PAN2 catalyst in examples 8 and 9 and is comparable to the effect of acidic hydrogen peroxide (see example 41).

Examples 12 to 23 show mean log reduction in *Pseudomonas aeruginosa* ATCC 15442 numbers after exposure to experimental conditions. The results are shown in Table 2 below.

TABLE 2

Mean log reduction in *Pseudomonas aeruginosa* ATCC 15442 numbers after exposure to experimental conditions

| EG No. | Catalyst and/or PAN (1 g +/− 0.1) | $H_2O_2$ (% w/v) | 2.5 L/ minute of Air? | Mean $log_{10}$ reduction in CFU/ml (+/−S.D.) after a specified contact time | | | | | |
|---|---|---|---|---|---|---|---|---|---|
| | | | | 10 min | 20 min | 30 min | 40 min | 50 min | 60 min |
| 12 | PAN1 catalyst | 0.5 | Yes | 5.17 (0.56) | >5.74 (0) | >5.74 (0) | >5.74 (0) | >5.74 (0) | >5.74 (0) |
| 13 | PAN1 catalyst | 0 | Yes | 1.16* | 1.88 | 2.30 | 2.64 | 2.58 | 3.00 |
| 14 | PAN1 catalyst | 0.5 | No | 4.72 (0.39) | >5.74 (0) | >5.74 (0) | >5.74 (0) | >5.74 (0) | >5.74 (0) |
| 15 | PAN1 control | 0.5 | Yes | 0.66 (0.17) | 0.80 (0.13) | 0.94 (0.18) | 0.89 (0.31) | 0.99 (0.15) | 1.05 (0.07) |
| 16 | PAN1 control | 0 | Yes | −0.02 (0.07) | 0.06 (0.09) | 0.08 (0.06) | 0.06 (0.09) | 0.02 (0.05) | 0.08 (0.06) |
| 17 | None | 0.5 | Yes | 0.36 (0.13) | 0.53 (0.10) | 0.55 (0.18) | 0.59 (0) | 0.72 (0.07) | 0.50 (0.09) |
| 18 | None | 0 | Yes | 0.40 (0.09) | 0.19 (0) | 0.48 (0.05) | 0.21 (0.21) | 0.29 (0.17) | 0.23 (0.07) |
| 19 | None | 0.5 | No | 0.52 (0.12) | 0.81 (0.24) | 0.88 (0.25) | 0.86 (0.32) | 0.87 (0.28) | 0.97 (0.22) |
| 20 | PAN2 catalyst | 0.5 | Yes | ≧5.39 (0) | >5.59 (0) | >5.59 (0) | >5.59 (0) | >5.59 (0) | >5.59 (0) |
| 21 | PAN2 catalyst | 0.5 | No | 4.78 (0.46) | >5.59 (0) | >5.59 (0) | >5.59 (0) | >5.59 (0) | >5.59 (0) |

TABLE 2-continued

Mean log reduction in *Pseudomonas aeruginosa* ATCC 15442 numbers after exposure to experimental conditions

| EG No. | Catalyst and/or PAN (1 g +/- 0.1) | $H_2O_2$ (% w/v) | 2.5 L/minute of Air? | Mean $\log_{10}$ reduction in CFU/ml (+/-S.D.) after a specified contact time | | | | | |
|---|---|---|---|---|---|---|---|---|---|
| | | | | 10 min | 20 min | 30 min | 40 min | 50 min | 60 min |
| 22 | PAN2 control | 0.5 | Yes | 0.63 (0.03) | 1.05 (0.16) | 0.90 (0.22) | 1.10 (0.15) | 0.85 (0.12) | 0.73 (0.07) |
| 23 | PAN2 control | 0.5 | No | 1.00 (0.31) | 1.08 (0.16) | 1.22 (0.22) | 1.24 (0.02) | 1.25 (0.18) | 1.19 (0.08) |

*one set of results only

Example 12 shows the activity of PAN1 catalyst against *Pseudomonas aeruginosa* in the presence of 0.5% w/v hydrogen peroxide and air. A greater than 5 log reduction was seen after 10 minutes (compared to a 0.5 log reduction after 60 minutes in example 17, which used no catalyst, and a 5 log reduction after 50 minutes in example 45, which shows exposure to acidic hydrogen peroxide and air only).

Example 13 shows the activity of PAN1 catalyst against *Pseudomonas aeruginosa* in the presence of air. A 3 log reduction was seen after 60 minutes (compared to a 0.23 log reduction seen after 60 minutes in example 18, which used no catalyst) but only one set of experiments were performed. This activity may be due at least in part to a fall in pH, as a 1.51 log reduction was seen in the acid pH with air control (see example 39).

Example 14 shows the activity of PAN1 catalyst against *Pseudomonas aeruginosa* in the presence of 0.5% w/v hydrogen peroxide. A greater than 5 log reduction was seen after 20 minutes (compared to a 0.97 log reduction after 60 minutes in example 19, which used no catalyst, and a 4.83 log reduction after 60 minutes in example 42, which shows exposure to acidic hydrogen peroxide only). A 4.72 log reduction was seen after 10 minutes.

Example 15 shows the activity of PAN1 control against *Pseudomonas aeruginosa* in the presence of 0.5% w/v hydrogen peroxide and air. A 1.05 log reduction was recorded after 60 minutes (compared to the greater than 5 log reduction seen with example 45, which shows exposure to acidic hydrogen peroxide and air only, and the maximum log reduction of 0.72 seen in example 17, which used no catalyst).

Example 16 shows the activity of PAN1 control against *Pseudomonas aeruginosa* in the presence of air. No significant activity was recorded.

Example 17 shows the activity of 0.5% w/v hydrogen peroxide against *Pseudomonas aeruginosa* in the presence of air. A 0.5 log reduction was seen after 60 minutes exposure time. The maximum log reduction seen was 0.72 after 50 minutes.

Example 18 shows the activity of air against *Pseudomonas aeruginosa*. No significant activity (less than a 0.5 log reduction) was recorded.

Example 19 shows the activity of 0.5% w/v hydrogen peroxide against *Pseudomonas aeruginosa*. A 0.97 log reduction was seen after 60 minutes exposure time.

Example 20 shows the activity of PAN2 catalyst against *Pseudomonas aeruginosa* in the presence of 0.5% w/v hydrogen peroxide and air. A greater than 5 log reduction was seen after 10 minutes (compared to a 0.5 log reduction after 60 minutes in example 17, which used no catalyst, and a greater than 5 log reduction after 50 minutes in example 45, which shows exposure to acidic hydrogen peroxide and air only).

Example 21 shows the activity of PAN2 catalyst against *Pseudomonas aeruginosa* in the presence of 0.5% w/v hydrogen peroxide. A greater than 5 log reduction was seen after 20 minutes (compared to a 0.97 log reduction after 60 minutes in example 19, which used no catalyst, and a 4.83 log reduction after 60 minutes in example 42, which shows exposure to acidic hydrogen peroxide only). A 4.78 log reduction was recorded after 10 minutes.

Example 22 shows the activity of PAN2 control against *Pseudomonas aeruginosa* in the presence of 0.5% w/v hydrogen peroxide and air. Similar activity was seen compared to the hydrogen peroxide and air results shown in example 17.

Example 23 shows the activity of PAN2 control against *Pseudomonas aeruginosa* in the presence of 0.5% w/v hydrogen peroxide. The largest log reduction recorded was 1.25 at 50 minutes.

Examples 24 to 34 show the mean log reduction in *Staphylococcus aureus* ATCC 6538 numbers after exposure to experimental conditions. The results are shown in Table 3 below.

TABLE 3

Mean log reduction in *Staphylococcus aureus* ATCC 6538 numbers after exposure to experimental conditions

| EG No. | Catalyst and/or PAN (1 g +/- 0.1) | $H_2O_2$ (% w/v) | 2.5 L/minute of Air? | Mean $\log_{10}$ reduction in CFU/ml (+/-S.D.) after a specified contact time | | | | | |
|---|---|---|---|---|---|---|---|---|---|
| | | | | 10 min | 20 min | 30 min | 40 min | 50 min | 60 min |
| 24 | PAN1 catalyst | 1 | Yes | >5.64 (0) | >5.64 (0) | >5.64 (0) | >5.64 (0) | >5.64 (0) | >5.64 (0) |
| 25 | PAN1 catalyst | 1 | No | >5.64 (0) | >5.64 (0) | >5.64 (0) | >5.64 (0) | >5.64 (0) | >5.64 (0) |
| 26 | PAN1 control | 1 | Yes | 0.35 (0.09) | 1.07 (0.60) | 2.21 (0.61) | 2.93 (0.85) | 4.39 (0.82) | 5.17 (0.51) |
| 27 | PAN1 control | 0 | Yes | 0.50 (0.08) | 0.62 (0.17) | 0.69 (0.11) | 0.60 (0.14) | 0.59 (0.09) | 0.57 (0.09) |
| 28 | None | 1 | Yes | 0.61 (0.09) | 1.27 (0.64) | 2.57 (0.44) | 3.84 (0.15) | 5.07 (0.21) | 5.40 (0.17) |

TABLE 3-continued

Mean log reduction in *Staphylococcus aureus* ATCC 6538 numbers after exposure to experimental conditions

| Catalyst EG and/or PAN | $H_2O_2$ | 2.5 L/minute | Mean $log_{10}$ reduction in CFU/ml (+/−S.D.) after a specified contact time | | | | | |
|---|---|---|---|---|---|---|---|---|
| No. (1 g +/− 0.1) | (% w/v) | of Air? | 10 min | 20 min | 30 min | 40 min | 50 min | 60 min |
| 29 None | 0 | Yes | 0.61 (0.10) | 0.75 (0.05) | 0.66 (0.06) | 0.56 (0.21) | 0.40 (0.02) | 0.46 (0.08) |
| 30 None | 1 | No | 0.70 (0.18) | 1.43 (0.75) | 2.88 (0.99) | 3.89 (0.66) | 4.97 (0.65) | 5.37 (0.40) |
| 31 PAN2 catalyst | 1 | Yes | 3.13 (0.20) | >5.36 (0) | >5.36 (0) | >5.36 (0) | >5.36 (0) | >5.36 (0) |
| 32 PAN2 catalyst | 1 | No | 3.58 (0.58) | >5.36 (0) | >5.36 (0) | >5.36 (0) | >5.36 (0) | >5.36 (0) |
| 33 PAN2 control | 1 | Yes | 1.39 (0.28) | 3.10 (0.07) | 3.78 (0.19) | 4.78 (0) | >5.48 (0) | >5.48 (0) |
| 34 PAN2 control | 1 | No | 0.96 (0.07) | 3.09 (0.09) | 4.09 (0.06) | ≧5.32 (0.28) | >5.48 (0) | >5.48 (0) |

* one set of results only

Example 24 shows the activity of PAN1 catalyst against *Staphylococcus aureus* in the presence of 1% w/v hydrogen peroxide and air. A greater than 5 log reduction was seen after 10 minutes (compared to 50 minutes in example 28, which used no catalyst, and compared to a 3.45 log reduction after 60 minutes in example 46, which shows exposure to acidic hydrogen peroxide and air only).

Example 25 shows the activity of PAN1 catalyst against *Staphylococcus aureus* in the presence of 1% w/v hydrogen peroxide. A greater than 5 log reduction was seen after 10 minutes (compared to 60 minutes in example 30, which used no catalyst, and compared to a 3.23 log reduction after 60 minutes in example 43, which shows exposure to acidic hydrogen peroxide only).

Example 26 shows the activity of PAN1 control against *Staphylococcus aureus* in the presence of 1% w/v hydrogen peroxide and air. A 5 log reduction was recorded after 60 minutes and the results were similar to those seen in example 28.

Example 27 shows the activity of PAN1 control against *Staphylococcus aureus* in the presence of air. Less than a 0.7 log reduction was seen at all time points which is comparable to example 29 (air only).

Example 28 shows the activity of 1% w/v hydrogen peroxide against *Staphylococcus aureus* in the presence of air. A 5 log reduction was seen after 50 minutes exposure time.

Example 29 shows the activity of air against *Staphylococcus aureus*. Less than a 0.8 log reduction was seen at all time points.

Example 30 shows the activity of 1% w/v hydrogen peroxide against *Staphylococcus aureus*. A 5 log reduction was seen after 60 minutes exposure time.

Example 31 shows the activity of PAN2 catalyst against *Staphylococcus aureus* in the presence of 1% w/v hydrogen peroxide and air. A greater than 5 log reduction was seen after 20 minutes (compared to a 5 log reduction after 50 minutes in examples 28 and 33 and compared to a 3.45 log reduction after 60 minutes in example 46, which shows exposure to acidic hydrogen peroxide and air only).

Example 32 shows the activity of PAN2 catalyst against *Staphylococcus aureus* in the presence of 1% w/v hydrogen peroxide. A greater than 5 log reduction was seen after 20 minutes (compared to a 5 log reduction after 40 and 60 minutes in examples 34 and 30 respectively and compared to a 3.23 log reduction after 60 minutes in example 43, which shows exposure to acidic hydrogen peroxide only). A 3.58 log reduction was recorded after 10 minutes.

Example 33 shows the activity of PAN2 control against *Staphylococcus aureus* in the presence of 1% w/v hydrogen peroxide and air. A 5 log reduction was seen after 50 minutes (which is comparable to example 28 (hydrogen peroxide and air)). A greater than 3 log reduction was seen after 20 minutes.

Example 34 shows the activity of PAN2 control against *Staphylococcus aureus* in the presence of 1% w/v hydrogen peroxide. A 5 log reduction was seen after 40 minutes (compared to 60 minutes in example 30, which used no catalyst and 20 minutes in example 32 (PAN2 catalyst with hydrogen peroxide)).

Examples 35 to 46 are control examples and show the effect of acidic conditions on the survival of bacteria. The results are shown in Table 4 below.

TABLE 4

Mean log reduction in bacterial numbers after exposure to acidic experimental conditions

| EG | Micro- | $H_2O_2$ | 2.5 L/minute | Mean $log_{10}$ reduction in CFU/ml (+/−S.D.) after a specified contact time | | | | | |
|---|---|---|---|---|---|---|---|---|---|
| No. | organism | (% w/v) | of Air? | 10 min | 20 min | 30 min | 40 min | 50 min | 60 min |
| 35 | *Escherichia coli* | 0 | No | 0.04 (0.4) | 0.18 (3.40) | 0.21 (0.10) | 0.56 (0.44) | 0.47 (0.25) | 0.59 (0.12) |
| 36 | *Pseudomonas aeruginosa* | 0 | No | 0.71 (0.29) | 0.61 (0.15) | 1.00 (0.58) | 0.95 (0.49) | 1.24 (0.60) | 1.41 (0.98) |
| 37 | *Staphylococcus aureus* | 0 | No | 0.53 (0.10) | 0.60 (0.07) | 0.59 (0.26) | 0.73 (0.09) | 0.61 (0.20) | 0.63 (0.29) |
| 38 | *Escherichia coli* | 0 | Yes | 0.29 (0.23) | 0.28 (0.08) | 0.28 (0.20) | 0.58 (0.23) | 0.63 (0.41) | 0.37 (0.09) |

TABLE 4-continued

Mean log reduction in bacterial numbers after exposure to acidic experimental conditions

| EG No. | Micro-organism | $H_2O_2$ (% w/v) | 2.5 L/minute of Air? | Mean $log_{10}$ reduction in CFU/ml (+/−S.D.) after a specified contact time | | | | | |
|---|---|---|---|---|---|---|---|---|---|
| | | | | 10 min | 20 min | 30 min | 40 min | 50 min | 60 min |
| 39 | Pseudomonas aeruginosa | 0 | Yes | 0.67 (0.23) | 1.19 (0.52) | 1.19 (0.58) | 1.10 (0.31) | 1.37 (0.39) | 1.51 (0.86) |
| 40 | Staphylococcus aureus | 0 | Yes | 1.00 (0.68) | 1.20 (0.67) | 1.27 (0.61) | 1.21 (0.91) | 1.29 (0.80) | 1.44 (0.88) |
| 41 | Escherichia coli | 0.2 | No | 2.43 (0.47) | 3.40 (0.71) | 4.21 (0.91) | ≧5.11 (0.60) | ≧5.30 (0.28) | >5.46 (0) |
| 42 | Pseudomonas aeruginosa | 0.5 | No | 2.30 (0.78) | 2.76 (0.88) | 3.71 (1.09) | 3.88 (0.66) | 4.52 (0.92) | 4.83 (0.64) |
| 43 | Staphylococcus aureus | 1 | No | 0.69 (0.26) | 0.72 (0.26) | 1.30 (0.12) | 2.03 (0.30) | 2.90 (0.23) | 3.23 (0.47) |
| 44 | Escherichia coli | 0.2 | Yes | 2.16 (0.61) | 3.35 (0.41) | 4.46 (0.50) | ≧5.46 (0) | >5.46 (0) | >5.46 (0) |
| 45 | Pseudomonas aeruginosa | 0.5 | Yes | 2.53 (0.82) | 3.41 (0.85) | 4.25 (0.79) | ≧4.81 (0.66) | ≧5.34 (0.17) | ≧5.34 (0.35) |
| 46 | Staphylococcus aureus | 1 | Yes | 1.00 (0.24) | 1.86 (0.82) | 2.33 (0.94) | 2.83 (0.99) | 2.23 (0.99) | 3.45 (0.97) |

Example 35 shows the effect of acidic conditions on the survival of *Escherichia coli*. A 0.59 log reduction was seen after 60 minutes.

Example 36 shows the effect of acidic conditions on the survival of *Pseudomonas aeruginosa*. A 1.41 log reduction was seen after 60 minutes.

Example 37 shows the effect of acidic conditions on the survival of *Staphylococcus aureus*. The largest log reduction recorded was 0.73 after 40 minutes.

Example 38 shows the effect of acidic conditions and air on the survival of *Escherichia coli*. The largest log reduction recorded was 0.63 after 50 minutes.

Example 39 shows the effect of acidic conditions and air on the survival of *Pseudomonas aeruginosa*. A 1.51 log reduction was recorded after 60 minutes.

Example 40 shows the effect of acidic conditions and air on the survival of *Staphylococcus aureus*. A 1.44 log reduction was recorded after 60 minutes.

Example 41 shows the effect, of acidic conditions on the survival of *Escherichia coli* in the presence of 0.2% w/v hydrogen peroxide. A greater than 5 log reduction was seen after 40 minutes.

Example 42 shows the effect of acidic conditions on the survival of *Pseudomonas aeruginosa* in the presence of 0.5% w/v hydrogen peroxide. A 4.83 log reduction was seen after 60 minutes.

Example 43 shows the effect of acidic conditions on the survival of *Staphylococcus aureus* in the presence of 1% w/v hydrogen peroxide. A 3.23 log reduction was recorded after 60 minutes.

Example 44 shows the effect of acidic conditions, 0.2% w/v hydrogen peroxide and air on the survival of *Escherichia coli*. A greater than 5 log reduction was seen after 40 minutes.

Example 45 shows the effect of acidic conditions, 0.5% w/v hydrogen peroxide and air on the survival of *Pseudomonas aeruginosa*. A greater than 5 log reduction was seen after 50 minutes Example 46 shows the effect of acidic conditions, 1% w/v hydrogen peroxide and air on the survival of *Staphylococcus aureus*. A 3.45 log reduction was recorded after 60 minutes.

In conclusion, the modified PAN fibre (without metal cation fixed thereto) has no effect or a lower effect on the survival of micro-organisms than the catalyst comprising PAN fibres (i.e. is less effective at killing the micro-organisms). A decrease in pH is not responsible for the full activity of the catalyst. This is shown by examples 35 to 46 in comparison to examples 1 to 34.

The catalyst comprising PAN fibre in combination with a peroxygen compound, such as hydrogen peroxide, results in greater activity against micro-organisms, including *Escherichia coli*, *Pseudomonas aeruginosa* and *Staphylococcus aureus*, than the use of hydrogen peroxide alone (see examples 9, 14, 21, 25 and 32).

The catalyst comprising PAN fibre in combination with a peroxygen compound, such as hydrogen peroxide, and air results in greater activity against micro-organisms, including *Escherichia coli*, *Pseudomonas aeruginosa* and *Staphylococcus aureus*, than the use of hydrogen peroxide alone (see examples 1, 8, 12, 20, 24 and 31).

Examples 47 to 52 show the mean log reduction in *Bacillus subtilis* subsp. *spizizenii* ATCC 6633 spore numbers after exposure to experimental conditions. The results are provided in Table 5 below.

TABLE 5

Mean log reduction in *Bacillus subtilis* subsp. *spizizenii* ATCC 6633 spore numbers after exposure to experimental conditions

| EG No. | Catalyst and/or PAN (1 g +/− 0.1) | $H_2O_2$ (% w/v) | 2.5 L/minute of Air? | Mean $log_{10}$ reduction in CFU/ml (+/−S.D.) after a specified contact time | | | |
|---|---|---|---|---|---|---|---|
| | | | | 10 min | 30 min | 60 min | 120 min |
| 47 | PAN3 catalyst | 5 | No | 1.00 (0.60) | 1.33 (0.56) | 2.91 (0.37) | 4.91 (0.90) |
| 48 | PAN2 catalyst | 5 | No | 0.23 (0.08) | 0.49 (0.04) | 1.62 (0.31) | >6.84 (0.00) |
| 49 | None | 5 | No | 1.02 (0.03) | 1.26 (0.12) | 1.90 (0.09) | 3.45 (0.27) |

TABLE 5-continued

Mean log reduction in *Bacillus subtilis* subsp. *spizizenii* ATCC 6633 spore numbers after exposure to experimental conditions

| Catalyst EG and/or PAN No. (1 g +/− 0.1) | $H_2O_2$ (% w/v) | 2.5 L/minute of Air? | Mean $\log_{10}$ reduction in CFU/ml (+/−S.D.) after a specified contact time | | | |
|---|---|---|---|---|---|---|
| | | | 10 min | 30 min | 60 min | 120 min |
| 50 PAN3 catalyst | 7.5 | No | 0.28 (0.17) | 0.95 (0.14) | 2.50 (0.16) | >6.84 (0.00) |
| 51 PAN2 catalyst | 7.5 | No | 1.48 (0.06) | 2.41 (0.08) | ≧6.28 (0.54) | >6.84 (0.00) |
| 52 None | 7.5 | No | 0.04 (0.11) | 0.19 (0.08) | 0.95 (0.01) | 4.22 (0.71) |

Example 47 shows the activity of the PAN3 catalyst against *Bacillus subtilis* spores in the presence of 5% w/v hydrogen peroxide. A 4.91 log reduction was seen after 120 minutes exposure time (compared to a 3.45 log reduction after 120 minutes in example 49, which used no catalyst).

Example 48 shows the activity of the PAN2 catalyst against *Bacillus subtilis* spores in the presence of 5% w/v hydrogen peroxide. A greater than 6.84 log reduction was seen after 120 minutes exposure time (compared to a 3.45 log reduction after 120 minutes in example 49, which used no catalyst).

Example 49 shows the activity of 5% w/v hydrogen peroxide against *Bacillus subtilis* spores. A 3.45 log reduction was seen after 120 minutes.

Example 50 shows the activity of the PAN3 catalyst against *Bacillus subtilis* spores in the presence of 7.5% w/v hydrogen peroxide. A greater than 6.84 log reduction was seen after 120 minutes exposure time (compared to a 4.22 log reduction after 120 minutes in example 52, which used no catalyst).

Example 51 shows the activity of the PAN2 catalyst against *Bacillus subtilis* spores in the presence of 7.5% w/v hydrogen peroxide. A greater than 6.28 log reduction was seen after 60 minutes exposure time (compared to a 0.95 log reduction after 60 minutes in example 52, which used no catalyst).

Example 52 shows the activity of 7.5% w/v hydrogen peroxide against *Bacillus subtilis* spores. A 4.22 log reduction was seen after 120 minutes.

Examples 53 to 61 show the mean log reduction in *Escherichia coli* numbers after exposure to experimental conditions on repeated occasions with reuse of the catalyst at room temperature. The results are provided in Table 6 below.

TABLE 6

Mean log reduction in *Escherichia coli* ATCC 10536 numbers after exposure to experimental conditions with and without reuse of the catalyst at room temperature.

| Catalyst EG and/or PAN No. (1 g +/− 0.1) | $H_2O_2$ (% w/v) | 2.5 L/minute of Air? | Reuse of catalyst time from $1^{st}$ use | Mean $\log_{10}$ reduction in CFU/ml (+/−S.D.) after a specified contact time | | | | | |
|---|---|---|---|---|---|---|---|---|---|
| | | | | 10 min | 20 min | 30 min | 40 min | 50 min | 60 min |
| 53 None | 0.2 | No | — | 1.01 (0.19) | 2.08 (0.12) | 3.28 (0.08) | 4.00 (0.02) | 5.17 (0.35) | >5.50 (0.00) |
| 54 PAN2 catalyst | 0.2 | No | $1^{st}$ use | 1.62 (0.09) | 4.74 (0.25) | >5.50 (0.00) | >5.50 (0.00) | >5.50 (0.00) | >5.50 (0.00) |
| 55 PAN2 catalyst | 0.2 | No | $2^{nd}$ use$^a$ | 2.14 (0.03) | 3.32 (0.07) | 4.67 (0.13) | >5.50 (0.00) | >5.50 (0.00) | >5.50 (0.00) |
| 56 PAN2 catalyst | 0.2 | No | $3^{rd}$ use$^b$ | 1.41 (0.06) | 2.73 (0.02) | 3.66 (0.10) | 4.61 (0.36) | >5.50 (0.00) | >5.50 (0.00) |
| 57 PAN3 catalyst | 0.2 | No | $1^{st}$ use | 1.84 (0.42) | 3.38 (0.48) | ≧5.22 (0.48) | >5.50 (0.00) | >5.50 (0.00) | >5.50 (0.00) |
| 58 PAN3 catalyst | 0.2 | No | $2^{nd}$ use$^a$ | 1.97 (0.30) | 3.56 (0.43) | 4.98 (0.54) | >5.50 (0.00) | >5.50 (0.00) | >5.50 (0.00) |
| 59 PAN3 catalyst | 0.2 | No | $3^{rd}$ use$^b$ | 2.25 (0.22) | 3.64 (0.07) | 4.76 (0.12) | >5.50 (0.00) | >5.50 (0.00) | >5.50 (0.00) |
| 60 PAN1 catalyst | 0.2 | Yes | $1^{st}$ use | 2.80 (0.82) | 4.95 (0.39) | >5.65 (0.00) | >5.65 (0.00) | >5.65 (0.00) | >5.65 (0.00) |
| 61 PAN1 catalyst | 0.2 | Yes | $2^{nd}$ use$^c$ | 3.26 (0.46) | >5.65 (0.00) | >5.65 (0.00) | >5.65 (0.00) | >5.65 (0.00) | >5.65 (0.00) |

$^a$ = 48 hours after $1^{st}$ use;
$^b$ = 48 hours after $2^{nd}$ use;
$^c$ = 6 months from $1^{st}$ use Example 53 shows the activity of the 0.2% w/v hydrogen peroxide against *Escherichia coli* at room temperature. A 5.17 log reduction was seen after 50 minutes exposure time.

Example 54 shows the activity of the PAN 2 catalyst during its first use against *Escherichia coli* in the presence of 0.2% w/v hydrogen peroxide at room temperature. A greater than 5.50 log reduction was seen after 30 minutes exposure time (compared to a 3.28 log reduction after 30 minutes in example 53).

Example 55 shows the activity of the PAN 2 catalyst during its second use (48 hours after use in example 54) against *Escherichia coli* in the presence of 0.2% w/v hydrogen peroxide at room temperature. A 4.67 log reduction was seen after 30 minutes exposure time (compared to a 3.28 log reduction after 30 minutes in example 53).

Example 56 shows the activity of the PAN 2 catalyst during its third use (48 hours after use in example 55) against

*Escherichia coli* in the presence of 0.2% w/v hydrogen peroxide at room temperature. A 3.66 log reduction was seen after 30 minutes exposure time (compared to a 3.28 log reduction after 30 minutes in example 53).

Example 57 shows the activity of the PAN 3 catalyst during its first use against *Escherichia coli* in the presence of 0.2% w/v hydrogen peroxide at room temperature. A greater than or equal to 5.22 log reduction was seen after 30 minutes exposure time (compared to a 3.28 log reduction after 30 minutes in example 53).

Example 58 shows the activity of the PAN 3 catalyst during its second use (48 hours after use in example 57) against *Escherichia coli* in the presence of 0.2% w/v hydrogen peroxide at room temperature. A 4.98 log reduction was seen after 30 minutes exposure time (compared to a 3.28 log reduction after 30 minutes in example 53).

Example 59 shows the activity of the PAN 3 catalyst during its third use (48 hours after use in example 58) against *Escherichia coli* in the presence of 0.2% w/v hydrogen peroxide at room temperature. A 4.76 log reduction was seen after 30 minutes exposure time (compared to a 3.28 log reduction after 30 minutes in example 53).

Example 60 shows the activity of the PAN 1 catalyst during its first use against *Escherichia coli* in the presence of 0.2% w/v hydrogen peroxide and air at room temperature. A greater than 5.65 log reduction was seen after 30 minutes exposure time (compared to a 3.28 log reduction after 30 minutes in example 53).

Example 61 shows the activity of the PAN 1 catalyst during its second use (6 months after use in example 60) against *Escherichia coli* in the presence of 0.2% w/v hydrogen peroxide at room temperature. A greater than 5.65 log reduction was seen after 20 minutes exposure time (compared to a 2.08 log reduction after 20 minutes in example 53).

Examples 62 to 70 show the mean log reduction in *Escherichia coli* numbers after exposure to experimental conditions on repeated occasions with reuse of the catalyst at 35° C. The results are provided in Table 7 below.

Example 62 shows the activity of the 0.2% w/v hydrogen peroxide against *Escherichia coli* at 35° C. A greater than or equal to 5.30 log reduction was seen after 30 minutes exposure time.

Example 63 shows the activity of the PAN 2 catalyst during its first use against *Escherichia coli* in the presence of 0.2% w/v hydrogen peroxide at 35° C. A greater than 5.50 log reduction was seen after 10 minutes exposure time (compared to 30 minutes for a greater than 5 log reduction in example 62).

Example 64 shows the activity of the PAN 2 catalyst during its second use (48 hours after use in example 63) against *Escherichia coli* in the presence of 0.2% w/v hydrogen peroxide at 35° C. A greater than 5.50 log reduction was seen after 20 minutes exposure time (compared to a 30 minutes for a greater than 5 log reduction in example 62).

Example 65 shows the activity of the PAN 2 catalyst during its third use (48 hours after use in example 64) against *Escherichia coli* in the presence of 0.2% w/v hydrogen peroxide at 35° C. A greater than 5.50 log reduction was seen after 20 minutes exposure time (compared to a 30 minutes for a greater than 5 log reduction in example 62).

Example 66 shows the activity of the PAN 3 catalyst during its first use against *Escherichia coli* in the presence of 0.2% w/v hydrogen peroxide at 35° C. A greater than 5.50 log reduction was seen after 20 minutes exposure time (compared to a 30 minutes for a greater than 5 log reduction in example 62).

Example 67 shows the activity of the PAN 3 catalyst during its second use (48 hours after use in example 66) against *Escherichia coli* in the presence of 0.2% w/v hydrogen peroxide at 35° C. A greater than 5.50 log reduction was seen after 20 minutes exposure time (compared to a 30 minutes for a greater than 5 log reduction in example 62).

Example 68 shows the activity of the PAN 3 catalyst during its third use (48 hours after use in example 67) against *Escherichia coli* in the presence of 0.2% w/v hydrogen peroxide at 35° C. A greater than 5.50 log reduction was seen

TABLE 7

Mean log reduction in *Escherichia coli* ATCC 10536 numbers after exposure to experimental conditions with and without reuse of the catalyst at 35° C.

| Catalyst EG and/or PAN No. (1 g +/− 0.1) | $H_2O_2$ (% w/v) | 2.5 L/minute of Air? | Reuse of catalyst time from 1st use | Mean $\log_{10}$ reduction in CFU/ml (+/−S.D.) after a specified contact time | | | | | |
|---|---|---|---|---|---|---|---|---|---|
| | | | | 10 min | 20 min | 30 min | 40 min | 50 min | 60 min |
| 62 None | 0.2 | No | — | 2.46 (0.32) | 3.77 (0.53) | ≧5.30 (0.35) | >5.50 (0.00) | >5.50 (0.00) | >5.50 (0.00) |
| 63 PAN 2 catalyst | 0.2 | No | 1st use | >5.50 (0.00) | >5.50 (0.00) | >5.50 (0.00) | >5.50 (0.00) | >5.50 (0.00) | >5.50 (0.00) |
| 64 PAN 2 catalyst | 0.2 | No | 2nd use[a] | 3.23 (0.06) | >5.50 (0.00) | >5.50 (0.00) | >5.50 (0.00) | >5.50 (0.00) | >5.50 (0.00) |
| 65 PAN 2 catalyst | 0.2 | No | 3rd use[b] | 3.34 (0.05) | >5.50 (0.00) | >5.50 (0.00) | >5.50 (0.00) | >5.50 (0.00) | >5.50 (0.00) |
| 66 PAN 3 catalyst | 0.2 | No | 1st use | 3.01 (0.06) | >5.50 (0.00) | >5.50 (0.00) | >5.50 (0.00) | >5.50 (0.00) | >5.50 (0.00) |
| 67 PAN 3 catalyst | 0.2 | No | 2nd use[a] | 3.30 (0.29) | >5.50 (0.00) | >5.50 (0.00) | >5.50 (0.00) | >5.50 (0.00) | >5.50 (0.00) |
| 68 PAN 3 catalyst | 0.2 | No | 3rd use[b] | 3.60 (0.18) | >5.50 (0.00) | >5.50 (0.00) | >5.50 (0.00) | >5.50 (0.00) | >5.50 (0.00) |
| 69 PAN 1 catalyst | 0.2 | Yes | 1st use | >5.53 (0.00) | >5.53 (0.00) | >5.53 (0.00) | >5.53 (0.00) | >5.53 (0.00) | >5.53 (0.00) |
| 70 PAN 1 catalyst | 0.2 | Yes | 2nd use[c] | >5.65 (0.00) | >5.65 (0.00) | >5.65 (0.00) | >5.65 (0.00) | >5.65 (0.00) | >5.65 (0.00) |

[a] = 48 hours after 1st use;
[b] = 48 hours after 2nd use;
[c] = 6 months from 1st use after 20 minutes exposure time (compared to a 30 minutes for a greater than 5 log reduction in example 62).

Example 69 shows the activity of the PAN 1 catalyst during its first use against *Escherichia coli* in the presence of 0.2% w/v hydrogen peroxide and air at 35° C. A greater than 5.53 log reduction was seen after 10 minutes exposure time (compared to a 30 minutes for a greater than 5 log reduction in example 62).

Example 70 shows the activity of the PAN 1 catalyst during its second use (6 months after use in example 69) against *Escherichia coli* in the presence of 0.2% w/v hydrogen peroxide at 35° C. A greater than 5.65 log reduction was seen after 10 minutes exposure time (compared to a 30 minutes for a greater than 5 log reduction in example 62).

Examples 71 to 76 show the mean log reduction in *Staphylococcus aureus* numbers after exposure to experimental conditions on repeated occasions with reuse of the catalyst at room temperature. The results are provided in Table 8 below.

*Staphylococcus aureus* in the presence of 1% w/v hydrogen peroxide at room temperature. A greater than 5.41 log reduction was seen after 30 minutes exposure time (compared to a 2.68 log reduction after 30 minutes in example 71).

Example 74 shows the activity of the PAN 2 catalyst during its third use (48 hours after use in example 73) against *Staphylococcus aureus* in the presence of 1% w/v hydrogen peroxide at room temperature. A greater than 5.41 log reduction was seen after 30 minutes exposure time (compared to a 2.68 log reduction after 30 minutes in example 71).

Example 75 shows the activity of the PAN 1 catalyst during its first use against *Staphylococcus aureus* in the presence of 1% w/v hydrogen peroxide and air at room temperature. A greater than 5.64 log reduction was seen after 10 minutes exposure time (compared to a 0.54 log reduction after 10 minutes in example 71).

Example 76 shows the activity of the PAN 1 catalyst during its second use (6 months after use in example 75) against

TABLE 8

Mean log reduction in *Staphylococcus aureus* ATCC 6538 numbers after exposure to experimental conditions with and without reuse of the catalyst at room temperature.

| Catalyst EG and/or PAN No. (1 g +/− 0.1) | $H_2O_2$ (% w/v) | 2.5 L/minute of Air? | Reuse of catalyst, time from $1^{st}$ use | Mean $\log_{10}$ reduction in CFU/ml (+/−S.D.) after a specified contact time | | | | | |
|---|---|---|---|---|---|---|---|---|---|
| | | | | 10 min | 20 min | 30 min | 40 min | 50 min | 60 min |
| 71 None | 1 | No | — | 0.54 (0.23) | 1.18 (0.55) | 2.68 (1.00) | 3.56 (0.41) | 4.62 (0.61) | 5.08 (0.35) |
| 72 PAN 2 catalyst | 1 | No | $1^{st}$ use | 1.66 (0.18) | >5.41 (0.00) | >5.41 (0.00) | >5.41 (0.00) | >5.41 (0.00) | >5.41 (0.00) |
| 73 PAN 2 catalyst | 1 | No | $2^{nd}$ use$^a$ | 1.26 (0.11) | 4.29 (0.23) | >5.41 (0.00) | >5.41 (0.00) | >5.41 (0.00) | >5.41 (0.00) |
| 74 PAN 2 catalyst | 1 | No | $3^{rd}$ use$^b$ | 1.01 (0.02) | 3.77 (0.03) | >5.41 (0.00) | >5.41 (0.00) | >5.41 (0.00) | >5.41 (0.00) |
| 75 PAN 1 catalyst | 1 | Yes | $1^{st}$ use | >5.64 (0.00) | >5.64 (0.00) | >5.64 (0.00) | >5.64 (0.00) | >5.64 (0.00) | >5.64 (0.00) |
| 76 PAN 1 catalyst | 1 | Yes | $2^{nd}$ use$^c$ | 0.97 (0.12) | 4.28 (0.09) | >5.68 (0.00) | >5.68 (0.00) | >5.68 (0.00) | >5.68 (0.00) |

$^a$= 48 hours after $1^{st}$ use;
$^b$= 48 hours after $2^{nd}$ use;
$^c$= 6 months from $1^{st}$ use Example 71 shows the activity of the 1% w/v hydrogen peroxide against *Staphylococcus aureus* at room temperature. A 5.08 log reduction was seen after 60 minutes exposure time.

Example 72 shows the activity of the PAN 2 catalyst during its first use against *Staphylococcus aureus* in the presence of 1% w/v hydrogen peroxide at room temperature. A greater than 5.41 log reduction was seen after 20 minutes exposure time (compared to a 1.18 log reduction after 20 minutes in example 71).

Example 73 shows the activity of the PAN 2 catalyst during its second use (48 hours after use in example 72) against *Staphylococcus aureus* in the presence of 1% w/v hydrogen peroxide at room temperature. A greater than 5.68 log reduction was seen after 30 minutes exposure time (compared to a 2.68 log reduction after 30 minutes in example 7).

Examples 77 to 80 show the mean log reduction in *Staphylococcus aureus* numbers after exposure to experimental conditions with and without catalyst and catalyst pre-activated hydrogen peroxide at room temperature. The results are provided in Table 9 below.

TABLE 9

Mean log reduction in *Staphylococcus aureus* ATCC 6538 numbers after exposure to experimental conditions with and without hydrogen peroxide pre-activated by catalyst or catalyst at room temperature.

| Catalyst EG and/or PAN No. (1 g +/− 0.1) | Catalyst or PAN mode of use | $H_2O_2$ (% w/v) | 2.5 L/minute of Air? | Mean $\log_{10}$ reduction in CFU/ml (+/−S.D.) after a specified contact time | | | | | |
|---|---|---|---|---|---|---|---|---|---|
| | | | | 10 min | 20 min | 30 min | 40 min | 50 min | 60 min |
| 77 None | — | 1 | No | 0.43 (0.23) | 1.21 (0.68) | 2.25 (0.44) | 3.92 (0.43) | 4.57 (0.51) | 5.10 (0.35) |
| 78 PAN 2 catalyst | Standard method of use | 1 | No | 1.95 (1.00) | >5.30 (0.00) | >5.30 (0.00) | >5.30 (0.00) | >5.30 (0.00) | >5.30 (0.00) |

TABLE 9-continued

Mean log reduction in *Staphylococcus aureus* ATCC 6538 numbers after exposure to experimental conditions with and without hydrogen peroxide pre-activated by catalyst or catalyst at room temperature.

| Catalyst EG and/or PAN No. (1 g +/− 0.1) | Catalyst or PAN mode of use | H₂O₂ (% w/v) | 2.5 L/minute of Air? | Mean log₁₀ reduction in CFU/ml (+/−S.D.) after a specified contact time | | | | | |
|---|---|---|---|---|---|---|---|---|---|
| | | | | 10 min | 20 min | 30 min | 40 min | 50 min | 60 min |
| 79 PAN 2 catalyst | Pre-activation method | 1 | No | 2.31 (0.45) | >5.30 (0.00) | >5.30 (0.00) | >5.30 (0.00) | >5.30 (0.00) | >5.30 (0.00) |
| 80 PAN 2 control | Pre-activation method | 1 | No | 0.42 (0.17) | 0.92 (0.06) | 1.93 (0.08) | 2.64 (0.10) | 2.81 (0.11) | 2.87 (0.07) |

Example 77 shows the activity of the 1% w/v hydrogen peroxide against *Staphylococcus aureus* at room temperature. A 5.10 log reduction was seen after 60 minutes exposure time.

mental starting pH ranged from 7.00 to 7.38 and the pH at the end of the experiment ranged from 6.99-7.38. The results are provided in Table 10 below.

TABLE 10

Mean log reduction in *Pseudomonas aeruginosa* ATCC 15442 numbers after exposure to experimental conditions with and without catalyst and buffered neutral pH conditions at room temperature.

| Catalyst EG and/or PAN No. (1 g +/− 0.1) | Buffered at neutral pH? | H₂O₂ (% w/v) | 2.5 L/minute of Air? | Mean log₁₀ reduction in CFU/ml (+/−S.D.) after a specified contact time | | | | | |
|---|---|---|---|---|---|---|---|---|---|
| | | | | 10 min | 20 min | 30 min | 40 min | 50 min | 60 min |
| 81 None | No | 0.5 | No | 0.58 (0.02) | 1.00 (0.26) | 1.00 (0.20) | 1.00 (0.32) | 1.02 (0.23) | 1.12 (0.20) |
| 82 None | No | 0.5 | Yes | 0.49 (0.06) | 0.70 (0.19) | 0.70 (0.09) | 0.80 (0.10) | 0.81 (0.00) | 0.63 (0.11) |
| 83 PAN 2 catalyst | No | 0.5 | No | 4.78 (0.46) | >5.59 (0.00) | >5.59 (0.00) | >5.59 (0.00) | >5.59 (0.00) | >5.59 (0.00) |
| 84 PAN 2 catalyst | No | 0.5 | Yes | >5.39 (0.35) | >5.59 (0.00) | >5.59 (0.00) | >5.59 (0.00) | >5.59 (0.00) | >5.59 (0.00) |
| 85 None | Yes | 0.5 | No | 1.08 (0.25) | 1.49 (0.37) | 1.69 (0.11) | 1.79 (0.07) | 1.92 (0.18) | 1.85 (0.24) |
| 86 None | Yes | 0.5 | Yes | 1.37 (0.04) | 1.46 (0.07) | 1.71 (0.32) | 1.61 (0.20) | 1.75 (0.10) | 1.90 (0.22) |
| 87 PAN 2 catalyst | Yes | 0.5 | No | 1.38 (0.45) | 1.79 (0.15) | 1.97 (0.11) | 2.08 (0.14) | 2.19 (0.17) | 2.25 (0.17) |
| 88 PAN 2 catalyst | Yes | 0.5 | Yes | 1.44 (0.25) | 1.81 (0.38) | 2.14 (0.45) | 2.29 (0.58) | 2.33 (0.54) | 2.43 (0.59) |

Example 78 shows the activity of the PAN 2 catalyst against *Staphylococcus aureus* in the presence of 1% w/v hydrogen peroxide at room temperature. A greater than 5.30 log reduction was seen after 20 minutes exposure time (compared to a 1.21 log reduction after 20 minutes in example 77).

Example 79 shows the activity of the PAN 2 catalyst using the pre-activation of hydrogen peroxide method against *Staphylococcus aureus* in the presence of 1% w/v hydrogen peroxide at room temperature. A greater than 5.30 log reduction was seen after 20 minutes exposure time (this is comparable to the log reduction seen in example 78 and is greater than the 1.21 log reduction after 20 minutes seen in example 77).

Example 80 shows the activity of the PAN 2 control using the pre-activation of hydrogen peroxide method against *Staphylococcus aureus* in the presence of 1% w/v hydrogen peroxide at room temperature. A 2.87 log reduction was seen, after 60 minutes exposure time (this is less than the 5.10 log reduction seen in example 77 after 60 minutes).

Examples 81 to 88 show the mean log reduction in *Pseudomonas aeruginosa* numbers after exposure to experimental conditions with and without catalyst and under buffered neutral pH conditions at room temperature. The experi- Example 81 shows the activity of the 0.5% w/v hydrogen peroxide against *Pseudomonas aeruginosa* at room temperature. A 1.12 log reduction was seen after 60 minutes exposure time.

Example 82 shows the activity of the 0.5% w/v hydrogen peroxide and air against *Pseudomonas aeruginosa* at room temperature. A 0.81 log reduction was seen after 50 minutes exposure time.

Example 83 shows the activity of the PAN 2 catalyst against *Pseudomonas aeruginosa* in the presence of 0.5% w/v hydrogen peroxide at room temperature. A 4.78 log reduction was seen after 10 minutes exposure time (compared to a 0.58 log reduction after 10 minutes in example 81).

Example 84 shows the activity of the PAN 2 catalyst against *Pseudomonas aeruginosa* in the presence of 0.5% w/v hydrogen peroxide and air at room temperature. A greater than 5.39 log reduction was seen after 10 minutes exposure time (compared to a 0.49 log reduction after 10 minutes in example 82).

Example 85 shows the activity of 0.5% w/v hydrogen peroxide held at neutral pH against *Pseudomonas aeruginosa* at room temperature. A maximum log reduction of 1.92 was seen after 50 minutes exposure time (compared to a 1.02 log reduction after 50 minutes in example 81).

Example 86 shows the activity of 0.5% w/v hydrogen peroxide held at neutral pH against *Pseudomonas aeruginosa* in the presence air at room temperature. A 1.90 log reduction was seen after 60 minutes exposure time (compared to a maximum 0.81 log reduction after 50 minutes in example 82).

Example 87 shows the activity of the PAN 2 catalyst against *Pseudomonas aeruginosa* in the presence of 0.5% w/v hydrogen peroxide held at neutral pH and room temperature. A log reduction of 2.25 was seen after 60 minutes exposure time (compared to a 1.12 log reduction after 60 minutes in example 81; and a maximum 1.92 log reduction in example 85).

Example 88 shows the activity of the PAN 2 catalyst against *Pseudomonas aeruginosa* in the presence of 0.5% w/v hydrogen peroxide and air held at neutral pH and room temperature. A 2.43 log reduction was seen after 60 minutes exposure time (compared to a maximum 0.81 log reduction after 50 minutes in example 82; and a 1.90 log reduction after 60 minutes in example 86).

Examples 89 to 96 show the mean log reduction in *Pseudomonas aeruginosa* numbers after exposure to experimental conditions with and without catalyst and under buffered neutral pH conditions at 35° C. The experimental starting pH ranged from 7.00 to 7.38 and the pH at the end of the experiment ranged from 6.99-7.38. The results are provided in Table 11 below.

Example 93 shows the activity of 0.5% w/v hydrogen peroxide held at neutral pH against *Pseudomonas aeruginosa* at 35° C. A maximum log reduction of 3.90 was seen after 50 minutes exposure time.

Example 94 shows the activity of 0.5% w/v hydrogen peroxide held at neutral pH against *Pseudomonas aeruginosa* in the presence of air at 35° C. A maximum log reduction of 3.41 was seen after 40 minutes exposure time.

Example 95 shows the activity of the PAN 2 catalyst against *Pseudomonas aeruginosa* in the presence of 0.5% w/v hydrogen peroxide held at neutral pH and 35° C. A log reduction of 5.01 was seen after 40 minutes exposure time (compared to a 4.15 log reduction after 40 minutes in example 89 and a maximum log reduction of 3.90 in example 93).

Example 96 shows the activity of the PAN 2 catalyst against *Pseudomonas aeruginosa* in the presence of 0.5% w/v hydrogen peroxide and air held at neutral pH and 35° C. A greater than 5.40 log reduction was seen after 20 minutes exposure time (compared to a 2.42 log reduction after 20 minutes in example 90; a 3.13 log reduction after 20 minutes in example 94; a 4.78 log reduction after 20 minutes in example 95; and a 3.13 log reduction after 20 minutes in example 94).

In conclusion, hydrogen peroxide has no or a lower effect on the survival of bacterial spores than the catalyst compris-

TABLE 11

Mean log reduction in *Pseudomonas aeruginosa* ATCC 15442 numbers after exposure to experimental conditions with and without catalyst and buffered neutral pH conditions at 35° C.

| Catalyst EG and/or PAN No. (1 g +/− 0.1) | Buffered at neutral pH? | $H_2O_2$ (% w/v) | 2.5 L/minute of Air? | Mean $\log_{10}$ reduction in CFU/ml (+/−S.D.) after a specified contact time | | | | | |
|---|---|---|---|---|---|---|---|---|---|
| | | | | 10 min | 20 min | 30 min | 40 min | 50 min | 60 min |
| 89 None | No | 0.5 | No | 2.51 (0.20) | 3.30 (0.17) | 3.94 (0.16) | 4.15 (0.14) | 4.29 (0.20) | 4.45 (0.06) |
| 90 None | No | 0.5 | Yes | 1.80 (0.08) | 2.42 (0.27) | 3.22 (0.61) | 3.13 (0.24) | 3.44 (0.13) | 3.61 (0.35) |
| 91 PAN 2 catalyst | No | 0.5 | No | >5.59 (0.00) | >5.59 (0.00) | >5.59 (0.00) | >5.59 (0.00) | >5.59 (0.00) | >5.59 (0.00) |
| 92 PAN 2 catalyst | No | 0.5 | Yes | >5.59 (0.00) | >5.59 (0.00) | >5.59 (0.00) | >5.59 (0.00) | >5.59 (0.00) | >5.59 (0.00) |
| 93 None | Yes | 0.5 | No | 3.04 (0.07) | 3.57 (0.18) | 3.65 (0.12) | 3.79 (0.42) | 3.90 (0.31) | 3.89 (0.35) |
| 94 None | Yes | 0.5 | Yes | 2.89 (0.06) | 3.13 (0.11) | 3.36 (0.10) | 3.41 (0.07) | 3.39 (0.15) | 3.37 (0.11) |
| 95 PAN 2 catalyst | Yes | 0.5 | No | 4.05 (0.24) | 4.78 (0.71) | 4.89 (0.61) | 5.01 (0.49) | 5.10 (0.45) | 5.24 (0.28) |
| 96 PAN 2 catalyst | Yes | 0.5 | Yes | 3.78 (0.52) | ≧5.40 (0.28) | >5.56 (0.00) | >5.56 (0.00) | >5.56 (0.00) | >5.56 (0.00) |

Example 89 shows the activity of the 0.5% w/v hydrogen peroxide against *Pseudomonas aeruginosa* at 35° C. A 4.45 log reduction was seen after 60 minutes exposure time.

Example 90 shows the activity of the 0.5% w/v hydrogen peroxide and air against *Pseudomonas aeruginosa* at 35° C. A 3.61 log reduction was seen after 60 minutes exposure time.

Example 91 shows the activity of the PAN 2 catalyst against *Pseudomonas aeruginosa* in the presence of 0.5% w/v hydrogen peroxide at 35° C. A greater than 5.59 log reduction was seen after 10 minutes exposure time (compared to a 2.51 log reduction after 10 minutes in example 89).

Example 92 shows the activity of the PAN 2 catalyst against *Pseudomonas aeruginosa* in the presence of 0.5% w/v hydrogen peroxide and air at 35° C. A greater than 5.59 log reduction was seen after 10 minutes exposure time (compared to a 1.80 log reduction after 10 minutes in example 90).

ing PAN fibres (i.e. is less effective at killing the micro-organisms). This is shown by examples 47 to 52.

Hydrogen peroxide has no or a lower effect on the survival of micro-organisms than the catalyst comprising PAN fibres (i.e. is less effective at killing the micro-organisms) at first use and upon reuse with and without air and at room temperature and 35° C. This is shown by examples 53 to 76.

Hydrogen peroxide alone and modified PAN fibre (without metal ion fixed thereto) has no effect or a lower effect on the survival of micro-organisms than the catalyst comprising PAN fibres used with the pre-activation method (i.e. is less effective at killing the micro-organisms). This is shown by examples 77 to 80.

Hydrogen peroxide has no or a lower effect on the survival of micro-organisms than the catalyst comprising PAN fibres (i.e. is less effective at killing the micro-organisms) when held at neutral pH, with and without air and at room temperature and 35° C. This is shown by examples 81 to 96.

Preparation of Catalysts Comprising Wool Fibres

EXAMPLES 101 TO 182

Catalysts were prepared from wool fibres using the steps set out below and according to the parameters shown in Table 12. The catalyst preparation steps include an optional pre-treatment step, in which wool fibres are pre-treated by scouring. Following the optional pre-treatment step, an optional modification step is conducted, followed by an impregnation step, as set out below.

Optional Pre-treatment Step—Scouring

An optional pre-treatment step, in which wool fibres are pre-treated by scouring, may be included in the catalyst preparation. Where pre-treatment by scouring of the wool fibres was conducted (i.e. prior to the modification and/or impregnation steps), it was performed as follows:
  (a) Wool fibres (2 g) were treated with distilled water (200 ml) for 10 minutes at 60° C. Any excess water was rung out (by hand) after treatment.
  (b) The wool fibres from (a) were treated in the presence of non-ionic UPL (United Phosphorous Ltd) surfactant (2 g/l) (supplied by Drummond Parkland) in water for 15 minutes at 60° C. Excess solution was again rung out (by hand) after treatment.
  (c) The wool fibres from (b) were treated in the presence of UPL surfactant (1 g/l) in water for 15 minutes at 60° C. After treatment, excess solution was run off.
  The wool was then washed with distilled water, dried and air-conditioned.

In all stages (a) to (c) above, the liquor to wool ratio (ml:g) was 100:1. All treatments were carried out in a continuous mechanical shaking bath.

Optional Modification Step

A wool sample (3.1 g, in the form of wool fibres) was suspended in a modification solution according to the parameters shown in Table 12 below. The modification solutions used were as follows:
  1. Aqueous hydroxylamine solution: 200 ml containing 42 g/l of hydroxylamine monohydrochloride ($NH_2OH.HCl$);
  2. Aqueous hydrazine and hydroxylamine solution: 100 ml of 30 g/l hydrazine dihydrochloride ($N_2H_4.2HCl$) and 100 ml of 42 g/l hydroxylamine monohydrochloride ($NH_2OH.HCl$).
  3. Aqueous hydrazine solution: 200 ml containing 30 g/l of hydrazine dihydrochloride ($N_2H_4.2HCl$).

Each modification solution was adjusted to pH 7 or 9.5 by addition of sodium hydroxide pellets prior to contacting the modification solution with the wool fibres. The wool samples were then left in the modification solution and heated at a temperature of from 100 to 101° C. for 2 hours. Each sample was then allowed to cool to a temperature at which it could be handled and washed thoroughly with double distilled water (approximately 3 liters). The sample was then left to dry in a dessicator at room temperature for 24 hours.

Wool Impregnation with First Metal Salt

Wool fibres (1 g, optionally pre-treated and/or modified as described above) were placed in a sealed vial containing ferric chloride hexahydrate, $FeCl_3.6H_2O$ (0.1M $Fe^{3+}$ solution, 50 ml at pH=1.72) or salts solution (100 ml) containing $FeCl_3.6H_2O$ and either $Ca(NO_3)_2.4H_2O$ or $Li_2SO_4.H_2O$. The sealed vial was attached to a rotator for continuous shaking at room temperature for 24 hours. Once complete, the wool was removed from the solution and thoroughly washed with double distilled water. The sample was then left to dry in a desiccator at room temperature for 24 hours.

The total amount of first metal cation (i.e. $Fe^{3+}$) adsorbed onto the wool was determined by atomic adsorption spectroscopy, as follows:
  (i) Calibration Method: Standard solutions (1, 2, 3, 4 and 5 ppm) of $Fe^{3+}$ were prepared and analysed using atomic adsorption spectroscopy to produce a calibration graph with respect to concentration. Each solution was analysed in triplicate.
  (ii) Total iron determination for each wool sample: Impregnated wool (0.1 g) containing $Fe^{3+}$ cations was weighed out and then heated in hydrochloric acid (2M, 25 ml) to remove the iron cations from the fibers. The solution was filtered and the fibers washed with double distilled water. The filtrate and washings were collected and placed in a volumetric flask (50 ml). Double distilled water was used to dilute the solution up to 50 ml. The samples were then analysed in triplicate using atomic adsorption spectroscopy. This process was then repeated again for each sample to produce an average.

TABLE 12

Technical Parameters for Preparation of Catalysts

| | | Modification Step | | | | | Impregnation Step | | | |
|---|---|---|---|---|---|---|---|---|---|---|
| | | Hydrazine | Hydroxylamine | | | | | Impregnating Solution | | Iron content |
| Example | Scouring? | Concentration (g/l) | concentration (g/l) | pH | Temp (°C.) | Duration (hours) | Metal Cation(s) | concentration (M) | Duration (hours) | of catalyst (mmol/g wool) |
| 101 | Yes | 30 | 42 | 7.0 | 100 | 2 | $Fe^{3+}$ | 0.1 | 24 | 0.044 |
| 102 | Yes | 30 | 42 | 7.0 | 100 | 2 | $Fe^{3+}$ | 0.1 | 24 | 0.044 |
| 103 | Yes | 30 | 42 | 7.0 | 100 | 2 | $Fe^{3+}$ | 0.1 | 24 | 0.044 |
| 104 | Yes | 0 | 42 | 7.0 | 100 | 2 | $Fe^{3+}$ | 0.1 | 24 | 0.076 |
| 105 | Yes | 0 | 42 | 7.0 | 100 | 2 | $Fe^{3+}$ | 0.1 | 24 | 0.076 |
| 106 | Yes | 0 | 42 | 7.0 | 100 | 2 | $Fe^{3+}$ | 0.1 | 24 | 0.076 |
| 107 | Yes | 0 | 0 | — | — | — | $Fe^{3+}$ | 0.1 | 24 | 0.007 |
| 108 | Yes | 0 | 0 | — | — | — | $Fe^{3+}$ | 0.1 | 24 | 0.007 |
| 109 | No | 0 | 0 | — | — | — | $Fe^{3+}$ | 0.1 | 24 | 0.024 |
| 110 | No | 0 | 0 | — | — | — | $Fe^{3+}$ | 0.1 | 24 | 0.024 |
| 111 | Yes | 0 | 0 | — | — | — | $Fe^{3+}$ | 0.1 | 24 | 0.007 |
| 112 | Yes | 30 | 0 | 9.5 | 100 | 2 | $Fe^{3+}$ | 0.1 | 24 | 0.088 |
| 113 | Yes | 0 | 42 | 9.5 | 100 | 2 | $Fe^{3+}$ | 0.1 | 24 | 0.060 |
| 114 | Yes | 30 | 42 | 9.5 | 100 | 2 | $Fe^{3+}$ | 0.1 | 24 | 0.088 |

TABLE 12-continued

Technical Parameters for Preparation of Catalysts

| | | Modification Step | | | | | Impregnation Step | | | |
|---|---|---|---|---|---|---|---|---|---|---|
| | | Hydrazine | Hydroxylamine | | | | | Impregnating Solution | | Iron content |
| Example | Scouring? | Concentration (g/l) | concentration (g/l) | pH | Temp (° C.) | Duration (hours) | Metal Cation(s) | concentration (M) | Duration (hours) | of catalyst (mmol/g wool) |
| 115 | Yes | 30 | 42 | 7.0 | 100 | 2 | $Fe^{3+}$ | 0.1 | 24 | 0.037 |
| 116 | Yes | 30 | 42 | 7.0 | 100 | 2 | $Fe^{3+}$ | 0.1 | 24 | 0.037 |
| 117 | Yes | 30 | 42 | 7.0 | 100 | 2 | $Fe^{3+}$ | 0.1 | 24 | 0.037 |
| 118 | Yes | 0 | 42 | 7.0 | 100 | 2 | $Fe^{3+}$ | 0.1 | 24 | 0.076 |
| 119 | Yes | 0 | 42 | 7.0 | 100 | 2 | $Fe^{3+}$ | 0.1 | 24 | 0.076 |
| 120 | Yes | 0 | 42 | 7.0 | 100 | 2 | $Fe^{3+}$ | 0.1 | 24 | 0.076 |
| 121 | Yes | 0 | 0 | — | — | — | $Fe^{3+}$ | 0.1 | 24 | 0.007 |
| 122 | Yes | 0 | 0 | — | — | — | $Fe^{3+}$ | 0.1 | 24 | 0.007 |
| 123 | No | 0 | 0 | — | — | — | $Fe^{3+}$ | 0.1 | 24 | 0.009 |
| 124 | No | 0 | 0 | — | — | — | $Fe^{3+}$ | 0.1 | 24 | 0.009 |
| 125 | Yes* | 30 | 42 | 7.0 | 100 | 2 | $Fe^{3+}$ | 0.1 | 24 | 0.040 |
| 126 | Yes* | 30 | 42 | 7.0 | 100 | 2 | $Fe^{3+}$ | 0.1 | 24 | 0.040 |
| 127 | Yes* | 30 | 42 | 7.0 | 100 | 2 | $Fe^{3+}$ | 0.1 | 24 | 0.040 |
| 128 | Yes* | 0 | 42 | 7.0 | 100 | 2 | $Fe^{3+}$ | 0.1 | 24 | 0.055 |
| 129 | Yes* | 0 | 42 | 7.0 | 100 | 2 | $Fe^{3+}$ | 0.1 | 24 | 0.055 |
| 130 | Yes* | 0 | 42 | 7.0 | 100 | 2 | $F^{3+}$ | 0.1 | 24 | 0.055 |
| 131 | Yes* | 0 | 0 | — | — | — | $Fe^{3+}$ | 0.1 | 24 | 0.020 |
| 132 | Yes* | 0 | 0 | — | — | — | $Fe^{3+}$ | 0.1 | 24 | 0.020 |
| 133 | No | 0 | 0 | — | — | — | $Fe^{3+}$ | 0.1 | 24 | 0.036 |
| 134 | No | 0 | 0 | — | — | — | $Fe^{3+}$ | 0.1 | 24 | 0.036 |
| 135 | Yes | 30 | 42 | 7.0 | 100 | 2 | $Fe^{3+}$ | 0.1 | 24 | 0.059 |
| 136 | Yes | 30 | 42 | 7.0 | 100 | 2 | $Fe^{3+}$ | 0.1 | 24 | 0.059 |
| 137 | Yes | 0 | 42 | 7.0 | 100 | 2 | $Fe^{3+}$ | 0.1 | 24 | 0.076 |
| 138 | Yes | 0 | 42 | 7.0 | 100 | 2 | $Fe^{3+}$ | 0.1 | 24 | 0.076 |
| 139 | Yes | 0 | 0 | — | — | — | $Fe^{3+}$ | 0.1 | 24 | 0.047 |
| 140 | Yes | 0 | 0 | — | — | — | $Fe^{3+}$ | 0.1 | 24 | 0.047 |
| 141 | Yes* | 30 | 42 | 7.0 | 100 | 2 | $Fe^{3+}$ | 0.1 | 24 | 0.055 |
| 142 | Yes* | 30 | 42 | 7.0 | 100 | 2 | $Fe^{3+}$ | 0.1 | 24 | 0.055 |
| 142 | Yes* | 0 | 42 | 7.0 | 100 | 2 | $Fe^{3+}$ | 0.1 | 24 | 0.107 |
| 144 | Yes* | 0 | 42 | 7.0 | 100 | 2 | $Fe^{3+}$ | 0.1 | 24 | 0.107 |
| 145 | Yes* | 0 | 0 | — | — | — | $Fe^{3+}$ | 0.1 | 24 | 0.024 |
| 146 | Yes* | 0 | 0 | — | — | — | $Fe^{3+}$ | 0.1 | 24 | 0.024 |
| 147 | No | 0 | 0 | — | — | — | $Fe^{3+}$ | 0.1 | 24 | 0.030 |
| 148 | No | 0 | 0 | — | — | — | $Fe^{3+}$ | 0.1 | 24 | 0.030 |
| 149 | Yes | 30 | 42 | 7.0 | 100 | 2 | $Fe^{3+}$ | 0.1 | 24 | 0.098 |
| 150 | Yes | 30 | 42 | 7.0 | 100 | 2 | $Fe^{3+}$ | 0.1 | 24 | 0.098 |
| 151 | Yes | 0 | 42 | 7.0 | 100 | 2 | $Fe^{3+}$ | 0.1 | 24 | 0.074 |
| 152 | Yes | 0 | 42 | 7.0 | 100 | 2 | $Fe^{3+}$ | 0.1 | 24 | 0.074 |
| 153 | Yes | 0 | 0 | — | — | — | $Fe^{3+}$ | 0.1 | 24 | 0.016 |
| 154 | Yes | 0 | 0 | — | — | — | $Fe^{3+}$ | 0.1 | 24 | 0.016 |
| 155 | Yes | 0 | 42 | 7.0 | 100 | 2 | $Fe^{3+}$ | 0.1 | 24 | 0.077 |
| 156 | Yes | 0 | 42 | 7.0 | 100 | 2 | $Fe^{3+}$ | 0.1 | 24 | 0.077 |
| 157 | Yes | 0 | 42 | 7.0 | 100 | 2 | $Fe^{3+}$ | 0.1 | 24 | 0.074 |
| 158 | Yes | 0 | 42 | 7.0 | 100 | 2 | $Fe^{3+}$ | 0.1 | 24 | 0.074 |
| 159 | Yes | 0 | 42 | 7.0 | 100 | 2 | $Fe^{3+}$ | 0.1 | 24 | 0.060 |
| 160 | Yes | 0 | 42 | 7.0 | 100 | 2 | $Fe^{3+}$ | 0.1 | 24 | 0.060 |
| 161 | Yes | 0 | 42 | 7.0 | 100 | 2 | $Fe^{3+}$ | 0.1 | 24 | 0.101 |
| 162 | Yes | 0 | 42 | 7.0 | 100 | 2 | $Fe^{3+}$ | 0.1 | 24 | 0.101 |
| 163 (control) | N/A | N/A | N/A | N/A | N/A | N/A | N/A | N/A | N/A | N/A |
| 164 (control) | Yes | 30 | 42 | 7.0 | 100 | 2 | N/A | N/A | N/A | 0.000 |
| 165 (control) | Yes | 0 | 42 | 7.0 | 100 | 2 | N/A | N/A | N/A | 0.000 |
| 166 (control) | Yes | 0 | 0 | N/A | N/A | N/A | N/A | N/A | N/A | 0.000 |
| 167 (control) | Yes | 30 | 42 | 7.0 | 100 | 2 | N/A | N/A | N/A | 0.000 |
| 168 (control) | Yes | 0 | 42 | 7.0 | 100 | 2 | N/A | N/A | N/A | 0.000 |
| 169 (control) | Yes | 0 | 0 | N/A | N/A | N/A | N/A | N/A | N/A | 0.000 |
| 170 (control) | Yes* | 30 | 42 | 7.0 | 100 | 2 | N/A | N/A | N/A | 0.000 |
| 171 (control) | Yes* | 0 | 42 | 7.0 | 100 | 2 | N/A | N/A | N/A | 0.000 |
| 172 (control) | Yes* | 0 | 0 | N/A | N/A | N/A | N/A | N/A | N/A | 0.000 |
| 173 (control) | Yes* | 30 | 42 | 7.0 | 100 | 2 | N/A | N/A | N/A | 0.000 |
| 174 (control) | Yes* | 0 | 42 | 7.0 | 100 | 2 | N/A | N/A | N/A | 0.000 |
| 175 (control) | Yes* | 30 | 42 | 7.0 | 100 | 2 | N/A | N/A | N/A | 0.000 |
| 176 (control) | Yes* | 0 | 42 | 7.0 | 100 | 2 | N/A | N/A | N/A | 0.000 |
| 177 | Yes | 0 | 42 | 7.0 | 100 | 2 | $Fe^{3+}$ | 0.1 | 24 | 0.088 |
| 178 | Yes* | 0 | 42 | 7.0 | 100 | 2 | $Fe^{3+}$ | 0.1 | 24 | 0.074 |
| 179 | Yes* | 0 | 42 | 7.0 | 100 | 2 | $Fe^{3+}$ | 0.1 | 24 | 0.081 |
| 180 | Yes* | 0 | 42 | 7.0 | 100 | 2 | $Fe^{3+}/Ca^{2+}$ | 0.039/0.095 | 24 | 0.080 |
| 181 | Yes* | 0 | 42 | 7.0 | 100 | 2 | $Fe^{3+}/Li^{+}$ | 0.064/0.116 | 24 | 0.079 |
| 182 | Yes* | 0 | 42 | 7.0 | 100 | 2 | $Fe^{3+}/Li^{+}$ | 0.064/0.116 | 24 | 0.079 |
| 183 | Yes* | 0 | 42 | 7.0 | 100 | 2 | $Fe^{3+}/Ca^{2+}$ | 0.028/0.095 | 24 | 0.080 |

Column 2 in Table 12 indicates whether or not the catalyst preparation included a pre-treatment scouring step. Where "Yes" is indicated, the pre-treatment scouring step was conducted as described above (referred to herein as "laboratory scoured" wool). Where "Yes*" is indicated, the pre-treatment scouring step was conducted by the wool manufacturer prior to purchase of the wool, by the mill scouring method known in the art.

Examples 101 to 110 and Control Examples 164 to 166 use WOOLMARK top wool. Examples 111 to 124 and Control Examples 167 to 169 use DEFRA top wool. The term "top wool" is a recognised term within the art and as the skilled person would appreciate refers to main wool fleece, not including fleece from underneath the sheep (for example from the stomach/belly area). All other wools were provided by Thomas Chadwick and Sons, being Dark Grey Herdwick (Examples 125 to 140 and Control Examples 170 to 172), Swaledale (Examples 141 to 154 and Control Examples 173 to 176), Crosses (Examples 155 to 158 and Examples 177 to 183), Halfbreds (Examples 159 and 160) and Blackface (Examples 161 and 162). No wool was used in Control Example 163.

Test for Iron Removal Degree

For each catalyst prepared, a test was conducted to determine how strongly the iron was fixed on the wool (prior to catalysis). Iron fixing strength is evaluated using a strong complexing agent, such as disodium-ethylenediamine tetraacetic acid (disodium-EDTA). The disodium-EDTA complexes with $Fe^{3+}$ ions at pH 5 and results in the removal of the $Fe^{3+}$ ions from the wool into solution if they are not strongly fixed. Wool fibers (0.1 g) containing the metal cation were thoroughly ground and left in contact with aqueous disodium-EDTA solution (0.5M, 5 ml) for 24 hours. An aliquot of the wool-EDTA solution (1 ml) was diluted with distilled water and made up to the mark in a volumetric flask (50 ml). The total iron content of the solution was determined in triplicate directly using atomic adsorption spectroscopy.

EXAMPLES 101 TO 162 AND 183 AND CONTROL EXAMPLES 163 TO 176

Determination of Activity of the Catalyst

In Examples 101 to 110 and 115 to 162 and Control Examples 163 to 176, the activity of the catalyst was determined in relation to the decomposition (by oxidation) of phenol. In Examples 111 to 114, the activity of the catalyst was determined in relation to the decomposition (by oxidation) of the dye, Acid Blue 45. In Example 183, the activity of the catalyst was determined in relation to the decomposition (by oxidation) of Estrone (E1) in a static reactor. In Examples 101 to 162 and 183 and Control Examples 163 to 176, the catalysts were evaluated in a static reactor.

Phenol Decomposition

Examples 101 to 110 and 115 to 162 and Control Examples 163 to 176 were conducted as follows:

As the feed solution for the determination of catalyst activity by phenol decomposition, an aqueous solution of phenol (50 ml, 24 ppm) was provided and adjusted to pH 3 by adding dilute (0.01M) hydrochloric acid. 5 ml of an aqueous stock solution of $H_2O_2$ (500 ppm) was added to give a resultant $H_2O_2$ concentration of about 45 ppm and a resultant phenol concentration of about 22 ppm.

Various concentrations of aqueous phenol solutions were prepared (5, 10, 15, 20, 25 and 30 ppm) and analysed by HPLC to prepare a calibration graph. A standard C-18 (250× 4.6 mm) packed column was used as the stationary phase. The mobile phase was a mixture of water (10% v/v) and acetonitrile (90% v/v) at a flow rate of 1 ml/min. The column elute was passed through a UV detector (Helios Gamma UV/VIS spectrophotometer supplied by Thermo Scientific) set at 254 nm. Sample volumes of 20 µl were injected onto the column. Samples were analysed in triplicate.

For the catalysis, feed solution (50 ml) was placed in a Dreschel bottle and a zero reading taken for analysis, this became the t=0 minutes reading (i.e. before exposure to the catalyst). The catalyst (0.6 g) was then added to the feed solution and the vessel stoppered allowing air to flow through. Samples of the treated feed solution were collected at ten minute intervals for a total of 2 hours. Once complete, the catalyst was removed and rinsed with double distilled water to remove any traces of hydrogen peroxide.

Each sample collected was analysed by HPLC for residual phenol content, using the same column as for the calibration step discussed above. The mobile phase was a mixture of water (40% v/v) and methanol (60% v/v) at a flow rate of 1 ml/min. UV detection and volume of sample injection were as for the calibration step discussed above.

A control solution (feed (phenol) solution+$H_2O_2$+bubbled air, but no catalyst) was used to evaluate the hydrogen peroxide contribution to catalysis using the same setup (Example 163). Wool samples with no $Fe^{3+}$ impregnation were evaluated in the same manner (Examples 164 to 176).

Acid Blue 45 Decomposition

Examples 111 to 114 were conducted as follows

The catalysis was conducted as described above for Examples 101 to 110 and 115 to 162 and Control Examples 163 to 176, except that the samples were analysed by UV/VIS spectrophotometry. The UV/VIS Spectrophotometer used was the Helios Gamma supplied by Thermo Scientific at $\lambda_{max}$=594 nm. The feed solution comprised the dye Acid Blue 45 (50 ml, 10 ppm) was adjusted to pH 3 with dilute hydrochloric acid (2M). $H_2O_2$ (5 ml) was added from a stock solution (500 ppm), to provide a resultant concentration of $H_2O_2$ was about 45 ppm. The resultant initial acid blue 45 concentration was about 9.1 ppm.

Estrone (E1) Decomposition

Example 183 was conducted as follows:

The catalysis was conducted as described above for Examples 101 to 110 and 115 to 162 and Control Examples 163 to 176, except that each sample collected at the end of experiment was analysed for residual estrone (E1) content using an ELISA kit in accordance with the standard technique for E1 analysis (Method A) described in the Users Guide (Estrone (E1) ELISA KIT (Microplate). User's Guide, Japan EnviroChemicals, Ltd) and based on measuring the absorbance of the samples at 450 nm at ambient temperature using MULTISKAN EX (Thermo, Electron Corporation) equipment. The feed solution had a volume of 100 ml and comprised an aqueous estrone (E1) solution (100 ml, 1 µg/l) and $H_2O_2$ (57 ppm). 0.2 g of catalyst was used and air was passed through the solution at a rate of 1 l/minute; duration of treatment was 2 hours at room temperature.

COMMENTS ON EXAMPLES 101 TO 162 AND 183 AND CONTROL EXAMPLES 163 TO 176

Example 101 below relates to the catalytic process (i.e. phenol decomposition) conducted as described above using the catalyst as prepared in Example 101, as shown in Table 12. The same numbering applies to all other Examples and Control Examples.

References to three cycles of catalysis mean that a catalyst is contacted with a first feed solution for the specified time of oxidation, removed from the first feed solution, contacted with a second fresh feed solution for the specified time of oxidation, removed from the second feed solution and contacted with a third fresh feed solution for the specified time of oxidation. In other words, the catalyst undergoes three cycles of catalysis by contacting with three fresh feed solutions. References herein to Examples 101a-101c relate to the three cycles of catalysis that is conducted with the catalyst of Example 101 (as shown in Table 12) and similarly with the other Examples and Control Examples where reference is made to examples a-c.

EXAMPLES 101 TO 103

Examples 101a-101c illustrate the catalytic activity over three cycles for laboratory scoured WOOLMARK wool modified with a mixture of hydrazine and hydroxylamine followed by impregnation with $Fe^{3+}$ cations as described in Table 12 above. Examples 102a-103c illustrate the outcome of batch-to-batch reproducibility studies over three cycles (each using a fresh feed solution) used in Examples 101a-101c using the catalysts as prepared in Examples 102 and 103 described as prepared in Table 12 above.

All catalytic activity evaluations contained hydrogen peroxide (50 ppm) in the feed.

EXAMPLES 104 TO 106

Examples 104a-104c illustrate the catalytic activity over three cycles for laboratory scoured WOOLMARK wool modified with hydroxylamine followed by impregnation with $Fe^{3+}$ cations. Examples 105a-106c illustrate the outcome of batch-to-batch reproducibility studies over three cycles for the same sample used in Examples 104a-104c.

EXAMPLES 107 AND 108

Examples 107a-107c illustrate the catalytic activity over three cycles for laboratory scoured WOOLMARK wool impregnated with $Fe^{3+}$ cations. Examples 108a-108c illustrate the outcome of batch-to-batch reproducibility studies over three cycles for the same sample used in Examples 107a-107c.

EXAMPLES 109 AND 110

Examples 109a-109c illustrate the catalytic activity over three cycles for non-scoured WOOLMARK wool impregnated with $Fe^{3+}$ cations. Examples 110a-110c illustrate the outcome of batch-to-batch reproducibility studies over three cycles for the same sample used in Examples 109a-109c.

EXAMPLE 111

Examples 111a-111c illustrate the catalytic activity of laboratory scoured and $Fe^{3+}$ cation impregnated DEFRA wool modified against Acid Blue 45 over three cycles.

EXAMPLE 112

Examples 112a-112c demonstrate the catalytic activity of laboratory scoured DEFRA wool modified at pH 9.5 with hydrazine followed by impregnation with $Fe^{3+}$ cations against Acid Blue 45 over three cycles.

EXAMPLE 113

Examples 113a-113c demonstrate the catalytic activity of laboratory scoured DEFRA wool modified at pH 9.5 with hydroxylamine followed by impregnation with $Fe^{3+}$ cations against Acid Blue 45 over three cycles.

EXAMPLE 114

Examples 114a-114c demonstrate the catalytic activity of laboratory scoured DEFRA wool modified at pH 9.5.

EXAMPLES 115 TO 117

Examples 115a-115c illustrate the catalytic activity over three cycles for laboratory scoured DEFRA wool modified with a mixture of hydrazine and hydroxylamine followed by impregnation with $Fe^{3+}$ cations as described in Table 12 above. Examples 116a-117c illustrate the outcome of batch-to-batch reproducibility studies over three cycles for the same sample used in Examples 115a-115c.

EXAMPLES 118 TO 120

Examples 118a-118c illustrate the catalytic activity over three cycles for laboratory scoured DEFRA wool modified with hydroxylamine followed by impregnation with $Fe^{3+}$ cations. Examples 119c-120c illustrate the outcome of batch-to-batch reproducibility studies over three cycles for the same sample used in Examples 118a-118c.

EXAMPLES 121 AND 122

Examples 121a-121c illustrate the catalytic activity over three cycles for laboratory scoured DEFRA wool impregnated with $Fe^{3+}$ cations. Examples 122a-122c illustrate the outcome of batch-to-batch reproducibility studies over three cycles for the same sample used in Examples 121a-121c.

EXAMPLES 123 AND 124

Examples 123a-123c illustrate the catalytic activity over three cycles for non-scoured DEFRA wool impregnated with $Fe^{3+}$ cations. Examples 124a-124c illustrate the outcome of batch-to-batch reproducibility studies over three cycles for the same sample used in Examples 123a-123c.

EXAMPLES 125 TO 127

Examples 125a-125c illustrate the catalytic activity over three cycles for mill scoured Dark Grey Herdwick wool modified with a mixture of hydrazine and hydroxylamine followed by impregnation with $Fe^{3+}$ cations as described in Table 12 above. Examples 126a-127c illustrate the outcome of batch-to-batch reproducibility studies over three cycles for the same sample used in Examples 125a-125c.

EXAMPLES 128 TO 130

Examples 128a-128c illustrate the catalytic activity over three cycles for mill scoured Dark Grey Herdwick wool modified with hydroxylamine followed by impregnation with $Fe^{3+}$ cations. Examples 129a-130c illustrate the outcome of batch-to-batch reproducibility studies over three cycles for the same sample used in Examples 129a-129c.

EXAMPLES 131 AND 132

Examples 131 and 132 illustrate the catalytic activity over one cycle for two batches of mill scoured Dark Grey Herdwick wool impregnated with $Fe^{3+}$ cations.

EXAMPLES 133 AND 134

Examples 133 and 134 illustrate the catalytic activity over one cycle for two batches of non-scoured Dark Grey Herdwick wool impregnated with $Fe^{3+}$ cations.

EXAMPLES 135 AND 136

Examples 135a-135c illustrate the catalytic activity over three cycles for laboratory scoured Dark Grey Herdwick wool modified with a mixture of hydrazine and hydroxylamine followed by impregnation with $Fe^{3+}$ cations as described in Table 12 above. Examples 136a-136c illustrate the outcome of batch-to-batch reproducibility studies over three cycles for the same sample used in Examples 135a-135c.

EXAMPLES 137 AND 138

Examples 137a-137c illustrate the catalytic activity over three cycles for laboratory scoured Dark Grey Herdwick wool modified with hydroxylamine followed by impregnation with $Fe^{3+}$ cations. Examples 138a-138c illustrate the outcome of batch-to-batch reproducibility studies over three cycles for the same sample used in Examples 137a-137c.

EXAMPLES 139 AND 140

Examples 139 and 140 illustrate the catalytic activity over one cycle for two batches of laboratory scoured Dark Grey Herdwick wool impregnated with $Fe^{3+}$ cations.

EXAMPLES 141 AND 142

Examples 141a-141c illustrate the catalytic activity over three cycles for mill scoured Swaledale wool modified with a mixture of hydrazine and hydroxylamine followed by impregnation with $Fe^{3+}$ cations as described in Table 12 above. Examples 142a-142c illustrate the outcome of batch-to-batch reproducibility studies over three cycles for the same sample used in Examples 141a-141c.

EXAMPLES 143 AND 144

Examples 143a-143c illustrate the catalytic activity over three cycles for mill scoured Swaledale wool modified with hydroxylamine followed by impregnation with $Fe^{3+}$ cations. Examples 144a-144c illustrate the outcome of batch-to-batch reproducibility studies over three cycles for the same sample used in Examples 143a-143c.

EXAMPLES 145 AND 146

Examples 145 and 146 illustrate the catalytic activity over one cycle for two batches of mill scoured Swaledale wool impregnated with $Fe^{3+}$ cations.

EXAMPLES 147 AND 148

Examples 147 and 148 illustrate the catalytic activity over one cycle for two batches of non-scoured Swaledale wool impregnated with $Fe^{3+}$ cations.

EXAMPLES 149 AND 150

Examples 149a-149c illustrate the catalytic activity over three cycles for laboratory scoured Swaledale wool modified with a mixture of hydrazine and hydroxylamine followed by impregnation with $Fe^{3+}$ cations as described in Table 12 above. Examples 150a-150c illustrate the outcome of batch-to-batch reproducibility studies over three cycles for the same sample used in Examples 149a-149c.

EXAMPLES 151 AND 152

Examples 151a-151c illustrate the catalytic activity over three cycles for laboratory scoured Swaledale wool modified with hydroxylamine followed by impregnation with $Fe^{3+}$ cations. Examples 152a-152c illustrate the outcome of batch-to-batch reproducibility studies over three cycles for the same sample used in Examples 151a-151c.

EXAMPLES 153 AND 154

Examples 153 and 154 illustrate the catalytic activity over one cycle for two batches of laboratory scoured Swaledale wool impregnated with $Fe^{3+}$ cations.

EXAMPLES 155 AND 156

Examples 155a-155c illustrate the catalytic activity over three cycles for mill scoured Crosses wool modified with hydroxylamine followed by impregnation with $Fe^{3+}$ cations. Examples 156a-156c illustrate the outcome of batch-to-batch reproducibility studies over three cycles for the same sample used in Examples 155a-155c.

EXAMPLES 157 AND 158

Examples 157a-157c illustrate the catalytic activity over three cycles for laboratory scoured Crosses wool modified with hydroxylamine followed by impregnation with $Fe^{3+}$ cations. Examples 158a-158c illustrate the outcome of batch-to-batch reproducibility studies over three cycles for the same sample used in Examples 157a-157c.

EXAMPLES 159 AND 160

Examples 159a-159c illustrate the catalytic activity over three cycles for laboratory scoured Halfbreds wool modified with hydroxylamine followed by impregnation with $Fe^{3+}$ cations. Examples 160a-160c illustrate the outcome of batch-to-batch reproducibility studies over three cycles for the same sample used in Examples 159a-159c.

EXAMPLES 161 AND 162

Examples 161a-161c illustrate the catalytic activity over three cycles for laboratory scoured Blackface wool modified with hydroxylamine followed by impregnation with $Fe^{3+}$ cations. Examples 162a-162c illustrate the outcome of batch-to-batch reproducibility studies over three cycles for the same sample used in Examples 161a-161c.

CONTROL EXAMPLE 163

This is a control experiment where no wool catalyst is present. It is to assess the amount of phenol decomposition achieved using hydrogen peroxide only.

CONTROL EXAMPLE 164

This is a WOOLMARK control sample. The wool underwent modification with a mixture of hydrazine and hydroxylamine as described in Table 12 above but was not subjected to impregnation with $Fe^{3+}$ cations. Phenol catalysis was performed using the control in order to evaluate what contribution modified wool had on catalysis prior to iron loading.

CONTROL EXAMPLE 165

This is a WOOLMARK control sample. The wool was modified with hydroxylamine only and was not impregnated with $Fe^{3+}$ cations. Phenol catalysis was performed using the control in order to evaluate what contribution modified wool had on catalysis prior to iron loading.

CONTROL EXAMPLE 166

This is a WOOLMARK control sample. The wool was subjected to laboratory scouring. No modification or impregnation with $Fe^{3+}$ cations was performed. Phenol catalysis was performed using the control in order to evaluate what contribution modified wool had on catalysis prior to iron loading.

CONTROL EXAMPLE 167

This is a DEFRA control sample. The wool was modified with 50% hydrazine and 50% hydroxylamine. No impregnation with $Fe^{3+}$ cations was performed. Phenol catalysis was performed using the control in order to evaluate what contribution modified wool had on catalysis prior to iron loading.

CONTROL EXAMPLE 168

This is a DEFRA control sample. The wool was modified with hydroxylamine only and was not impregnated with $Fe^{3+}$ cations. Phenol catalysis was performed using the control in order to evaluate what contribution modified wool had on catalysis prior to iron loading.

CONTROL EXAMPLE 169

This is a DEFRA control sample. The wool was subjected to laboratory scouring only. No modification or impregnation with $Fe^{3+}$ cations was performed. Phenol catalysis was performed using the control in order to evaluate what contribution modified wool had on catalysis prior to iron loading.

CONTROL EXAMPLE 170

This is a Dark Grey Herdwick control sample. The wool was modified with a mixture of hydrazine and hydroxylamine as described in Table 12 above. The wool was not impregnated with $Fe^{3+}$ cations. Phenol catalysis was performed using the control in order to evaluate what contribution modified wool had on catalysis prior to iron loading.

CONTROL EXAMPLE 171

This is a Dark Grey Herdwick control sample. The wool was modified with hydroxylamine only and was not impregnated with $Fe^{3+}$ cations. Phenol catalysis was performed using the control in order to evaluate what contribution modified wool had on catalysis prior to iron loading.

CONTROL EXAMPLE 172

This is a Dark Grey Herdwick control sample. The wool was supplied pre-scoured by Thomas Chadwick & Sons. No other treatment was performed. Phenol catalysis was performed using the control in order to evaluate what contribution modified wool had on catalysis prior to iron loading.

CONTROL EXAMPLE 173

This is a Swaledale control sample. The wool was modified with a mixture of hydrazine and hydroxylamine as described in Table 12 above. There was no impregnation with $Fe^{3+}$ cations. Phenol catalysis was performed using the control in order to evaluate what contribution modified wool had on catalysis prior to iron loading.

CONTROL EXAMPLE 174

This is a Swaledale control sample. The wool was modified with hydroxylamine only. There was no impregnation with $Fe^{3+}$ cations. Phenol catalysis was performed using the control in order to evaluate what contribution modified wool had on catalysis prior to iron loading.

CONTROL EXAMPLE 175

This is a Swaledale control sample. The wool was supplied as scoured by Thomas Chadwick & Sons. The scoured wool was modified with a mixture of hydrazine and hydroxylamine as described in Table 12 above. There was no impregnation with $Fe^{3+}$ cations. Phenol catalysis was performed using the control in order to evaluate what contribution modified wool had on catalysis prior to iron loading.

CONTROL EXAMPLE 176

This is a Swaledale control sample. The wool was supplied as scoured from Thomas Chadwick & Sons. The wool was modified with hydroxylamine only and there was no impregnation with $Fe^{3+}$ cations. Phenol catalysis was performed using the control in order to evaluate what contribution modified wool had on catalysis prior to iron loading.

EXAMPLE 183

Example 183 demonstrates the catalytic activity of mill scoured CROSSES wool modified at pH 7 with hydroxylamine only followed by impregnation with $Fe^{3+}$ and $Ca^{2+}$ cations against Estrone (E1). This example was conducted over a single cycle only.

Table 13 contains the results for the catalysts of Examples 101 to 162 and 183 and Control Examples 163 to 176 evaluated in a static reactor.

TABLE 13

Catalytic Activity Results obtained by Static Reactor

| Example | Iron Removal degree after EDTA solution treatment (%) | Catalytic process | Catalysis mass/solution volume ratio (modulus) (kg/m³) | Time of oxidation (min) | Initial concentration of substrate (mg/l) | Conversion degree (%) |
|---|---|---|---|---|---|---|
| Example 101a | 0.002 | Phenol Oxidation | 0.012 | 60 | 22 | 99 |
| Example 101b | N/A | Phenol Oxidation | 0.012 | 60 | 22 | 98 |
| Example 101c | N/A | Phenol Oxidation | 0.012 | 60 | 22 | 98 |
| Example 102a | 0.002 | Phenol Oxidation | 0.012 | 60 | 22 | 99 |
| Example 102b | N/A | Phenol Oxidation | 0.012 | 60 | 22 | 98 |
| Example 102c | N/A | Phenol Oxidation | 0.012 | 60 | 22 | 98 |
| Example 103a | 0.002 | Phenol Oxidation | 0.012 | 60 | 22 | 99 |
| Example 103b | N/A | Phenol Oxidation | 0.012 | 60 | 22 | 81 |
| Example 103c | N/A | Phenol Oxidation | 0.012 | 60 | 22 | 98 |
| Example 104a | N.D. | Phenol Oxidation | 0.012 | 60 | 22 | 99 |
| Example 104b | N/A | Phenol Oxidation | 0.012 | 60 | 22 | 100 |
| Example 104c | N/A | Phenol Oxidation | 0.012 | 60 | 22 | 100 |
| Example 105a | N.D. | Phenol Oxidation | 0.012 | 60 | 22 | 100 |
| Example 105b | N/A | Phenol Oxidation | 0.012 | 60 | 22 | 100 |
| Example 105c | N/A | Phenol Oxidation | 0.012 | 60 | 22 | 100 |
| Example 106a | N.D. | Phenol Oxidation | 0.012 | 60 | 22 | 99 |
| Example 106b | N/A | Phenol Oxidation | 0.012 | 60 | 22 | 100 |
| Example 106c | N/A | Phenol Oxidation | 0.012 | 60 | 22 | 100 |
| Example 107a | 0.010 | Phenol Oxidation | 0.012 | 60 | 22 | 99 |
| Example 107b | N/A | Phenol Oxidation | 0.012 | 60 | 22 | 100 |
| Example 107c | N/A | Phenol Oxidation | 0.012 | 60 | 22 | 100 |
| Example 108a | 0.010 | Phenol Oxidation | 0.012 | 60 | 22 | 56 |
| Example 108b | N/A | Phenol Oxidation | 0.012 | 60 | 22 | 52 |
| Example 108c | N/A | Phenol Oxidation | 0.012 | 60 | 22 | 60 |
| Example 109a | 0.008 | Phenol Oxidation | 0.012 | 60 | 22 | 36 |
| Example 109b | N/A | Phenol Oxidation | 0.012 | 60 | 22 | 49 |
| Example 109c | N/A | Phenol Oxidation | 0.012 | 60 | 22 | 48 |
| Example 110a | 0.008 | Phenol Oxidation | 0.012 | 60 | 22 | 31 |
| Example 110b | N/A | Phenol Oxidation | 0.012 | 60 | 22 | 49 |
| Example 110c | N/A | Phenol Oxidation | 0.012 | 60 | 22 | 49 |
| Example 111a | 0.011 | Acid Blue 45 Oxidation | 0.012 | 30 | 9.1 | 86 |
| Example 111b | N/A | Acid Blue 45 Oxidation | 0.012 | 30 | 9.1 | 53 |
| Example 111c | N/A | Acid Blue 45 Oxidation | 0.012 | 30 | 9.1 | 2 |
| Example 112a | 0.002 | Acid Blue 45 Oxidation | 0.012 | 30 | 9.1 | 100 |
| Example 112b | N/A | Acid Blue 45 Oxidation | 0.012 | 30 | 9.1 | 100 |
| Example 112c | N/A | Acid Blue 45 Oxidation | 0.012 | 30 | 9.1 | 100 |

TABLE 13-continued

Catalytic Activity Results obtained by Static Reactor

| Example | Iron Removal degree after EDTA solution treatment (%) | Catalytic process | Catalysis mass/solution volume ratio (modulus) (kg/m³) | Time of oxidation (min) | Initial concentration of substrate (mg/l) | Conversion degree (%) |
|---|---|---|---|---|---|---|
| Example 113a | N.D. | Acid Blue 45 Oxidation | 0.012 | 30 | 9.1 | 85 |
| Example 113b | N/A | Acid Blue 45 Oxidation | 0.012 | 30 | 9.1 | 81 |
| Example 113c | N/A | Acid Blue 45 Oxidation | 0.012 | 30 | 9.1 | 95 |
| Example 114a | 0.001 | Acid Blue 45 Oxidation | 0.012 | 30 | 9.1 | 100 |
| Example 114b | N/A | Acid Blue 45 Oxidation | 0.012 | 30 | 9.1 | 100 |
| Example 114c | N/A | Acid Blue 45 Oxidation | 0.012 | 30 | 9.1 | 100 |
| Example 115a | 0.001 | Phenol Oxidation | 0.012 | 60 | 22 | 93 |
| Example 115b | N/A | Phenol Oxidation | 0.012 | 60 | 22 | 93 |
| Example 115c | N/A | Phenol Oxidation | 0.012 | 60 | 22 | 93 |
| Example 116a | 0.001 | Phenol Oxidation | 0.012 | 60 | 22 | 93 |
| Example 116b | N/A | Phenol Oxidation | 0.012 | 60 | 22 | 93 |
| Example 116c | N/A | Phenol Oxidation | 0.012 | 60 | 22 | 94 |
| Example 117a | 0.001 | Phenol Oxidation | 0.012 | 60 | 22 | 93 |
| Example 117b | N/A | Phenol Oxidation | 0.012 | 60 | 22 | 93 |
| Example 117c | N/A | Phenol Oxidation | 0.012 | 60 | 22 | 94 |
| Example 118a | N.D. | Phenol Oxidation | 0.012 | 60 | 22 | 99 |
| Example 118b | N/A | Phenol Oxidation | 0.012 | 60 | 22 | 99 |
| Example 118c | N/A | Phenol Oxidation | 0.012 | 60 | 22 | 99 |
| Example 119a | N.D. | Phenol Oxidation | 0.012 | 60 | 22 | 99 |
| Example 119b | N/A | Phenol Oxidation | 0.012 | 60 | 22 | 99 |
| Example 119c | N/A | Phenol Oxidation | 0.012 | 60 | 22 | 99 |
| Example 120a | N.D. | Phenol Oxidation | 0.012 | 60 | 22 | 99 |
| Example 120b | N/A | Phenol Oxidation | 0.012 | 60 | 22 | 99 |
| Example 120c | N/A | Phenol Oxidation | 0.012 | 60 | 22 | 99 |
| Example 121a | 0.011 | Phenol Oxidation | 0.012 | 60 | 22 | 54 |
| Example 121b | N/A | Phenol Oxidation | 0.012 | 60 | 22 | 47 |
| Example 121c | N/A | Phenol Oxidation | 0.012 | 60 | 22 | 50 |
| Example 122a | 0.011 | Phenol Oxidation | 0.012 | 60 | 22 | 53 |
| Example 122b | N/A | Phenol Oxidation | 0.012 | 60 | 22 | 56 |
| Example 122c | N/A | Phenol Oxidation | 0.012 | 60 | 22 | 51 |
| Example 123a | 0.102 | Phenol Oxidation | 0.012 | 60 | 22 | 48 |
| Example 123b | N/A | Phenol Oxidation | 0.012 | 60 | 22 | 47 |
| Example 123c | N/A | Phenol Oxidation | 0.012 | 60 | 22 | 45 |
| Example 124a | 0.102 | Phenol Oxidation | 0.012 | 60 | 22 | 50 |
| Example 124b | N/A | Phenol Oxidation | 0.012 | 60 | 22 | 50 |
| Example 124c | N/A | Phenol Oxidation | 0.012 | 60 | 22 | 45 |

TABLE 13-continued

Catalytic Activity Results obtained by Static Reactor

| Example | Iron Removal degree after EDTA solution treatment (%) | Catalytic process | Catalysis mass/solution volume ratio (modulus) (kg/m$^3$) | Time of oxidation (min) | Initial concentration of substrate (mg/l) | Conversion degree (%) |
|---|---|---|---|---|---|---|
| Example 125a | 0.002 | Phenol Oxidation | 0.012 | 60 | 22 | 100 |
| Example 125b | N/A | Phenol Oxidation | 0.012 | 60 | 22 | 100 |
| Example 125c | N/A | Phenol Oxidation | 0.012 | 60 | 22 | 100 |
| Example 126a | 0.002 | Phenol Oxidation | 0.012 | 60 | 22 | 100 |
| Example 126b | N/A | Phenol Oxidation | 0.012 | 60 | 22 | 100 |
| Example 126c | N/A | Phenol Oxidation | 0.012 | 60 | 22 | 100 |
| Example 127a | 0.002 | Phenol Oxidation | 0.012 | 60 | 22 | 100 |
| Example 127b | N/A | Phenol Oxidation | 0.012 | 60 | 22 | 100 |
| Example 127c | N/A | Phenol Oxidation | 0.012 | 60 | 22 | 100 |
| Example 128a | N.D. | Phenol Oxidation | 0.012 | 60 | 22 | 26 |
| Example 128b | N/A | Phenol Oxidation | 0.012 | 60 | 22 | 23 |
| Example 128c | N/A | Phenol Oxidation | 0.012 | 60 | 22 | 24 |
| Example 129a | N.D. | Phenol Oxidation | 0.012 | 60 | 22 | 31 |
| Example 129b | N/A | Phenol Oxidation | 0.012 | 60 | 22 | 33 |
| Example 129c | N/A | Phenol Oxidation | 0.012 | 60 | 22 | 28 |
| Example 130a | N.D. | Phenol Oxidation | 0.012 | 60 | 22 | 26 |
| Example 130b | N/A | Phenol Oxidation | 0.012 | 60 | 22 | 31 |
| Example 130c | N/A | Phenol Oxidation | 0.012 | 60 | 22 | 23 |
| Example 131 | 0.101 | Phenol Oxidation | 0.012 | 60 | 22 | 34 |
| Example 132 | 0.101 | Phenol Oxidation | 0.012 | 60 | 22 | 30 |
| Example 133 | 0.110 | Phenol Oxidation | 0.012 | 60 | 22 | 33 |
| Example 134 | 0.110 | Phenol Oxidation | 0.012 | 60 | 22 | 38 |
| Example 135a | 0.001 | Phenol Oxidation | 0.012 | 60 | 22 | 26 |
| Example 135b | N/A | Phenol Oxidation | 0.012 | 60 | 22 | 29 |
| Example 135c | N/A | Phenol Oxidation | 0.012 | 60 | 22 | 85 |
| Example 136a | 0.001 | Phenol Oxidation | 0.012 | 60 | 22 | 100 |
| Example 136b | N/A | Phenol Oxidation | 0.012 | 60 | 22 | 100 |
| Example 136c | N/A | Phenol Oxidation | 0.012 | 60 | 22 | 100 |
| Example 137a | N.D. | Phenol Oxidation | 0.012 | 60 | 22 | 100 |
| Example 137b | N/A | Phenol Oxidation | 0.012 | 60 | 22 | 100 |
| Example 137c | N/A | Phenol Oxidation | 0.012 | 60 | 22 | 85 |
| Example 138a | N.D. | Phenol Oxidation | 0.012 | 60 | 22 | 100 |
| Example 138b | N/A | Phenol Oxidation | 0.012 | 60 | 22 | 100 |
| Example 138c | N/A | Phenol Oxidation | 0.012 | 60 | 22 | 100 |
| Example 139 | 0.102 | Phenol Oxidation | 0.012 | 60 | 22 | 69 |
| Example 140 | 0.102 | Phenol Oxidation | 0.012 | 60 | 22 | 100 |

TABLE 13-continued

Catalytic Activity Results obtained by Static Reactor

| Example | Iron Removal degree after EDTA solution treatment (%) | Catalytic process | Catalysis mass/solution volume ratio (modulus) (kg/m³) | Time of oxidation (min) | Initial concentration of substrate (mg/l) | Conversion degree (%) |
|---|---|---|---|---|---|---|
| Example 141a | 0.001 | Phenol Oxidation | 0.012 | 60 | 22 | 40 |
| Example 141b | N/A | Phenol Oxidation | 0.012 | 60 | 22 | 76 |
| Example 141c | N/A | Phenol Oxidation | 0.012 | 60 | 22 | 90 |
| Example 142a | 0.001 | Phenol Oxidation | 0.012 | 60 | 22 | 45 |
| Example 142b | N/A | Phenol Oxidation | 0.012 | 60 | 22 | 73 |
| Example 142c | N/A | Phenol Oxidation | 0.012 | 60 | 22 | 85 |
| Example 143a | N.D. | Phenol Oxidation | 0.012 | 60 | 22 | 21 |
| Example 143b | N/A | Phenol Oxidation | 0.012 | 60 | 22 | 96 |
| Example 143c | N/A | Phenol Oxidation | 0.012 | 60 | 22 | 100 |
| Example 144a | N.D. | Phenol Oxidation | 0.012 | 60 | 22 | 29 |
| Example 144b | N/A | Phenol Oxidation | 0.012 | 60 | 22 | 89 |
| Example 144c | N/A | Phenol Oxidation | 0.012 | 60 | 22 | 100 |
| Example 145 | 0.101 | Phenol Oxidation | 0.012 | 60 | 22 | 63 |
| Example 146 | 0.101 | Phenol Oxidation | 0.012 | 60 | 22 | 45 |
| Example 147 | 0.100 | Phenol Oxidation | 0.012 | 60 | 22 | 24 |
| Example 148 | 0.100 | Phenol Oxidation | 0.012 | 60 | 22 | 46 |
| Example 149a | 0.002 | Phenol Oxidation | 0.012 | 60 | 22 | 27 |
| Example 149b | N/A | Phenol Oxidation | 0.012 | 60 | 22 | 53 |
| Example 149c | N/A | Phenol Oxidation | 0.012 | 60 | 22 | 34 |
| Example 150a | 0.002 | Phenol Oxidation | 0.012 | 60 | 22 | 29 |
| Example 150b | N/A | Phenol Oxidation | 0.012 | 60 | 22 | 53 |
| Example 150c | N/A | Phenol Oxidation | 0.012 | 60 | 22 | 36 |
| Example 151a | N.D. | Phenol Oxidation | 0.012 | 60 | 22 | 30 |
| Example 151b | N/A | Phenol Oxidation | 0.012 | 60 | 22 | 40 |
| Example 151c | N/A | Phenol Oxidation | 0.012 | 60 | 22 | 37 |
| Example 152a | N.D. | Phenol Oxidation | 0.012 | 60 | 22 | 46 |
| Example 152b | N/A | Phenol Oxidation | 0.012 | 60 | 22 | 43 |
| Example 152c | N/A | Phenol Oxidation | 0.012 | 60 | 22 | 39 |
| Example 153 | 0.110 | Phenol Oxidation | 0.012 | 60 | 22 | 31 |
| Example 154 | 0.110 | Phenol Oxidation | 0.012 | 60 | 22 | 25 |
| Example 155a | N.D. | Phenol Oxidation | 0.012 | 60 | 22 | 65 |
| Example 155b | N/A | Phenol Oxidation | 0.012 | 60 | 22 | 83 |
| Example 155c | N/A | Phenol Oxidation | 0.012 | 60 | 22 | 98 |
| Example 156a | N.D. | Phenol Oxidation | 0.012 | 60 | 22 | 62 |
| Example 156b | N/A | Phenol Oxidation | 0.012 | 60 | 22 | 87 |
| Example 156c | N/A | Phenol Oxidation | 0.012 | 60 | 22 | 100 |

TABLE 13-continued

Catalytic Activity Results obtained by Static Reactor

| Example | Iron Removal degree after EDTA solution treatment (%) | Catalytic process | Catalysis mass/solution volume ratio (modulus) (kg/m$^3$) | Time of oxidation (min) | Initial concentration of substrate (mg/l) | Conversion degree (%) |
|---|---|---|---|---|---|---|
| Example 157a | N.D. | Phenol Oxidation | 0.012 | 60 | 22 | 28 |
| Example 157b | N/A | Phenol Oxidation | 0.012 | 60 | 22 | 89 |
| Example 157c | N/A | Phenol Oxidation | 0.012 | 60 | 22 | 98 |
| Example 158a | N.D. | Phenol Oxidation | 0.012 | 60 | 22 | 25 |
| Example 158b | N/A | Phenol Oxidation | 0.012 | 60 | 22 | 89 |
| Example 158c | N/A | Phenol Oxidation | 0.012 | 60 | 22 | 98 |
| Example 159a | N.D. | Phenol Oxidation | 0.012 | 60 | 22 | 11 |
| Example 159b | N/A | Phenol Oxidation | 0.012 | 60 | 22 | 16 |
| Example 159c | N/A | Phenol Oxidation | 0.012 | 60 | 22 | 82 |
| Example 160a | N.D. | Phenol Oxidation | 0.012 | 60 | 22 | 14 |
| Example 160b | N/A | Phenol Oxidation | 0.012 | 60 | 22 | 11 |
| Example 160c | N/A | Phenol Oxidation | 0.012 | 60 | 22 | 84 |
| Example 161a | N.D. | Phenol Oxidation | 0.012 | 60 | 22 | 43 |
| Example 161b | N/A | Phenol Oxidation | 0.012 | 60 | 22 | 53 |
| Example 161c | N/A | Phenol Oxidation | 0.012 | 60 | 22 | 83 |
| Example 162a | N.D. | Phenol Oxidation | 0.012 | 60 | 22 | 42 |
| Example 162b | N/A | Phenol Oxidation | 0.012 | 60 | 22 | 49 |
| Example 162c | N/A | Phenol Oxidation | 0.012 | 60 | 22 | 82 |
| Control Example 163 | N/A | Phenol Oxidation | N/A | 60 | 22 | 26 |
| Control Example 164 | N/A | Phenol Oxidation | 0.012 | 60 | 22 | 21 |
| Control Example 165 | N/A | Phenol Oxidation | 0.012 | 60 | 22 | 22 |
| Control Example 166 | N/A | Phenol Oxidation | 0.012 | 60 | 22 | 23 |
| Control Example 167 | N/A | Phenol Oxidation | 0.012 | 60 | 22 | 22 |
| Control Example 168 | N/A | Phenol Oxidation | 0.012 | 60 | 22 | 23 |
| Control Example 169 | N/A | Phenol Oxidation | 0.012 | 60 | 22 | 23 |
| Control Example 170 | N/A | Phenol Oxidation | 0.012 | 60 | 22 | 25 |
| Control Example 171 | N/A | Phenol Oxidation | 0.012 | 60 | 22 | 23 |
| Control Example 172 | N/A | Phenol Oxidation | 0.012 | 60 | 22 | 24 |
| Control Example 173 | N/A | Phenol Oxidation | 0.012 | 60 | 22 | 6 |
| Control Example 174 | N/A | Phenol Oxidation | 0.012 | 60 | 22 | 32 |
| Control Example 175 | N/A | Phenol Oxidation | 0.012 | 60 | 22 | 11 |
| Control Example 176 | N/A | Phenol Oxidation | 0.012 | 60 | 22 | 8 |
| Example 183 | N/A | Estrone Oxidation | N/A | 120 | $1 \times 10^{-3}$ | 58 |

N/A = data not available
N.D = not detected

Discussion of Results

EXAMPLES 101 TO 162 AND 183 AND CONTROL EXAMPLES 163 TO 176 EXAMPLES 101 TO 110 AND CONTROL EXAMPLES 164 TO 166

Examples 101 to 110 and Control Examples 164 to 166 all relate to catalysts made from WOOLMARK wool.

Catalysts comprising wool that was modified with a mixture of hydrazine and hydroxylamine and impregnated with $Fe^{3+}$ cations (Examples 101 to 103) had similar conversions of phenol (98 to 99%) as catalysts comprising wool modified with hydroxylamine only and impregnated with $Fe^{3+}$ cations (99 to 100%) (Examples 104 to 106).

A difference between the catalysts of Examples 101 to 103 and Examples 104 to 106 was the iron content of the catalyst and the extent of iron removal from the catalyst by EDTA. The catalysts of Examples 101 to 103, modified with a mixture of hydrazine and hydroxylamine, had an iron content of 0.044 mmol/g wool and the catalysts of Examples 104 to 106, modified with hydroxylamine only, had an iron content of 0.076 mmol/g wool. In the catalysts of Examples 101 to 103 0.002% of iron was removed, whereas for the catalysts of Examples 104 to 106 iron could not be detected in solution after exposure to EDTA and hence was not removed. Without wishing to be bound by any theory, it is believed that the higher iron loading and retention for the catalysts of Examples 104 to 106 potentially may produce a more efficient catalyst with respect to phenol conversion and catalyst lifetime.

In the catalysts of Examples 107 and 108 (with scouring) and 109 and 110 (without scouring), where there was no modification of the wool prior to impregnation with $Fe^{3+}$ cations, the iron content was reduced and the iron removal was increased, compared to the catalysts of Examples 101 to 106 with a modification step. Typically, the catalysts of Examples 107 to 110 also provided reduced conversions of phenol compared to Examples 101 to 106.

A comparison of the catalyst of Control Example 164 with the catalysts of Examples 101 to 103, of the catalyst of Control Example 165 with the catalysts of Examples 104 to 106 and of the catalyst of Control Example 166 with the catalysts of Examples 107 and 108 shows that without the presence of the active catalyst site (i.e. $Fe^{3+}$) the conversion degree of phenol is minimal. Thus impregnation with first metal ions (i.e. $Fe^{3+}$) is necessary in order to optimise the catalyst performance.

EXAMPLES 111 TO 114

Examples 111 to 114 all relate to catalysts made from DEFRA wool. Catalysts comprising wool that was modified with a mixture of hydrazine and hydroxylamine (Example 114), with hydroxylamine only (Example 113) and with hydrazine only (Example 112), and impregnated with $Fe^{3+}$ cations had improved conversions of Acid Blue 45 compared to a catalyst comprising wool that was impregnated with $Fe^{3+}$ cations but not modified (Example 111). The catalysts of Examples 112 to 114 had a higher iron loading and retention than the catalyst of Example 111.

EXAMPLES 115 TO 124 AND CONTROL EXAMPLES 167 TO 169

Examples 115 to 124 and Control Examples 167 to 169 all relate to catalysts made from DEFRA wool.

Catalysts comprising wool that was modified with a mixture of hydrazine and hydroxylamine and impregnated with $Fe^{3+}$ cations (Examples 115 to 117) and modified with hydroxylamine only and impregnated with $Fe^{3+}$ cations (Examples 118 to 120) had improved conversions of phenol compared to catalysts impregnated with $Fe^{3+}$ cations where the wool was not modified (Examples 121 and 122).

A difference between Examples 115 to 117 and 118 to 120 was the iron content of the catalyst and the extent of iron removal from the catalyst by EDTA. The catalysts of Examples 115 to 117, modified with a mixture of hydrazine and hydroxylamine, had an iron content of 0.037 mmol/g wool and the catalysts of Examples 118 to 120, modified with hydroxylamine only, had an iron content of 0.076 mmol/g wool. In the catalysts of Examples 15 to 17 0.001% of iron was removed, whereas for the catalysts of Examples 118 to 120 iron could not be detected in solution after exposure to EDTA and hence was not removed. Without wishing to be bound by any theory, it is believed that the higher iron loading and retention for the catalysts of Examples 118 to 120 potentially may produce a more efficient catalyst with respect to phenol conversion and catalyst lifetime.

In the catalysts of Examples 121 and 122 (with scouring) and 123 and 124 (without scouring), where there was no modification of the wool prior to impregnation with $Fe^{3+}$ cations, the iron content was reduced and the iron removal was increased, compared to the catalysts of Examples 115 to 120 with a modification step. Typically, Examples 121 to 124 also provided reduced conversions of phenol compared to Examples 115 to 120.

A comparison of the catalyst of Control Example 167 with the catalysts of Examples 115 to 117, of the catalyst of Control Example 168 with the catalysts of Examples 118 to 120 and of the catalyst of Control Example 169 with the catalysts of Examples 121 and 122 shows that without the presence of the active catalyst site (i.e. $Fe^{3+}$) the conversion degree of phenol is minimal. Thus impregnation with first metal ions (i.e. $Fe^{3+}$) is necessary in order to optimise the catalyst performance.

EXAMPLES 125 TO 140 AND CONTROL EXAMPLES 170 TO 172

Examples 125 to 140 and Control Examples 170 to 172 all relate to catalysts made from Herdwick wool.

Catalysts comprising wool that was modified, with a mixture of hydrazine and hydroxylamine (Examples 125 to 127, 135 and 136) and with hydroxylamine only (Examples 128 to 130, 137 and 138), and impregnated with $Fe^{3+}$ cations had improved conversions of phenol compared to the catalyst comprising wool that was impregnated with $Fe^{3+}$ cations but not modified (Examples 131, 132, 139 and 140).

A comparison of the catalyst of Control Example 170 with the catalysts of Examples 135 and 136, of the catalyst of Control Example 171 with the catalysts of Examples 137 and 138 and of the catalyst of Control Example 172 with the catalysts of Examples 139 and 140 shows that without the presence of the active catalyst site (i.e. $Fe^{3+}$) the conversion degree of phenol is minimal. Thus impregnation with first metal cations (i.e. $Fe^{3+}$) is necessary in order to optimise the catalyst performance.

EXAMPLES 141 TO 154

Examples 141 to 154 all relate to catalysts made from Swaledale wool.

Catalysts comprising wool that was modified, with a mixture of hydrazine and hydroxylamine (Examples 141, 142, 149 and 150) and with hydroxylamine only (Examples 143, 144, 151 and 152), and impregnated with $Fe^{3+}$ cations generally had improved conversions of phenol compared to the catalyst comprising wool that was impregnated with $Fe^{3+}$ cations but not modified (Examples 145, 146, 153 and 154).

The catalysts of Examples 141 to 143 and 151 to 154 had a higher iron loading and retention than the catalyst of Examples 145 to 148, 153 and 154.

EXAMPLE 183

Example 183 relates to a catalyst made from CROSSES wool, modified with hydroxylamine only and impregnated with $Fe^{3+}$ and $Ca^{2+}$ cations. The catalyst was effective in the oxidative decomposition of Estrone.

SUMMARY

The catalysts comprising a wool fibre and an iron cation fixed to the wool fibre were all catalytically active in Examples 101 to 162. It is believed that the Control Examples that use a wool fibre to which no iron cation is fixed apparently show some conversion due to possible sorption of hydrogen peroxide and/or chemical reaction of hydrogen peroxide with the wool. However, it is clear that the wool fibre with an iron cation fixed thereto acts as an efficient catalyst in the oxidation reactions shown above.

In general, catalysts prepared from wools that were modified prior to impregnation, especially wools modified with hydroxylamine only, have higher iron contents and higher phenol conversions. Additionally, modified wool samples appear to allow iron to be fixed more strongly to the wool (as the iron removal by EDTA is lower than for unmodified samples). In general, for catalysts made from wools that were modified, good batch-to-batch reproducibility was achieved.

Additionally, for catalysts where the wool was not modified prior to impregnation, it was generally observed that iron content was lower, with the amount of iron removed by EDTA greater. Typically, phenol conversions were lower than those obtained using modified wool, but these catalysts still showed improved phenol conversions over wool containing no iron cations.

EXAMPLES 177 TO 182

Examples 177 to 182 relate to the evaluation of the catalysts for catalytic activity using a dynamic flow reactor. In these Examples, the wool was modified with hydroxylamine prior to impregnation with iron cations. All catalytic activity evaluations contained hydrogen peroxide (50 ppm) in the feed.

In Examples 177 to 182, the activity of the catalyst was determined in relation to the decomposition (by oxidation) of phenol.

In Examples 177 to 182, the catalysts were evaluated in a dynamic reactor.
Phenol Decomposition Examples 177 to 182 were conducted as follows: Catalyst (2 g) was placed in a reactor and air was bubbled through at a rate of 45 ml $min^{-1}$ as measured and controlled by a flow meter. A continuous flow of aqueous phenol solution (24 ppm) containing hydrogen peroxide (50 ppm) was pumped through the reactor at a flow of 2 nil $min^{-1}$. The retention time within the reactor was 30 minutes. Samples were taken from the reactor outlet at regular time intervals and analysed for phenol by HPLC (using a Waters 510 HPLC pump). A standard C-18 (250×4.6 mm) packed column was used for the stationary phase. The mobile phase was a mixture of methanol (40%) and double distilled water (60%) with a flow of 1 ml $min^{-1}$. Sample volumes of 20 µl were injected and detected using UV (using a Philips PYE UNICAM PU 4025 UV Detector at $\lambda_{max}$=254 nm). The sample times were 5, 15, 30, 90, 120, 150, 180, 210, 240 and 300 minutes and then every 60 minutes until deactivation occurred and no further decrease in phenol concentration was observed (catalyst no longer active). Multiple samples from the same production batch were evaluated where deemed necessary.

The data collected in each dynamic study was used to calculate the following values:
The yield degree ($\alpha$) of the substance (the substance being phenol in Examples 177 to 182)
The mass (M) of the substance decomposed (the substance being phenol in Examples 177 to 182)
The turn-over frequency (TOF)
The yield degree of the substance ($\alpha$) was calculated using the following equation:

$$\alpha = \frac{S}{\frac{C_t}{C_0} \times t}$$

where:
S=Area above the dynamic curve calculated by the total area minus the area below the curve obtained by integration using a suitable computer program, in these examples using the computer program Origin (see FIG. 1 relating to Example 178)

$$\frac{C_t}{C_0} = \text{ratio}$$

between concentration of the substance in solution at time t ($C_t$) and initial concentration ($C_0$)
t=duration of the process (minutes)
The total area in FIG. 1 is 2520 ($x_{max} \times y_{max}$) and the area below the curve obtained through integration is 589.35, therefore in this case S=2520−589.35.

Mass of the substance decomposed (by oxidation) M (mg) on the catalyst during the dynamic process was calculated as follows:

$$M = \alpha \times Q \times t \times C_0$$

where:
$\alpha$=the yield degree of the substance (calculated as set out above)
Q=flow rate (ml/min), which was 2 ml/min for all experiments
t=duration of the process (minutes)
$C_0$=initial concentration of the substance in solution
Turn-Over Frequency (TOF) is expressed as follows and relates the amount of phenol decomposed to the active sites on the catalyst:

$$TOF = \frac{[\text{Phenol}]}{[\text{Fe}] \times [\text{Wool}] \times t}$$

where:
[Phenol]=amount of phenol decomposed (mmol)
[Fe]=concentration of iron (mmol/g wool)

[Wool]=amount of wool support (g), which was 2 g in all cases.

Table 14 shows the results obtained for the dynamic evaluation. It is desirable to achieve the highest possible catalysts lifetime and/or the highest possible TOF.

EXAMPLE 177

In Example 177, the catalyst used was Crosses wool that was laboratory scoured, modified with hydroxylamine and impregnated with $Fe^{3+}$ cations.

EXAMPLES 178 AND 179

In Examples 178 and 179, the catalysts used were Crosses wool that was mill scoured, modified with hydroxylamine and impregnated with $Fe^+$ cations. Example 178 was from one batch of catalyst prepared and Example 179 from another to investigate reproducibility.

EXAMPLE 180

In Example 180, the catalyst used was Crosses wool that was mill scoured, modified with hydroxylamine and impregnated with $Fe^{3+}$ and $Ca^{2+}$ cations.

EXAMPLES 181 AND 182

In Examples 181 and 182, the catalysts used were Crosses wool that was mill scoured, modified with hydroxylamine and impregnated with $Fe^{3+}$ and $Li^+$ cations. Two batches were again investigated for reproducibility.

Table 14 contains the results for the wool catalysts of Examples 177 to 182 evaluated in the dynamic reactor.

TABLE 14

Catalytic Activity Results for Examples 177 to 182

| Example | Reactor volume (ml) | Retention time (min) | Catalytic process | Feed concentration (mg/l) | Catalyst lifetime (hours) | Phenol decomposed (mg) | TOF ($\times 10^{-3}$) (min$^{-1}$) |
|---|---|---|---|---|---|---|---|
| Example 177 | 60 | 30 | Phenol Oxidation | 24 | 42 | 99.915 | 2.4018 |
| Example 178 | 60 | 30 | Phenol Oxidation | 24 | 42 | 99.930 | 2.8544 |
| Example 179 | 60 | 30 | Phenol Oxidation | 24 | 42 | 103.065 | 2.6789 |
| Example 180 | 60 | 30 | Phenol Oxidation | 24 | 49 | 132.289 | 2.9730 |
| Example 181 | 60 | 30 | Phenol Oxidation | 24 | 60 | 154.565 | 2.8835 |
| Example 182 | 60 | 30 | Phenol Oxidation | 24 | 60 | 158.006 | 2.9477 |

As shown in Table 14, the catalysts of Examples 177 to 179 had similar catalytic activity, with a lifetime of 42 hours. The lifetime and TOF was improved using an impregnation solution of $Fe^{3+}/Ca^{2+}$ or $Fe^{+3}/Li^+$ (see Examples 180 to 182). Example 180 showed that using $Fe^{3+}/Ca^{2+}$ the lifetime was increased to 49 hours and the TOF increased to $2.9730 \times 10^{-3}$ min$^{-1}$. Using $Fe^{+3}/Li^+$, the lifetime was improved to 60 hours with consequently more phenol decomposed, however TOF remained at about $2.9100 \times 10^{-3}$ min$^{-1}$ (Examples 181 and 182).

The invention claimed is:

1. A composition for killing and/or inactivating microbes, the composition comprising a catalyst, a peroxygen compound and a fluid medium, wherein the catalyst comprises a solid, keratinous or polymeric support, comprising one or more fibres, having a transition metal cation fixed thereto in an amount of 0.03 mmol or greater per gram of the support by means of the following manufacturing steps:
   (i) treating the support with a hydrazine salt and a hydroxylamine salt in the presence of a base to provide a modified support;
   (ii) treating the modified support with a base; and
   (iii) treating the modified support with an aqueous solution comprising an amount of a salt of a transition metal cation and a salt of a non-transition metal cation, wherein the non-transition metal cation comprises a metal from Group 1, 2, 12, 13, 14 or 15 of the Periodic Table of Elements.

2. A composition according to claim 1, wherein the fluid medium is a liquid medium.

3. An apparatus for killing and/or inactivating microbes, the apparatus comprising a catalyst, a peroxygen compound and a fluid medium, wherein the catalyst comprises a solid, keratinous or polymeric support, comprising one or more fibres, having a transition metal cation fixed thereto in the amount of 0.03 mmol or greater per gram of the support by means of the following manufacturing steps:
   (i) treating the support with a hydrazine salt and a hydroxylamine salt in the presence of a base to provide a modified support;
   (ii) treating the modified support with a base; and
   (iii) treating the modified support with an aqueous solution comprising an amount of a salt of a transition metal cation and a salt of a non-transition metal cation, wherein the non-transition metal cation comprises a metal from Group 1, 2, 12, 13, 14 or 15 of the Periodic Table of Elements.

4. An apparatus according to claim 3, wherein the fluid medium is a liquid medium.

5. An apparatus according to claim 3, wherein the catalyst and the peroxygen compound are spaced apart in the apparatus.

6. A method of killing and/or inactivating microbes, the method comprising the step of placing the microbes in contact with a catalyst by means of a fluid medium, wherein the catalyst comprises a solid, keratinous or polymeric support, comprising one or more fibres, having a transition metal cation fixed thereto in an amount of 0.03 mmol or greater per gram of the support by means of the following manufacturing steps:

(i) treating the support with a hydrazine salt and a hydroxylamine salt in the presence of a base to provide a modified support;
(ii) treating the modified support with a base; and
(iii) treating the modified support with an aqueous solution comprising an amount of a salt of a transition metal cation and a salt of a non-transition metal cation, wherein the non-transition metal cation comprises a metal from Group 1, 2, 12, 13, 14 or 15 of the Periodic Table of Elements.

7. A method according to claim 6, wherein the catalyst is contacted with the microbes in the presence of an oxidant, wherein the oxidant is optionally (a) a peroxygen compound, or (b) atmospheric oxygen.

8. The method of claim 7, wherein the peroxygen compound is selected from the group consisting of (i) hydrogen peroxide, (ii) hydrogen peroxide liberating compounds, (iii) hydrogen peroxide-generating compounds, (iv) organic and inorganic peroxyacids, and salts thereof, and mixtures thereof.

9. The method of claim 8, wherein the keratinous support comprises wool fibres or polyacrylonitrile fibres.

10. A method according to claim 6, wherein the fluid medium is a liquid medium, which is optionally polar and/or aqueous.

11. A method according to claim 6, wherein the transition metal cation is selected from a scandium, titanium, vanadium, chromium, manganese, iron, cobalt, nickel, copper, yttrium, zirconium, niobium, molybdenum, technetium, ruthenium, rhodium, palladium, silver, hafnium, tantalum, tungsten, rhenium, osmium, iridium, platinum, gold, and mixtures thereof.

12. The method of claim 11, wherein the transition metal cation is selected from a scandium, titanium, vanadium, chromium, manganese, iron, cobalt, nickel and copper cation, and mixtures thereof.

13. The method of claim 12, wherein the transition metal cation is an iron cation.

* * * * *